(12) United States Patent
Kim et al.

(10) Patent No.: US 10,525,022 B2
(45) Date of Patent: Jan. 7, 2020

(54) PHARMACEUTICAL COMPOSITION FOR TREATING CANCER, CONTAINING LACTATE METAL SALT

(71) Applicant: MetiMedi Pharmaceuticals Co., Ltd., Incheon (KR)

(72) Inventors: Hwan Mook Kim, Daejeon (KR); Keun Yeong Jeong, Seoul (KR); Jae Jun Sim, Seoul (KR); Yeong Su Jang, Incheon (KR)

(73) Assignee: METIMEDI PHARMACEUTICALS CO., LTD., Incheon (KR)

( * ) Notice: Subject to any disclaimer, the term of this patent is extended or adjusted under 35 U.S.C. 154(b) by 0 days.

(21) Appl. No.: 15/629,445

(22) Filed: Jun. 21, 2017

(65) Prior Publication Data

US 2017/0360727 A1 Dec. 21, 2017

Related U.S. Application Data

(63) Continuation of application No. PCT/KR2015/013191, filed on Dec. 4, 2015.

(30) Foreign Application Priority Data

Dec. 29, 2014 (KR) .................. 10-2014-0192158
Oct. 13, 2015 (KR) .................. 10-2015-0142828

(51) Int. Cl.
| | | |
|---|---|---|
| A61K 31/19 | (2006.01) | |
| A61K 9/00 | (2006.01) | |
| A61K 9/08 | (2006.01) | |
| A61K 9/48 | (2006.01) | |
| A61K 9/70 | (2006.01) | |
| A61K 31/436 | (2006.01) | |
| A61K 31/404 | (2006.01) | |
| A61K 31/4745 | (2006.01) | |
| A61K 31/506 | (2006.01) | |
| A61K 31/513 | (2006.01) | |
| A61K 33/04 | (2006.01) | |
| A61K 33/06 | (2006.01) | |
| A61K 33/30 | (2006.01) | |
| A61K 33/34 | (2006.01) | |
| A23L 33/00 | (2016.01) | |
| A23L 33/16 | (2016.01) | |
| A61K 31/337 | (2006.01) | |
| A61K 31/44 | (2006.01) | |
| A61K 31/517 | (2006.01) | |
| A61K 31/519 | (2006.01) | |
| A61K 31/5377 | (2006.01) | |

(Continued)

(52) U.S. Cl.
CPC .............. *A61K 31/19* (2013.01); *A23L 33/16* (2016.08); *A23L 33/30* (2016.08); *A61K 9/00* (2013.01); *A61K 9/0019* (2013.01); *A61K 9/0053* (2013.01); *A61K 9/0056* (2013.01); *A61K 9/08* (2013.01); *A61K 9/48* (2013.01); *A61K 9/70* (2013.01); *A61K 31/191* (2013.01); *A61K 31/337* (2013.01); *A61K 31/404* (2013.01); *A61K 31/436* (2013.01); *A61K 31/44* (2013.01); *A61K 31/4745* (2013.01); *A61K 31/506* (2013.01); *A61K 31/513* (2013.01); *A61K 31/517* (2013.01); *A61K 31/519* (2013.01); *A61K 31/5377* (2013.01); *A61K 31/555* (2013.01); *A61K 33/04* (2013.01); *A61K 33/06* (2013.01); *A61K 33/30* (2013.01); *A61K 33/34* (2013.01); *A61K 39/39558* (2013.01); *A61K 45/06* (2013.01); *A61N 5/10* (2013.01); *A23V 2002/00* (2013.01); *A61N 2005/1098* (2013.01)

(58) Field of Classification Search
CPC ..................................................... A61K 31/19
See application file for complete search history.

(56) References Cited

U.S. PATENT DOCUMENTS

| | | | |
|---|---|---|---|
| 5,980,863 A | 11/1999 | Harnish et al. | |
| 6,036,985 A | 3/2000 | Jacobson et al. | |

(Continued)

FOREIGN PATENT DOCUMENTS

| | | |
|---|---|---|
| CN | 103110133 A | 5/2013 |
| CN | 103535580 A | 1/2014 |

(Continued)

OTHER PUBLICATIONS

Vinas_Salas et al., Calcium Inhibits Colon Carcinogenesis in an Experimental Model in the Rat, 1998, European Journal of Cancer, vol. 34, No. 12, pp. 1941-1945. (Year: 1998).*

(Continued)

*Primary Examiner* — James D. Anderson
(74) *Attorney, Agent, or Firm* — Lucas & Mercanti, LLP

(57) ABSTRACT

The present invention relates to: a pharmaceutical composition for treating cancer containing, as an active ingredient, a metal lactate salt, which can be dissociated, in cancer cells, into lactate capable of effectively inhibiting actions such as proliferation, invasion, and metastasis of cancer cells by disturbing the metabolic processes of cancer cells; a pharmaceutical composition for inhibiting cancer metastasis; a food composition for alleviating cancer; and a method for treating cancer and a method for inhibiting cancer metastasis, both methods comprising a step of administering the lactate metal salt. The metal lactate salts of the present invention inhibits the growth of cancer cells and induces the death of cancer cells by disturbing the metabolic processes in the main energy production pathways of cancer, and inhibits the expression of factors inducing resistance against radiation exposure, while having no side effects. Therefore, the lactate metal salt can be widely utilized in a more effective anti-cancer therapy.

23 Claims, 45 Drawing Sheets
Specification includes a Sequence Listing.

(51) Int. Cl.
    *A61K 31/555*     (2006.01)
    *A61K 39/395*     (2006.01)
    *A61N 5/10*     (2006.01)
    *A61K 45/06*     (2006.01)
    *A61K 31/191*     (2006.01)

(56) References Cited

U.S. PATENT DOCUMENTS

| | | | |
|---|---|---|---|
| 6,251,439 B1 * | 6/2001 | Baron | A61K 31/19 424/678 |
| 6,261,610 B1 | 7/2001 | Sher et al. | |
| 6,306,902 B1 | 10/2001 | Anderson et al. | |
| 6,428,785 B1 | 8/2002 | Gokcen | |
| 6,913,744 B2 | 7/2005 | Gokcen | |
| 7,323,439 B2 | 1/2008 | Crabtree et al. | |
| 7,423,063 B2 | 9/2008 | Bartorelli | |
| 7,705,051 B2 | 4/2010 | Gobbi | |
| 8,871,458 B2 | 10/2014 | Schwartz et al. | |
| 2002/0106396 A1 | 8/2002 | Herzog et al. | |
| 2004/0253323 A1 | 12/2004 | Giles | |
| 2005/0148661 A1 | 7/2005 | Gamelin et al. | |
| 2005/0260277 A1 | 11/2005 | Giles | |
| 2006/0115538 A1 | 6/2006 | Krauskopf et al. | |
| 2007/0292493 A1 | 12/2007 | Brierre | |
| 2008/0085248 A1 | 4/2008 | Sela | |
| 2008/0113041 A1 | 5/2008 | Baron | |
| 2010/0015068 A1 | 1/2010 | Karp et al. | |
| 2011/0117210 A1 | 5/2011 | Ugolkov | |
| 2012/0064178 A1 | 3/2012 | Dean et al. | |
| 2012/0083531 A1 | 4/2012 | Clarke et al. | |
| 2015/0065946 A1 | 3/2015 | Gehl et al. | |
| 2015/0366908 A1 | 12/2015 | Pomrink et al. | |

FOREIGN PATENT DOCUMENTS

| | | |
|---|---|---|
| EP | 1 129 715 A1 | 2/2000 |
| EP | 1 242 110 B1 | 9/2007 |
| EP | 1 365 810 B1 | 1/2010 |
| EP | 2 599 477 A1 | 6/2013 |
| EP | 2 799 060 A1 | 11/2014 |
| KR | 100941210 | 2/2010 |
| KR | 10-2014-0037278 | 3/2014 |
| WO | WO 1999/51114 A1 | 10/1999 |
| WO | WO 2000/25671 A1 | 5/2000 |
| WO | WO 2000/067750 A1 | 11/2000 |
| WO | WO 2001/22838 A1 | 4/2001 |
| WO | WO 2001/34176 A1 | 5/2001 |
| WO | WO 2002/24957 A1 | 3/2002 |
| WO | WO 2003/006031 A1 | 1/2003 |
| WO | WO 2003/047587 A1 | 6/2003 |
| WO | WO 2003/059361 A1 | 7/2003 |
| WO | WO 2003/063836 A1 | 8/2003 |
| WO | WO 2005/077405 A1 | 8/2005 |
| WO | WO 2006/072940 A2 | 7/2006 |
| WO | WO 2007/065441 A1 | 6/2007 |
| WO | WO 2008/005509 A2 | 1/2008 |
| WO | WO 2010/111650 A2 | 9/2010 |
| WO | WO 2011/152810 A1 | 12/2011 |
| WO | WO 2013/091657 A1 | 6/2013 |
| WO | WO 2013/126031 A1 | 8/2013 |
| WO | WO 2013/133873 A2 | 9/2013 |
| WO | WO 2013/184943 A1 | 12/2013 |
| WO | WO 2015/180600 A1 | 12/2015 |
| WO | WO 2016/103695 A1 | 6/2016 |

OTHER PUBLICATIONS https://en.wikipedia.org/wiki/Carcinogenesis, accessed Oct. 15, 2018, 29 pages. (Year: 2018).*

Jang, Y.S. et al., "Investigation of Lactate Calcium Salt-Induced β-catenin Destabilization in Colorectal Cancer Cells," Life Sciences 139:160-165 (Aug. 2015), Elsevier, Inc., Atlanta, GA, with Supplement.

Sundaramoorthy, P. et al., "Modulation of Intracellular Calcium Levels by Calcium Lactate Affects Colon Cancer Cell Motility Through Calcium-Dependent Calpain," PLOS One, pp. 1-15 (Jan. 2015), Public Library of Science.

Davies, C.W., "The Extent of Dissociation of Salts in Water. Part VI. Some Calcium Salts of Organic Acids", pp. 277-281 (1938) (downloaded by Northeastern University on Oct. 27, 2014), Royal Society of Chemistry, London, UK.

Lee, D.C. et al., "A Lactate-Induced Response to Hypoxia", Cell 161:595-609 (Apr. 2015), Cell Press Cambridge, MA.

Dillion, E. L. et al., "Lactate Inhibits Citrulline and Arginine Synthesis from Proline in Pig Enterocytes", pp. G1079-G1086 (Dec. 1998) (downloaded from http://ajpgi.physiology.org on Feb. 1, 2017), American Physiological Society.

English translation of International Search Report of PCT/KR2015/013191 dated Mar. 14, 2016 issued by WIPO, Republic of Korea.

Wargovich, M.J., et al., "Inhibition of the Promotional Phase of Azoxymethane-induced Colon Carcinogenesis in the F344 Rat by Calcium Lactate: Effect of Simulating Two Human Nutrient Density Levels", Cancer Letters 53:17-25 (Apr. 1990), Elsevier Scientific Publishers Ireland Ltd.

Stevens, C.D., et al., "Inhibition of an Ehrlich Ascites Tumor In Vivo by Partially Neutralized Solutions of Sodium Lactate", 17:315-319 (Jun. 1963), British Journal of Cancer, United Kindom.

Supplementary European Search report of EP 15 87 5540 dated Jun. 6, 2018, issued by the European Patent Office, Munich, Germany.

Rogers, A.E.et al., "Induction by Dimethylhydrazine of Intestinal Carcinoma in Normal Rats and Rats Fed High or Low Levels of Vitamin A," Cancer Research, American Association for Cancer Research, Philadelphia, Pennsylvania, vol. 33, May 1973, pp. 1003-1009.

Fournier, P.E. et al., "Mechanisms of chemical carcinogenesis: recent advances," Food Additives and Contaminants, Taylor & Francis Group, London, England, vol. 1, No. 2, May 1984, pp. 73-80.

Stein, W.D. "Transport and Diffusion across Cell Membranes," Science, Academic Press, vol. 233, 1986, pp. 898.

Sheikh, M.D., M.S. et al., "Gastrointestinal Absorption of Calcium from Milk and Calcium Salts," The New English Journal of Medicine, Massachusetts Medical Society, Massachusetts Medical Society, Waltham, Massachusetts, vol. 317, No. 9, Aug. 1987, pp. 532-536.

Harris, C.C., "Chemical and Physical Carcinogenesis: Advances and Perspectives for the 1990s", Cancer Research, American Association for Cancer Research, Philadelphia, Pennsylvania, vol. 51, Sep. 1991, pp. 5023s-5044s.

Sitrin, M.D. et al., "Dietary Calcium and Vitamin D Modulate 1, 2-Dimethylhydrazine-induced Colonic Carcinogenesis in the Rat," Cancer Research, American Association for Cancer Research, Philadelphia, Pennsylvania, vol. 51, Oct. 1991, pp. 5608-5613.

Cooper, D.J. et al., "Plasma ionized calcium and blood lactate concentrations are inversely associated in human lactic acidosis*," Intensive Care Medicine, Springer-Verlag, vol. 18, 1992, pp. 286-289.

Beaty, M.M. et al., "Influence of Dietary Calcium and Vitamin D on Colon Epithelial Cell Proliferation and 1, 2-Dimethylhydrazin-Induced Colon Carcinogenesis in Rats Fed High Fat Diets," The Journal of Nutrition, Wistar Institute of Anatomy and Biology; American Institute of Nutrition; American Society for Nutritional Sciences; American Society for Nutrition, American Society for Nutrition, vol. 123, Jan. 1993, pp. 144-152.

Pence, B.C., "Role of calcium in colon cancer prevention: Experimental and clinical studies," Mutation Research, Elsevier, vol. 290, Nov. 1993, pp. 87-95.

Kelloff, G.J. et al., "Strategies for Identification and Clinical Evaluation of Promising Chemopreventive Agents," Oncology (Williston Park, NY), vol. 10, No. 10, Oct. 1996, pp. 1-7 and 1-9 (2 Parts).

Baron, J.A. et al., "Calcium Supplements and Colorectal Adenomas," Annals of New York Academy of Sciences, The New York Academy of Sciences, 1999, pp. 138-145.

Bronner, F. et al., "Nutritional Aspects of Calcium Absorption," The Journal of Nutrition, American Society for Nutritional Services, Jan. 1999, pp. 9-12.

(56) References Cited

OTHER PUBLICATIONS

Ghadi, F.E. et al., "Chemopreventive Effects of Selenium on Cancer Marker Indices and Ultrastructural Changes During 1,2 Dimethylhydrazine-Induced Colon Carcinogenesis in Rats," Journal of Gastrointestal Cancer, Springer US, vol. 44, No. 1, Mar. 2003, pp. 54-59.

Lamprecht, S.A. et al., "Chemoprevention of Colon Cancer by Calcium, Vitamin D and Folate: Molecular Mechanisms," Nature Reviews, Springer Nature Publishing AG, vol. 3, Aug. 2003, pp. 601-614.

Key, T.J., "Diet, nutrition and the prevention of cancer," Public Health Nutrition, CAB International, vol. 7(1A), Feb. 2004, pp. 187-200.

Kubantseva, N. et al., "Factors Affecting Solubility of Calcium Lactate in Aqueous Solutions," Journal of Dairy Science, Elsevier, vol. 87, Apr. 2004, pp. 863-867.

Tsao, A.S. et al., "Chemoprevention of Cancer," A Cancer Journal of Clinicians, Oxford University Press, vol. 54, No. 3, May 2004, pp. 150-180.

Cho, E. et al., "Dairy Foods, Calcium, and Colorectal Cancer: A Pooled Analysis for 10 Cohort Studies," Journal of the National Cancer Institute, Oxford University Press, vol. 96, No. 13, Jul. 2004, pp. 1015-1022.

Shaukat, A. et al., "Role of Supplemental Calcium in the Recurrence of Colorectal Adenomas: A Metaanalysis of Randomized Controlled Trials," American Journal of Gastroenterology, Springer Nature Publishing AG, Feb. 2005, pp. 390-394.

Wactawski-Wende, J. et al., "Calcium plus Vitamin D Supplementation and the Risk of Colorectal Cancer," The New England Journal of Medicine, Massachusetts Medical Society, vol. 354, Feb. 2006, pp. 684-696.

Oliveira, P.A. et al., "Chemical Carcinogenesis," Anais da Academia Brasileira de Ciencias—Annals of the Brazilian Academy of Sciences, vol. 79, No. 4, Dec. 2007, pp. 593-616.

Loeb, L.A. et al., "Advances in Chemical Carcinogenesis: A Historical Review and Prospective," Cancer Research, American Association for Cancer Research, Philadelphia, Pennsylvania, vol. 68, No. 17, Sep. 2008, pp. 1-21.

Eisenhauer, E.A. et al., "New response evaluation criteria in solid tumours: Revised RECIST guideline (version 1.1)," European Journal of Cancer, Elsevier, vol. 45, Jan. 2009, pp. 228-247.

Rosenberg, D.W. et al., "Mouse models for the study of colon carcinogenesis," Carcinogenesis, Oxford University Press, vol. 30, No. 2, Feb. 2009, pp. 183-196.

Yi, H. et al., "Pharmacokinetic properties and antitumor efficacy of the 5-fluorouracil loaded PEG-hydrogel," BMC Cancer, Springer Science + Business Media, The Netherlands, vol. 10, May 2010, pp. 1-8.

Annibaldi, A. et al., "Glucose metabolism in cancer cells," Current Opinion in Clinical Nutrition and Metabolic Care, Wolters Kluwer Health, Lippincott Williams & Wilkins, vol. 13, No. 4, Jul. 2010, pp. 466-470.

Hail Jr., N., "Mitochondria: A novel target for the chemoprevention of cancer," Apoptosis, Springer Science + Business Media, The Netherlands, vol. 10, Aug. 2010, pp. 687-705.

Saw C. L-L. et al., "Anti-cancer and potential chemopreventive actions of ginseng by activating Nrf2 (NFE2L2) anti-oxidative stress/anti-inflammatory pathways," Chinese Medicine, International Society for Chinese Medicine, BioMed Central, vol. 5, No. 37, Oct. 2010, pp. 1-7.

Nakayama, Y. et al., "Prognostic significance of monocarboxylate transporter 4 expression in patients with colorectal cancer," Experimental and Therapeutic Medicine, Spandidos Publications, vol. 3, Jan. 2012, pp. 25-30.

Marin, J.J.G. et al. "Chemoprevention, chemotherapy, and chemoresistance in colorectal cancer," Drug Metabolism Review, Taylor & Francis Group, vol. 44, No. 2, May 2012, pp. 148-172.

Steward, W P et al., "Cancer chemoprevention: a rapidly evolving field," British Journal of Cancer, Cancer Research Campaign (Great Britain); British Association for Cancer Research; British Oncological Association; Association of Cancer Physicians, Cancer Research UK, vol. 109, 2013, pp. 1-7.

Rui, L., "Energy Metabolism in the Liver," Comprehensive Physiology, American Physiological Society, vol. 4, Jan. 2014, pp. 177-197.

Costi, R. et al., "Palliative care and end-stage colorectal cancer management: The surgeon meets the oncologist," World Journal of Gastroenterology, Baishideng Publishing Group Inc., Pleasanton, California, vol. 20, No. 24, Jun. 2014, pp. 7602-7621.

Vinothkumar, R. et al., "Chemopreventive effect of zingerone against colon carcinogenesis induced by 1, 2-dimetheylhydrazine in rats," European Journal of Cancer Prevention, European Cancer Prevention Organisation, Lippincott, Williams & Wilkins, vol. 23, No. 5, Sep. 2014, pp. 361-371.

Upadhyay, S. et al., "Chemotherapy use in stage III colon cancer: a National Cancer Database analysis," Therapeutic Advances in Medical Oncology, American Society of Clinical Oncology, Alexandria, Virginia, vol. 7, No. 5, 2015, pp. 244-251.

Jang, Y-S et al., "Investigation of lactate calcium salt-induced β-catenin destabilization in colorectal cancer cells," Life Sciences, Elsevier, vol. 139, Oct. 2015, pp. 160-165.

Varghese, A.,"Chemotherapy for Stage II Colon Cancer," Clinics in Colon and Rectal Surgery, Thieme Medical Publishers, vol. 28, Dec. 2015, pp. 256-261.

Evans, J.P. et al., "From mice to men: Murine models of colorectal cancer for use in translational research," Critical Reviews in Oncology/Hematology, Elsevier Ireland Ltd., vol. 98, Feb. 2016, pp. 94-105.

Jang, Y-S et al., "Lactate calcium salt affects the viability of colorectal cancer cells via betaine homeostasis," Life Sciences, Elsevier, vol. 147, Feb. 2016, pp. 71-76.

Jeong, K-Y et al., "Combination of lactate calcium salt with 5-indanesulfonamide and a-cyano-4-hydroxycinnamic acid to enhance the antitumor effect on HCT116 cells via intracellular acidification," Oncology Letters, Spandidos Publications, vol. 11, Mar. 2016, pp. 1866-1872.

Schwartz, L.H. et al., "RECIST 1.1—Update and Clarification: From the RECIST Committee," European Journal of Cancer, Elsevier Inc., vol. 62, Jul. 2016, pp. 132-137.

Park, M. et al., "Synergistically Anti-metastatic Effect of 5-Flourouracil on Colorectal Cancer Cells via Calcium-mediated Focal Adhesion Kinase Proteolysis," Anticancer Research, The International Institute of Anticancer Research, vol. 37, Jan. 2017, pp. 103-114.

San-Millan, I. et al., "Reexamining cancer metabolism: lactate production for carcinogenesis could be the purpose and explanation of the Warburg Effect," Carcinogenesis, Oxford University Press (OUP), vol. 28, No. 2, Feb. 2017, pp. 119-133.

Jo, Y-K et al., "Enhancement of the Antitumor Effect of Methotrexate on Colorectal Cancer Cells via Lactate Calcium Salt Targeting Methionine Metabolism," Nutrition and Cancer, Taylor & Francis (Routledge), vol. 0, No. 0, May 2017, pp. 1-11.

Jeong, K-Y et al., "Enhancing 5-Fluorouracil Efficacy in a Primary Colorectal Cancer by Long-lasting Calcium Supplementation," Anticancer Research, International Institute of Anticancer Research, vol. 37, Jun. 2017, pp. 2959-2964.

* cited by examiner

Table 1. Binding free energy of Metal-Lactate complexes

| | Metal (Hatree) | Lactate (Hatree) | Binding Energy ($\Delta E$, kcal/mol) | $T\Delta S$ (kcal/mol) | $\Delta G$ (kcal/mol) |
|---|---|---|---|---|---|
| $Na^+$-Lactate | -161.664286 | -341.163438 | -126.21 | -8.03 | -118.18 |
| $K^+$-Lactate | -599.001916 | -341.163438 | -106.85 | -7.06 | -99.79 |
| $Ca^{2+}$-Lactate | -676.13655 | -341.163438 | -290.86 | -8.20 | -282.66 |

HCT-116

HT-29

| SK-MEL2[BRAF-WT] | Average | CFR % | SD |
|---|---|---|---|
| Control | 167 | 100 | 18.52 |
| CaLa 1 mM | 90.7 | 53.8922 | 20.11 |
| CaLa 2.5 mM | 69.7 | 41.3174 | 8.5 |
| CaLa 5 mM | 49.7 | 29.3413 | 11.72 |

| SK-MEL28[BRAF-MT] | Average | CFR % | SD |
|---|---|---|---|
| Control | 105.3 | 100.3 | 10.97 |
| CaLa 1 mM | 75.7 | 72.1 | 3.51 |
| CaLa 2.5 mM | 65.3 | 62.2 | 5.51 |
| CaLa 5 mM | 0.0 | 0.0 | 0.00 |

P.O: peroral

I.T: intra tumoral

* Gastrointestinal stromal tumors

• Gastrointestinal stromal tumors

• Colorectal and oesophageal cancers

• Ovarian cancer, Breast cancer, Lung cancer cancer

• Non-small-cell lung carcinoma

• Renal cell carcinoma, Hepatocellular carcinoma, Thyroid cancer.

• Colorectal cancer

* Non-small cell lung cancer

• Renal cell carcinoma, gastrointestinal stromal tumor

- Breast, lung cancer

* Ovarian carcinoma, lung, head and neck cancers

* Breast, lung, and ovarian cancer

• Breast cancer

* Colorectal cancer ns022 B2

SEQUENCE LISTING

<160> NUMBER OF SEQ ID NOS: 4

<210> SEQ ID NO 1
<211> LENGTH: 19

```
<212> TYPE: DNA
<213> ORGANISM: Artificial Sequence
<220> FEATURE:
<223> OTHER INFORMATION: primer

<400> SEQUENCE: 1
aaaatggcag tgcgtttag                                              19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tttgaaggca gtctgtcgta                                             20

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
aactggaacg gtgaaggt                                               18

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cctgtaacaa cgcatctcat                                             20
```

PHARMACEUTICAL COMPOSITION FOR TREATING CANCER, CONTAINING LACTATE METAL SALT

REFERENCE TO A SEQUENCE LISTING SUBMITTED ELECTRONICALLY VIA EFS-WEB

The content of the electronically submitted sequence listing (Name: 19097-0030003_ST.txt; Size: 1,154 bytes; and Date of Creation: Jun. 9, 2017) is incorporated by reference in its entirety.

TECHNICAL FIELD

The present disclosure relates to a pharmaceutical composition for treating cancer including metal lactate salts, and more particularly, to a pharmaceutical composition for treating cancer including, as active ingredients, metal lactate salts capable of dissociating lactate, which can disturb metabolism of cancer cells and thus effectively inhibit activities such as growth, invasion, and metastasis of the cancer cells, within the cancer cells, a pharmaceutical composition for inhibiting cancer metastasis, and a food composition for improving cancer.

BACKGROUND

According to the data released in 2011, a total of 218,017 cancer cases were reported to have occurred in South Korea in 2011. The crude incidence rates were 439.2 for male and 431.0 for female per 100,000 people. The order of incidence of cancer was stomach, colorectal, lung, liver, and breast cancer. The top 5 cancers describe above have more than 50% incidence rate of all cancers. The most common cancers for male were stomach, colorectal, lung, and liver cancer in sequence, and for female were breast, colorectal, stomach, and lung cancer except thyroid cancer. If South Korean people live to the average life expectancy, the chance of getting cancer will be 36.9%. It is assumed that 2 out of 5 males (38.1%) and 1 out of 3 females (33.8%) are likely to develop cancer. The age-standardized rate (ASR) in South Korea adjusted by world standard population was 295.1 per 100,000 people, which is lower than the figure for the U.S. (318.0) or Australia (323.0) but higher than the OECD average (271.5). According to the data from National Statistical Office, the number of deaths caused by cancer was 75,334 people in South Korea in 2013, accounting for 28.3% of total deaths, and it is expected that the death rate from cancer will increase by 8.8% over the 2 to 3 years. Therefore, in order to treat cancer with a high incidence and death rate, various methods of treatment are being attempted around the world. So far, surgery and anticancer drug therapy or radiation therapy are the best choices to treat the early and advanced stage cancer aggressively.

For surgical treatment of cancer, the class and type of tumor should be identified through the diagnosis of tumor. In most cases, a biopsy is performed for diagnosis. Surgery is the radical treatment that all of lymph nodes surrounding the tumor and primary lesions are removed, using the radical exeresis. The radical exeresis is preferentially conducted with the goal of complete recovery. The death rate due to exeresis has decreased to 1 to 3%, and the 5-year survival rate of patients has increased by more than 50%. However, it is well known that patients who underwent surgery have a risk of relapse. Further, the surgery may have acute side effects such as bleeding, intestinal obstruction, vascular injury, ureteral injury, rectal rupture, pneumonia, and pulmonary embolism caused by complications, and, thus, a reoperation may be needed. Chemotherapy is the treatment of disease using drugs, i.e., anticancer drugs, applied to cancer cells spread in the entire body. However, most of the anticancer drugs are prepared to suppress rapid growth of cancer cells and thus will cause damage to cancer cells and possibly also to normal cells to a lesser degree. Meanwhile normal cells, such as blood cells, epithelial cells of gastrointestinal tract including the oral cavity, hair cells, and reproductive cells that are rapidly divided or proliferated, are greatly affected, and, result in side effects such as anemia, hair loss, and genetopathy. In severe cases, the anticancer drugs may lower the function of the marrow and may cause infection within 2 to 3 weeks of treatment, leading to death from sepsis. Radiotherapy refers to the treatment of inducing apoptosis of cancer tissues with high energy radiation. This treatment is one of the methods that allows a patient to keep a normal life, but may cause damage to the normal skin in a local area as a side effect of high energy radiation. In cases of metastatic cancer, the cancer stem cells may be resistant to radiation and relapse or metastasis may occur.

In order to overcome these disadvantages, studies for developing a treatment method of combining radiotherapy with chemotherapy or gene therapy are actively conducted. For example, Korean Patent Laid-open Publication No. 2002-0042606 discloses a radiosensitizer composition containing an N-acetylphytosphingosine derivative and a dimethylphytosphingosine derivative, Korean Patent Laid-open Publication No. 2003-0055878 discloses a radiosensitizer containing ceramides and derivatives thereof and dimethylsphingosine which is a sphingosine kinase inhibitor, and Korean Patent No. 620751 discloses a composition for radiosensitization, containing paeonol and a pharmaceutically acceptable salt thereof as active ingredients. However, in cases of combining radiotherapy with the above-described anticancer drugs to improve therapeutic effects of the radiotherapy, toxicity of the anticancer drugs, such as inflammation at the radiation therapy site, gastric disorder, nausea, vomiting, and diarrhea, may occur in addition to the side effects of the radiotherapy. Thus, the use of anticancer drugs is limited. Furthermore, it is known that due to the immunosuppressive environment, tumor cannot be completely exterminated and the risk of relapse is high.

Accordingly, the development of a novel treatment that is easily applicable to treat cancer and capable of effectively treating cancer with less influence on normal tissues is urgently needed. According to results from recent studies, it is known that a cancer cell has its own characteristics and can continuously grow while maintaining the characteristics. Firstly, a cancer cell has a characteristic of continuously maintaining a differentiation signal. For example, cell differentiation and survival by maintaining a β-catenin signaling is well known. A normal cell inhibits overproduction of the β-catenin signaling through protein ubiquitination, whereas a cancer cell avoids β-catenin ubiquitination and continuously maintains a growth signal. Secondly, a cancer cell has a system for producing an excessive amount of lactic acid through glycolysis using glucose to produce energy with high efficiency. Thirdly, a cancer cell has a characteristic of avoiding apoptosis. By activating poly ADP ribose polymerase (PARP), an apoptosis escaping molecule, a cancer cell avoids apoptosis with a resistance to various gene-targeted treatments and continuously maintains tumor formation. Fourthly, cancer is excellent in invasion or metastasis and also capable of creating its own environment by angiogenesis. If cancer grows continuously, necrosis occurs around tumor and the oxygen supply is reduced causing the increase of hypoxia inducible factor (HIF)-1α that is known to involve the above phenomenon directly or indirectly.

Targeting the above-described characteristics of cancer, various anticancer drugs have been developed based on regulation of cell growth and metastasis suppression. However, tyrosine kinase inhibitors mediating growth signals have shown unsatisfactory treatment results and resistance to drugs. In the development of anticancer drugs, it is still difficult to find a method to effectively suppress growth of cancer cells regulated by a network of complicated signaling pathways.

Under these circumstances, the inventors of the present disclosure studied and tried to develop a method to effectively suppress growth of cancer cells and treating cancer and as a result, completed the present disclosure by finding out that metal lactate salts capable of dissociating lactate, which can disturb metabolism of cancer cells and thus effectively inhibit activities such as growth, invasion, and metastasis of the cancer cells within the cancer cells, can be used as active ingredients of an anticancer drug.

SUMMARY

The present disclosure has been made in an effort to provide a pharmaceutical composition for treating cancer including metal lactate salts as active ingredients.

Further, the present disclosure has been made in an effort to provide a pharmaceutical composition for suppressing metastasis of cancer including metal lactate salts as active ingredients.

Furthermore, the present disclosure has been made in an effort to provide a food composition for improving cancer including metal lactate salts as active ingredients.

Furthermore, the present disclosure has been made in an effort to provide a method for treating cancer comprising administering metal lactate salts.

Furthermore, the present disclosure has been made in an effort to provide a method for suppressing metastasis of cancer comprising administering metal lactate salts.

According to exemplary embodiments of the present disclosure, the metal lactate salts of the present disclosure have no side effects and disturb metabolism in a main energy production pathway to suppress the growth of cancer cells, induce apoptosis and also suppress expression of a factor that induces resistance to radiation, and, thus, can be widely used for more effective anticancer treatment.

Figure 5:
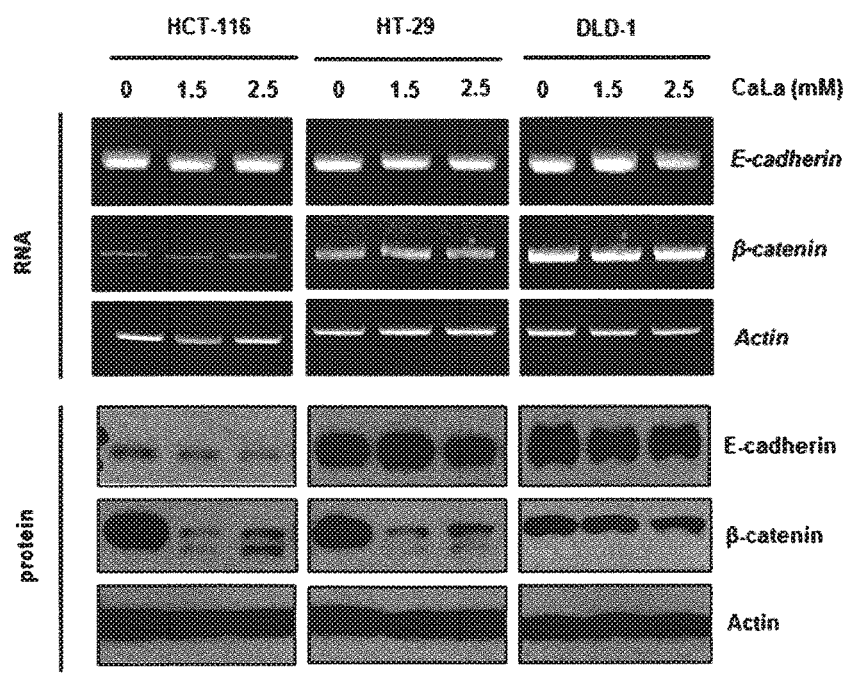

The upper part of FIG. 5 provides electrophoretic images showing the result of comparing mRNA expression levels of β-catenin in human colorectal cancer cell lines (HCT-116, HT-29, and DLD-1) treated with calcium lactate at various concentrations, and the lower part of FIG. 5 provides Western blotting images showing the result of comparing protein expression levels of β-catenin in human colorectal cancer cell lines (HCT-116, HT-29, and DLD-1) treated with calcium lactate at various concentrations.

Figure 6:
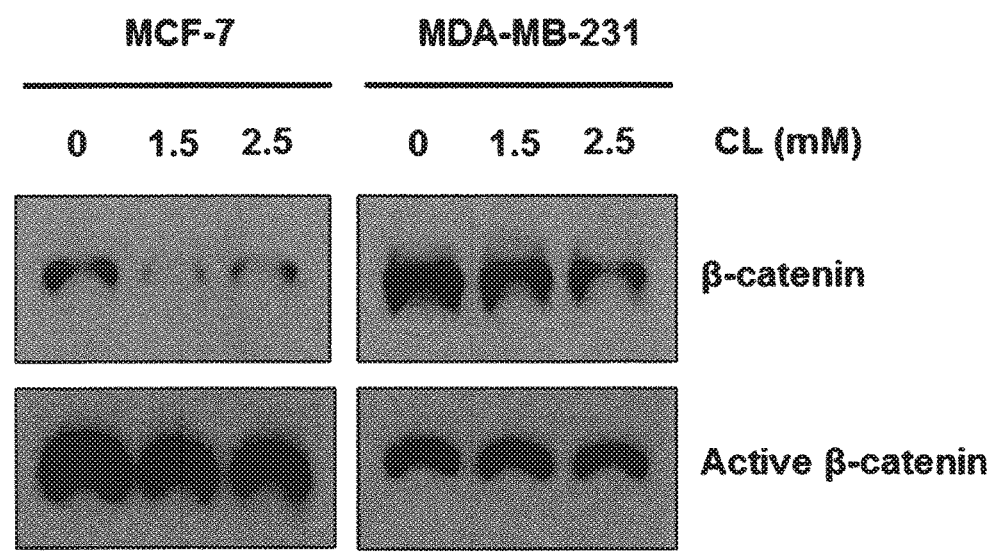

FIG. 6 provides Western blotting images showing the result of comparing protein expression levels of the total β-catenin and activated β-catenin in human breast cancer cell lines (MCF-7 and MDA-MB-231) treated with calcium lactate at various concentrations.

Figure 7:
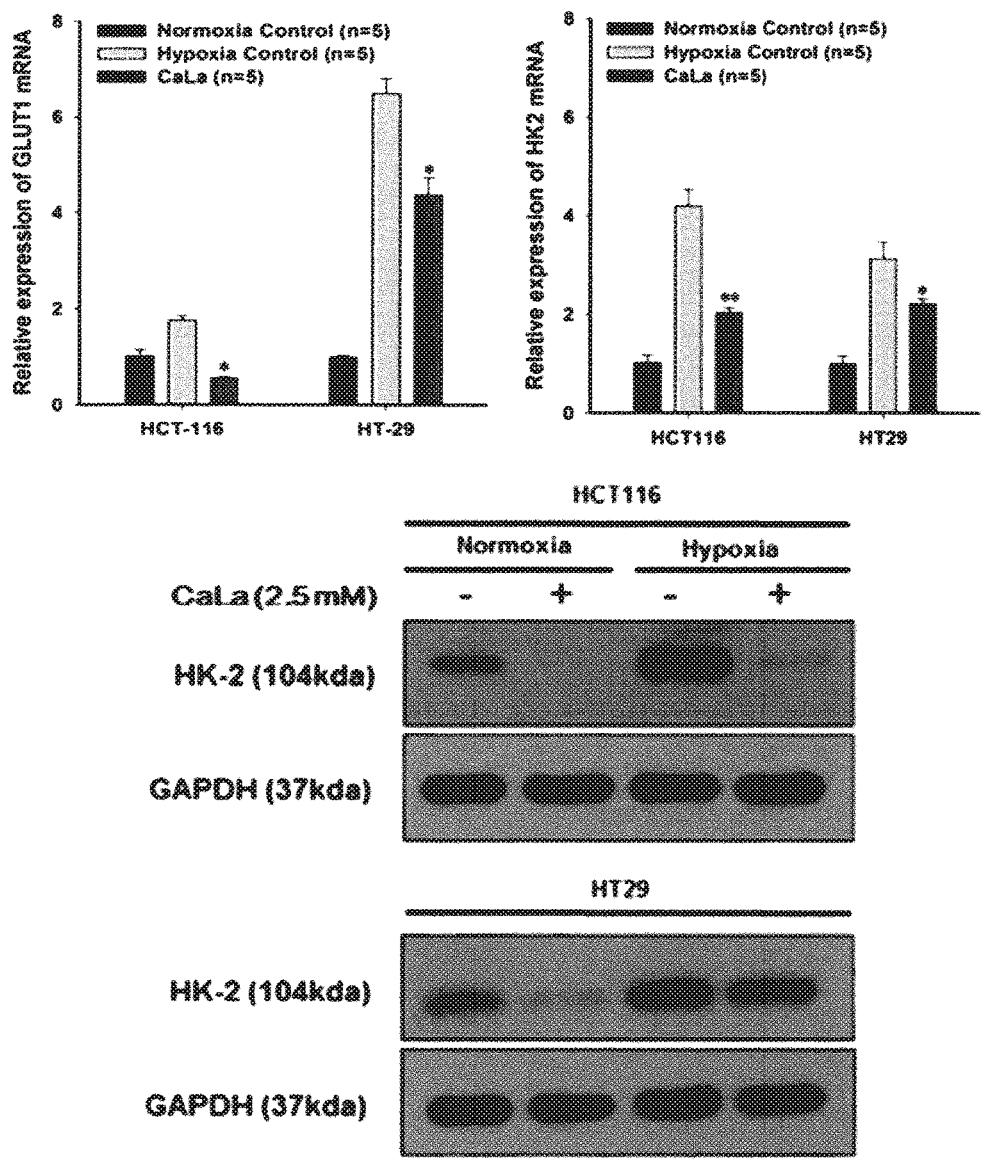

FIG. 7 is a real-time PCR and a western blot shows the effect of calcium lactate in the cancer cell line under hypoxic conditions. The graph shows mRNA expression levels of glucose transporter (GLUT)-1 and hexokinase (HK)2, which involved in the early stage of glycolysis and western blotting images showing protein expression levels of HK2.

Figure 8:
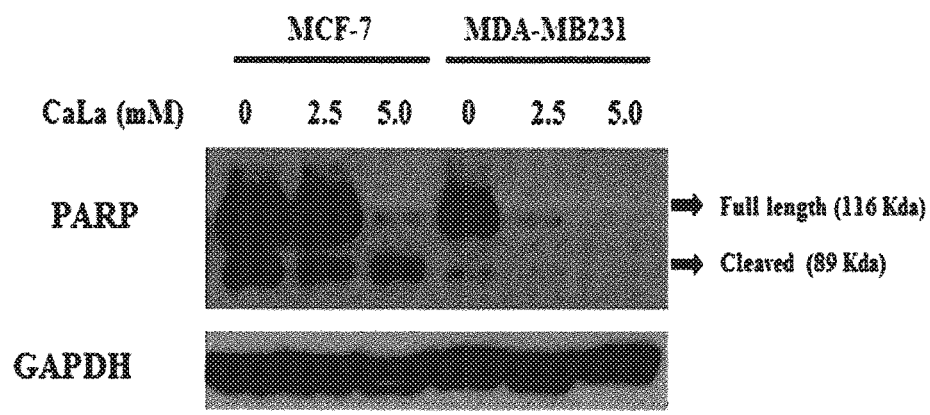

FIG. 8 provides Western blotting images showing the effects of calcium lactate on protein expression levels of PARP and cleaved PARP expressed in human breast cancer cell lines (MCF-7 and MDA-MB-231).

Figure 9:
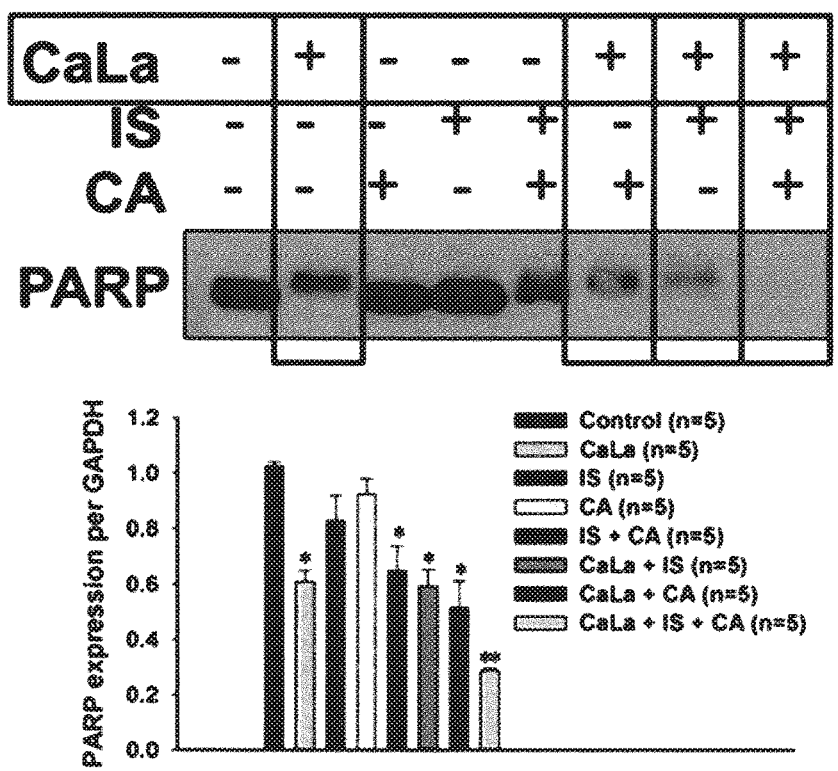

FIG. 9 provides a Western blotting image and a graph showing the result of comparing protein expression levels of PARP in colorectal cancer cell lines treated with calcium lactate, 5-indane sulfonamide (IS) as an inhibitor of carbonic anhydrase, or cinnamic acid (CA) as an inhibitor of MCT-4, which is a pathway of lactate outflow, individually or in combination.

Figure 10:
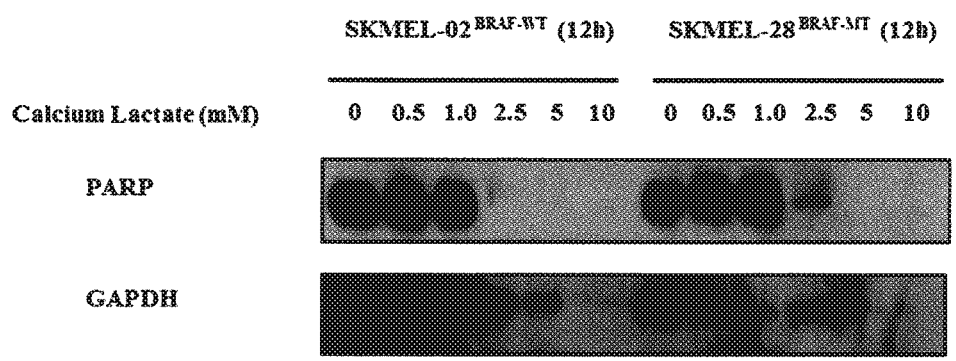

FIG. 10 provides Western blotting images showing the result of comparing protein expression levels of PARP in human melanoma cell lines (SKMEL-02 and SKMEL-28) treated with calcium lactate at various concentrations.

Figure 11A:
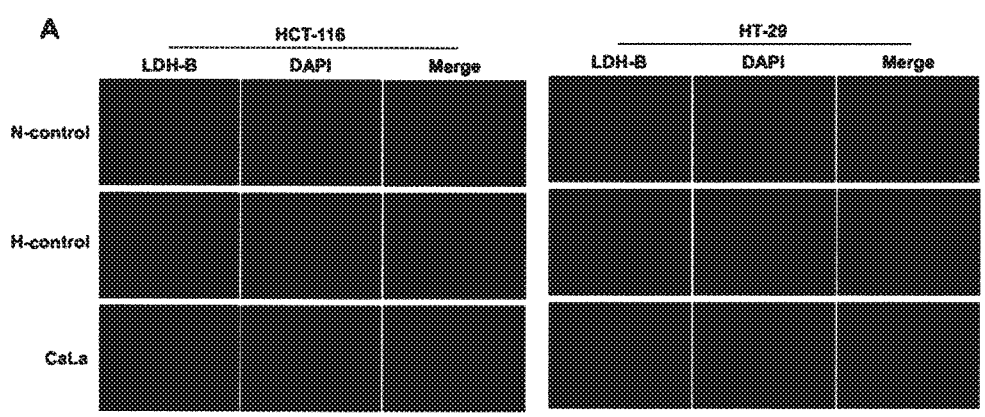
Figure 11B:
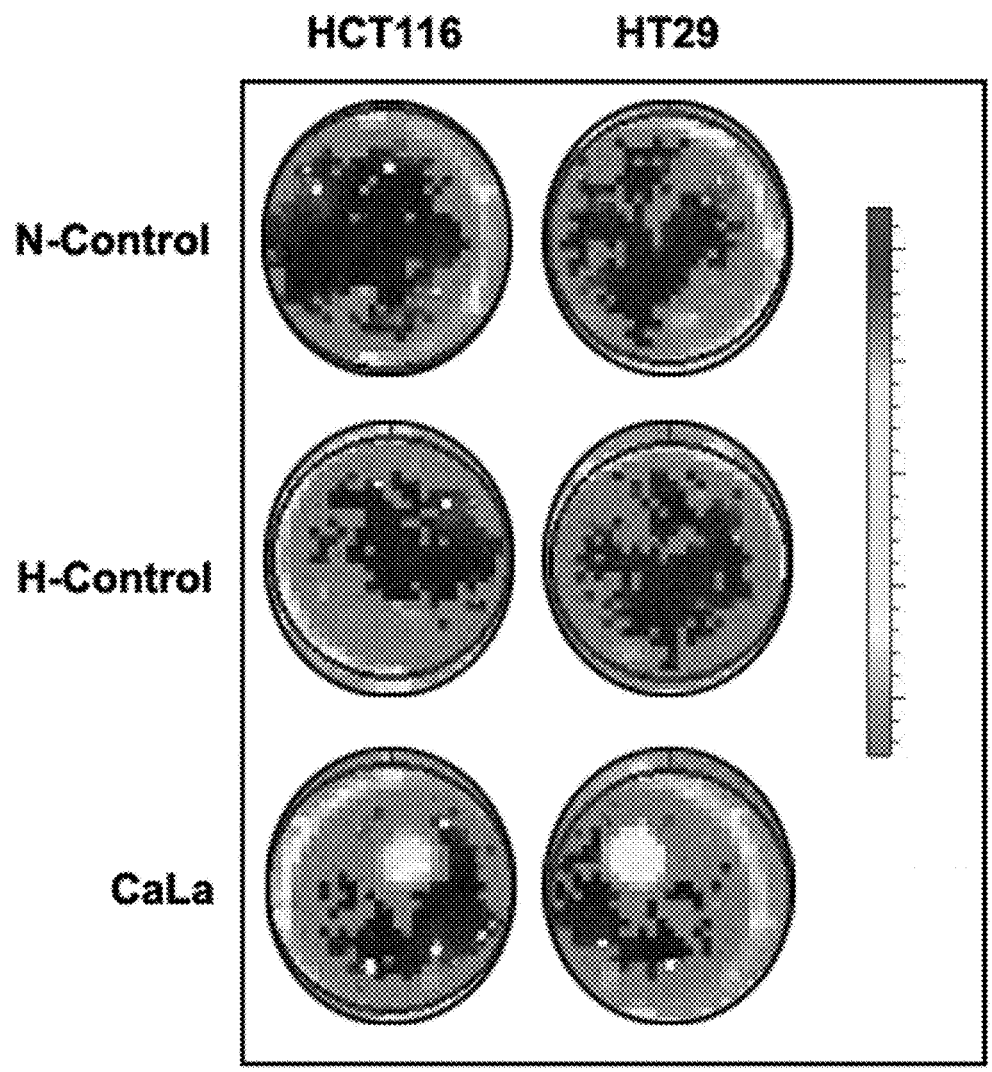
Figure 11C:
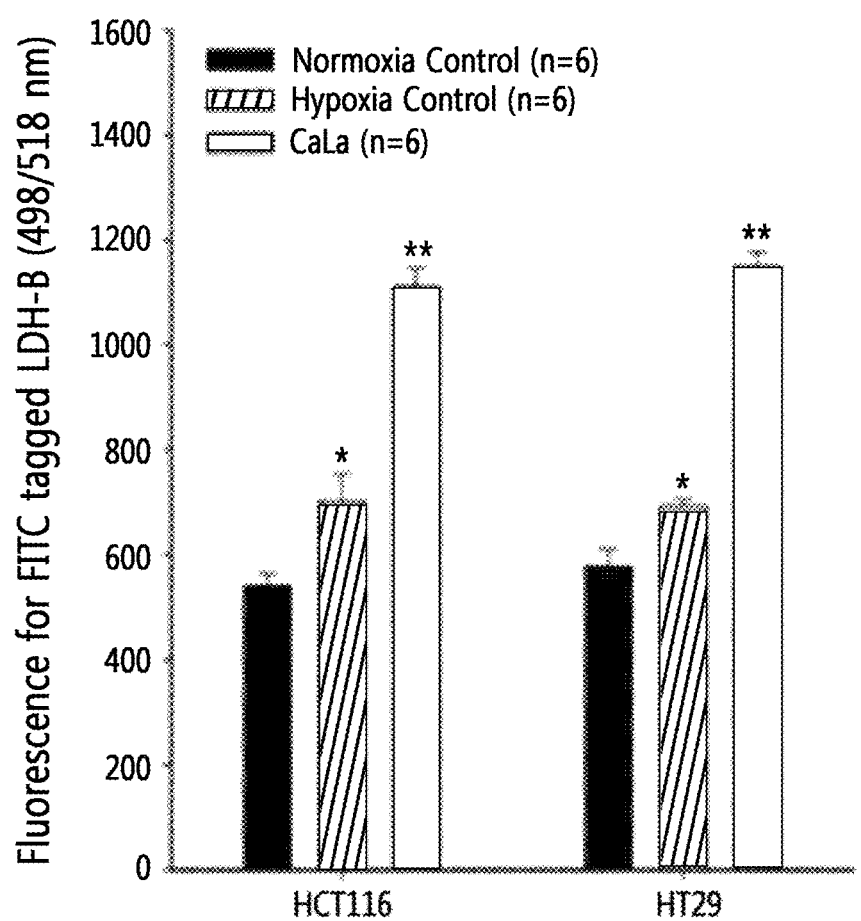

FIG. 11a provides fluorescence microscope images showing the changes in protein expression levels of LDH-B in cancer cell lines depending on the treatment with calcium lactate. FIG. 11b provides fluorescence microscope images showing the fluorescence absorbance of cancer cell line depending on the treatment with calcium lactate. FIG. 11c provides quantitative analysis graph showing fluorescence development levels depending on the protein expression levels of LDH-B.

Figure 12:
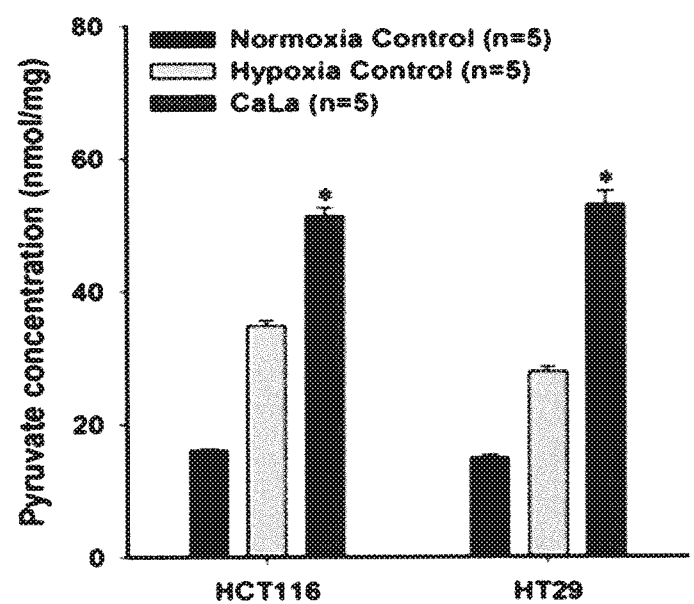

FIG. 12 is a graph showing changes of pyruvate concentrations in cancer cells depending on the treatment with calcium lactate.

Figure 13A:
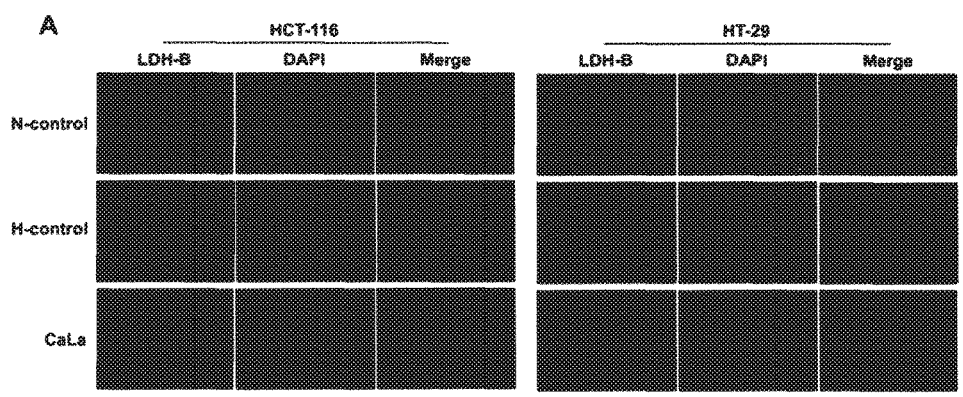
Figure 13B:
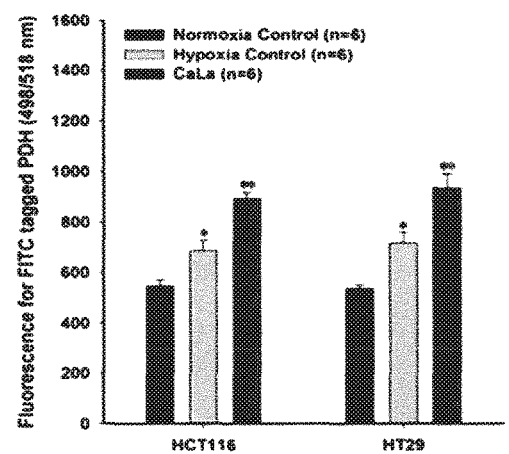

FIG. 13a provides fluorescence microscope images showing changes in protein expression levels of PDH in cancer cell lines depending on the treatment with calcium lactate. FIG. 13b provides a quantitative analysis graph showing fluorescence development levels of PDH depending on the treatment with calcium lactate.

Figure 14A:
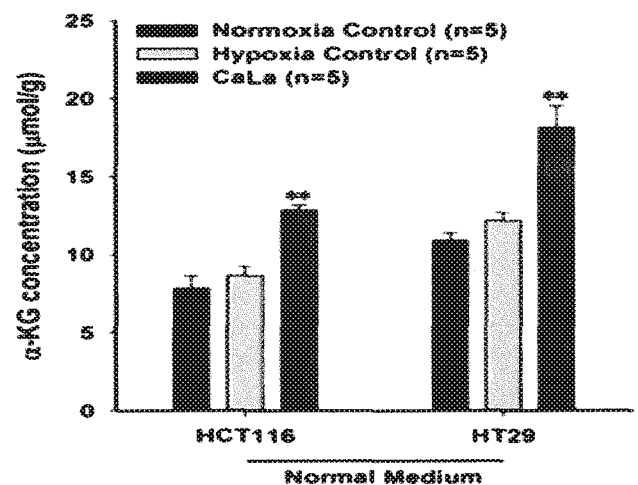
Figure 14B:
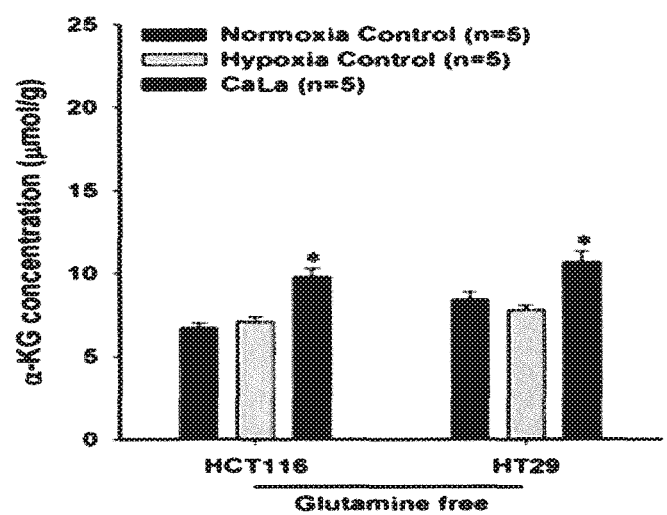

FIG. 14a provides a quantitative analysis graphs showing the changes in concentration of α-KG in cancer cell lines with calcium lactate treatment under normal medium. FIG. 14b provides a quantitative analysis graph showing the changes in concentration of α-KG in cancer cell lines with calcium lactate treatment under glutamine-free medium.

Figure 15:
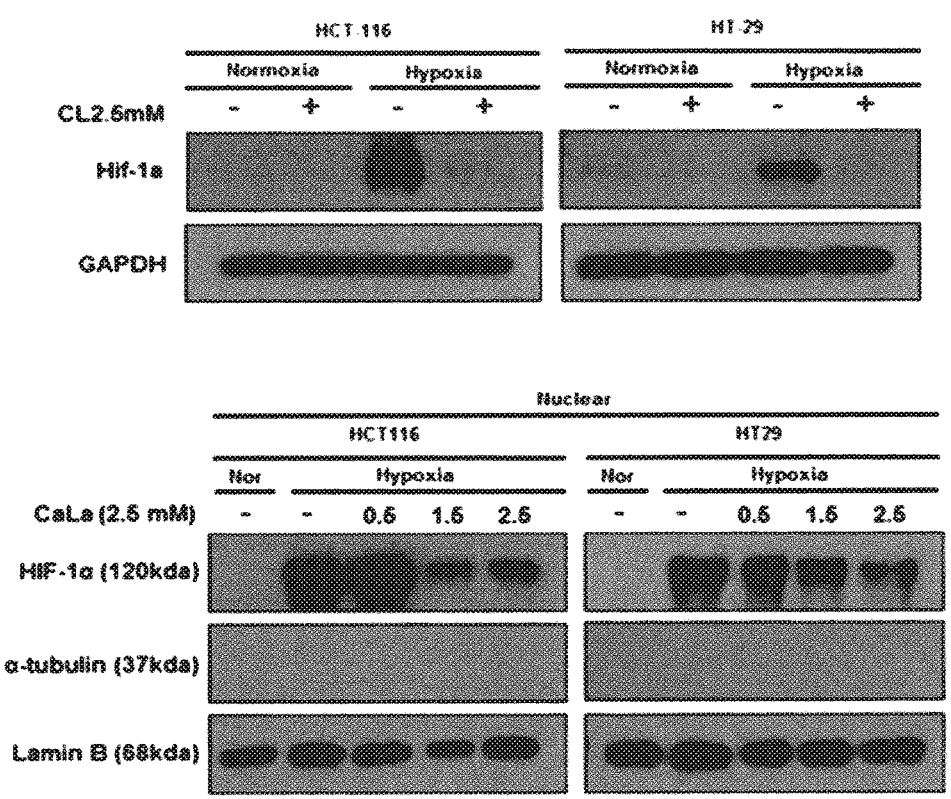

FIG. 15 (upper part) provides Western blotting images showing the expression levels of HIF-1α protein in human colorectal cancer cell lines (HCT-116 and HT-29) cultured for 24 hours with or without the treatment with 2.5 mM calcium lactate under normoxia or hypoxia condition, and the lower part of FIG. 15 provides Western blotting images showing the expression levels of HIF-1α protein in human colorectal cancer cell lines (HCT-116 and HT-29) cultured for 24 hours with 0.5 mM, 1.5 mM and 2.5 mM calcium lactate treatment under hypoxia condition.

Figure 16A:
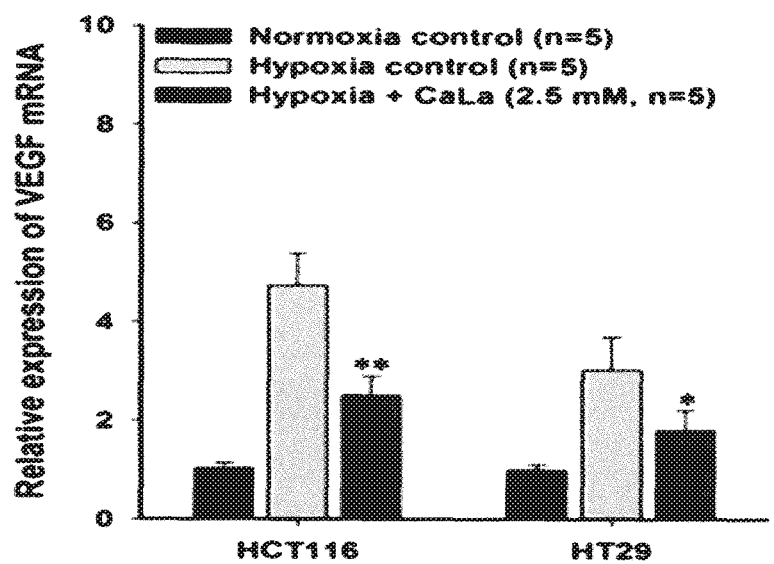
Figure 16B:
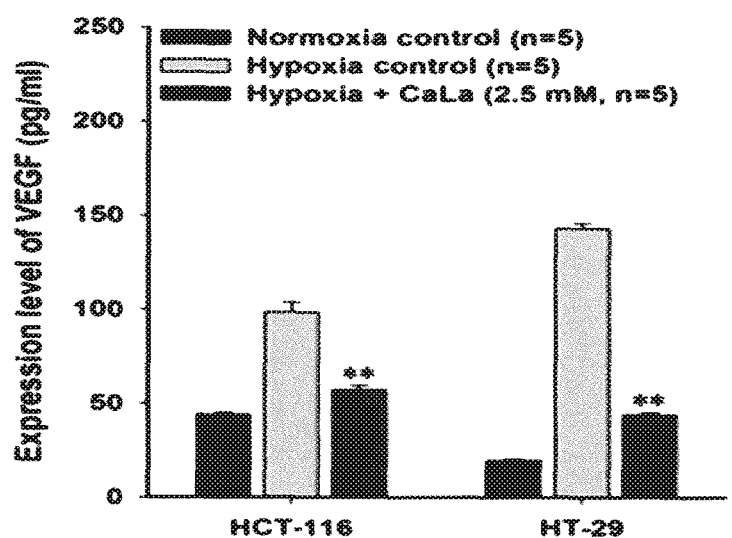

FIG. 16a provides quantitative analysis graphs showing the result of measuring the mRNA expression levels of VEGF in human colorectal cancer cell lines (HCT-116 and HT-29) cultured for 24 hours with or without the 2.5 mM calcium lactate under normoxia or hypoxia condition. FIG. 16b provides quantitative analysis graphs showing the result of measuring the protein expression levels of VEGF in human colorectal cancer cell lines (HCT-116 and HT-29) cultured for 24 hours with or without the 2.5 mM calcium lactate under normoxia or hypoxia condition.

Figure 17:
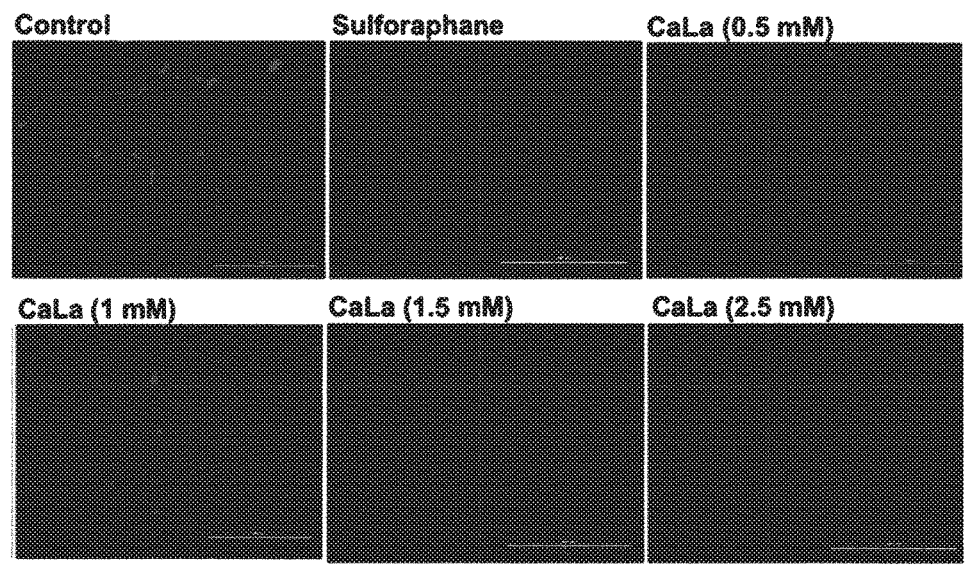

FIG. 17 is fluorescence images showing the tube formation levels in human vascular endothelial cells (HUVEC) treated with calcium lactate at various concentrations. The HUVEC was cultured using the medium of cultured cancer cell lines with different concentrations of calcium lactate.

Figure 18:
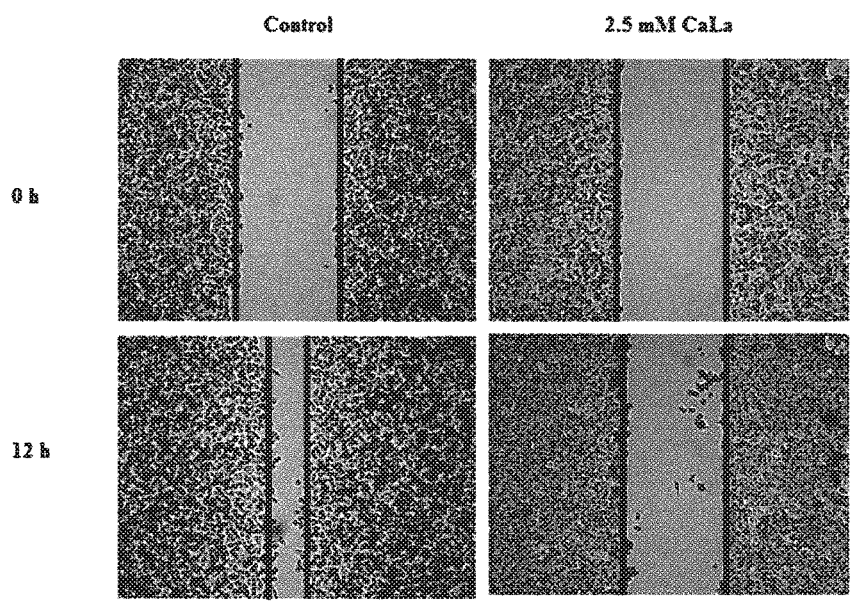

FIG. 18 provides photos showing the result confirming cell migration, which shows metastatic capacity of a colorectal cancer cell line, depending on whether or not treated with calcium lactate.

Figure 19:
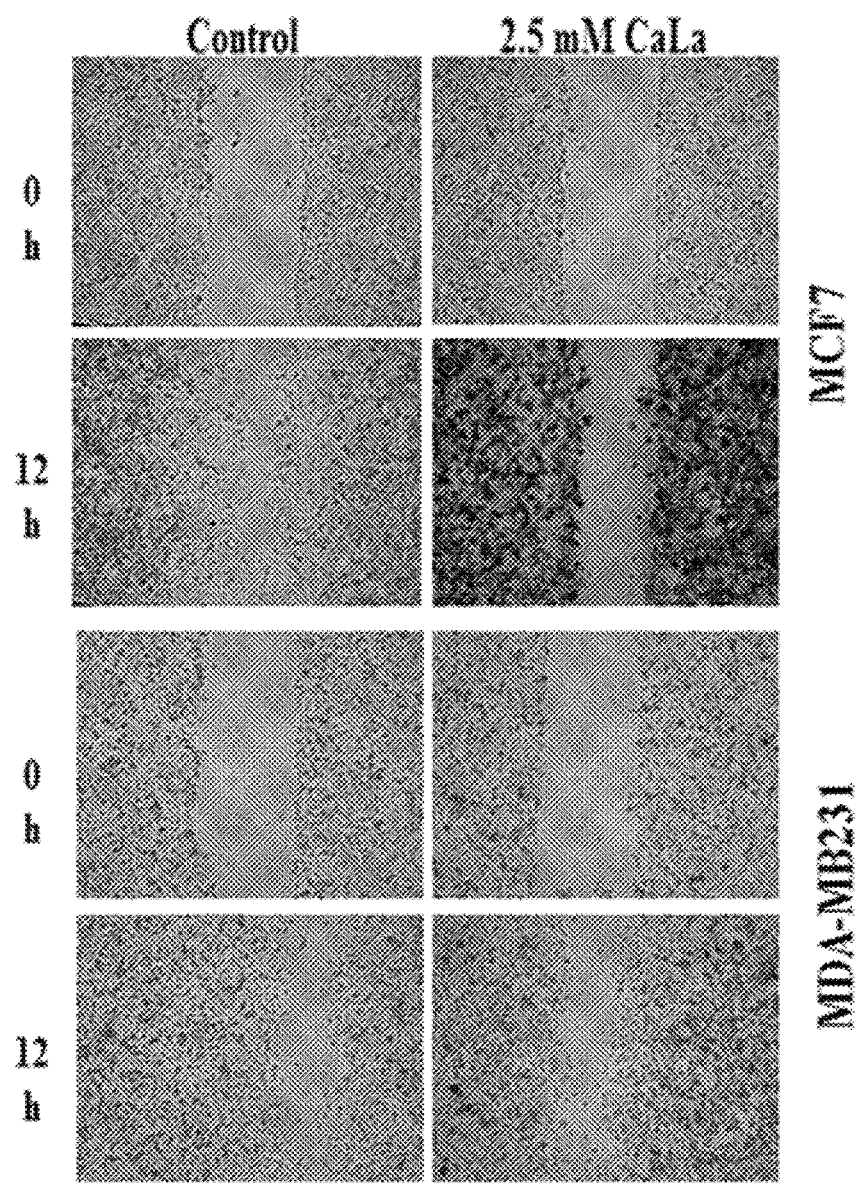

FIG. 19 provides photos showing the result confirming cell migration, which shows metastatic capacity of a breast cancer cell line, depending on whether or not treated with calcium lactate.

Figure 20:
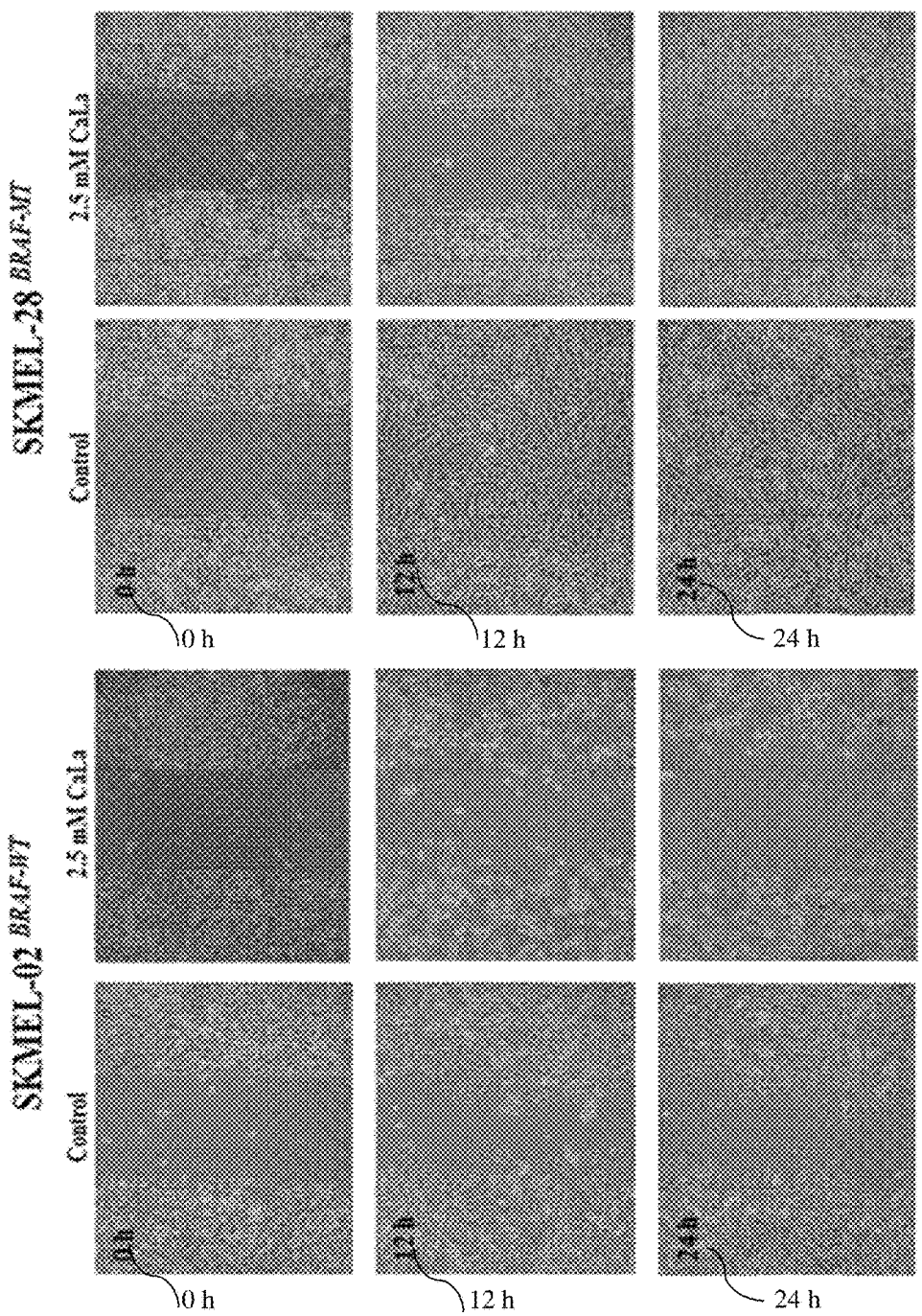

FIG. 20 provides photos showing the result confirming cell migration, which shows metastatic capacity of a melanoma cell line, depending on whether or not treated with calcium lactate.

Figure 21A:
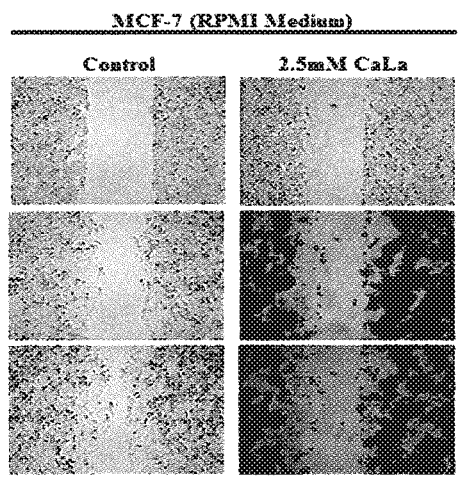
Figure 21B:
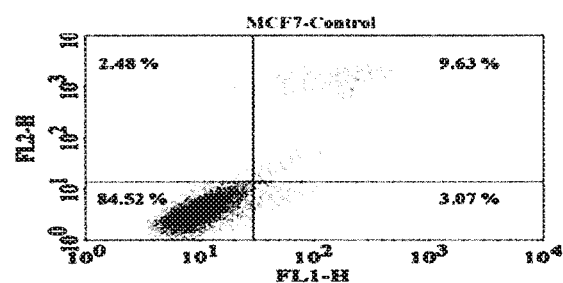
Figure 21C:
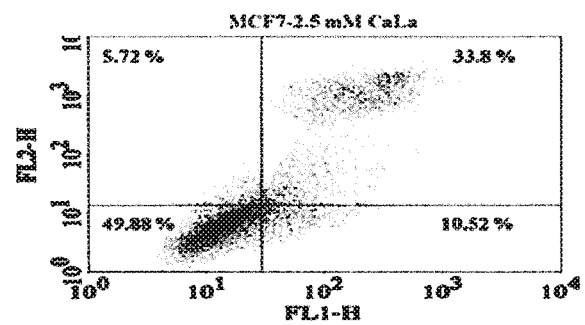
Figure 21D:
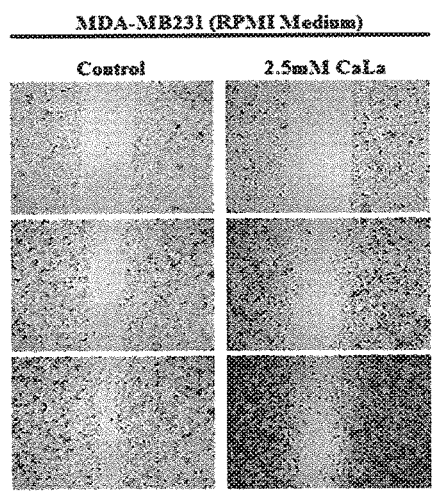
Figure 21E:
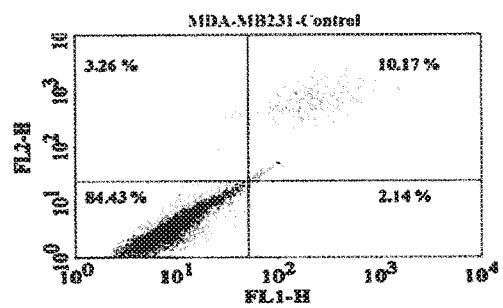
Figure 21F:
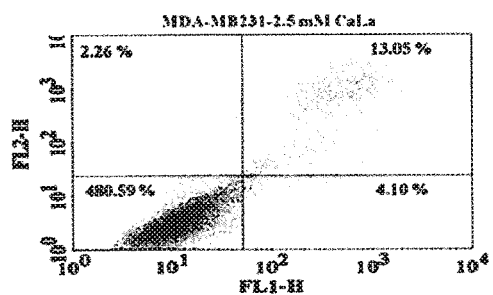

FIG. 21a provides photos showing the result confirming cell migration which shows metastatic capacity of a breast cancer cell line (MCF-7) depending on whether or not treated with calcium lactate. FIG. 21b provides flow cytometry analyses showing the survival rate of a breast cancer cell line (MCF-7) that was not treated with calcium lactate. FIG. 21c provides flow cytometry analyses showing the survival rate of a breast cancer cell line (MCF-7) that was treated with calcium lactate. FIG. 21d provides photos showing the result of confirming cell migration, which shows metastatic capacity of a breast cancer cell line (MDA-MB231) depending on whether or not treated with calcium lactate. FIG. 21e provides flow cytometry analyses showing the survival rate of a breast cancer cell line (MDA-MB231) that was not treated with calcium lactate. FIG. 21f provides flow cytometry analyses showing the survival rate of a breast cancer cell line (MDA-MB231) that was treated with calcium lactate.

Figure 22:
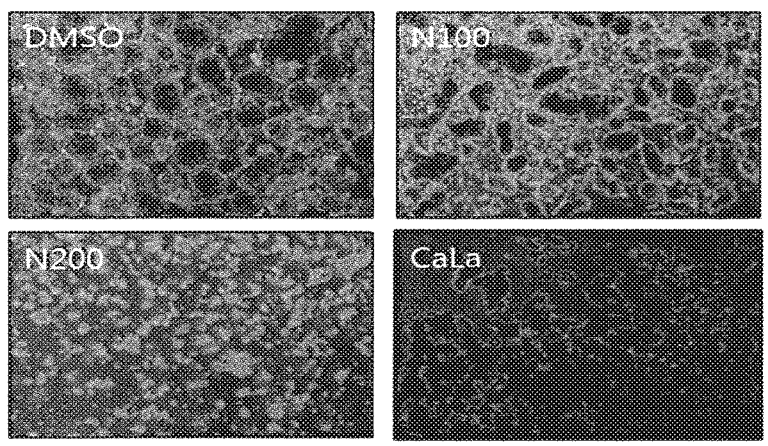

FIG. 22 provides microscopic images showing the sphere change of the colorectal cancer stem cell line from the treatment with calcium lactate.

Figure 23:
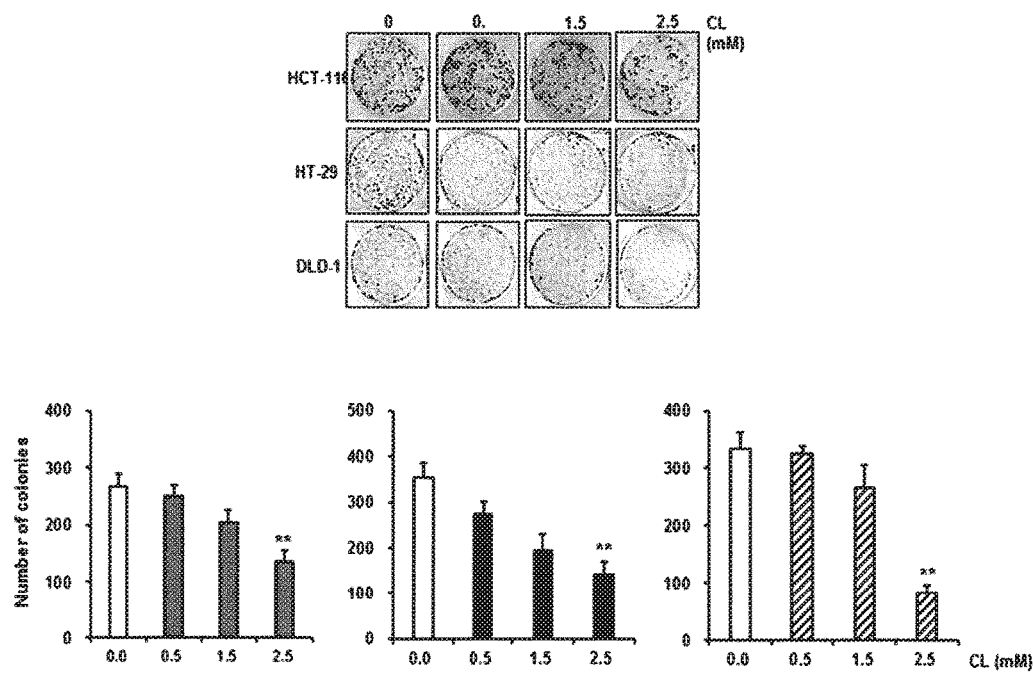

FIG. 23 provides representative pictures and quantitative analysis graphs (left: HCT-116, middle: HT-29, right: DLD-1) showing the comparison of a colony-forming ability of colorectal cancer cell lines depending on the concentration of calcium lactate.

Figure 24A:
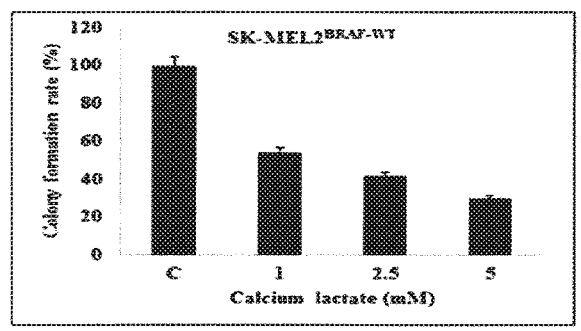
Figure 24B:
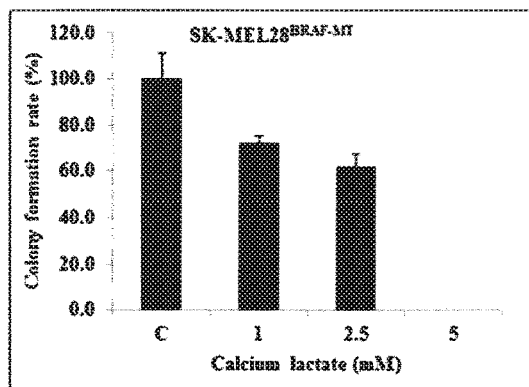

FIG. 24a provides graphs and tables showing the result of comparison of a colony-forming ability of melanoma cell lines SKMEL-02 depending on the concentration of calcium lactate. FIG. 24b provides graph and table showing the result of comparison of a colony-forming ability of melanoma cell lines SKMEL-28 depending on the concentration of calcium lactate.

Figure 25A:
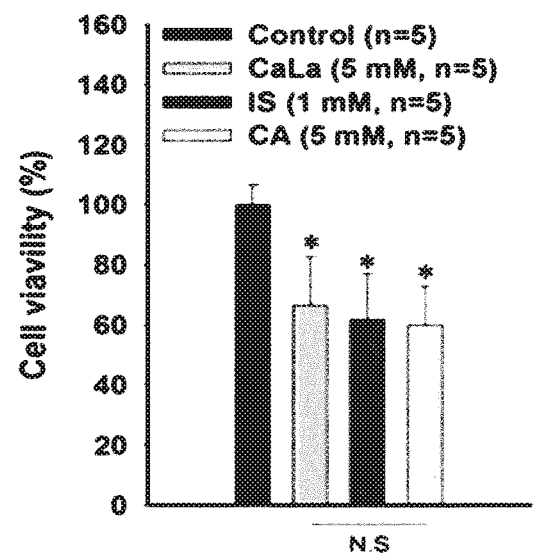
Figure 25B:
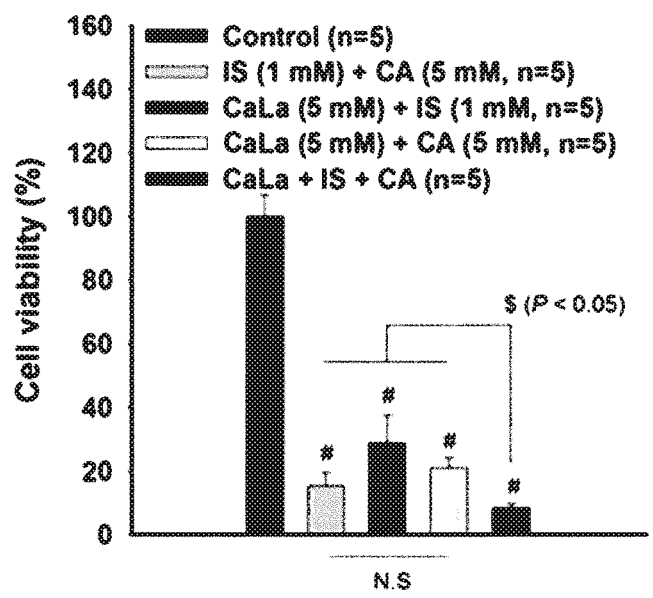

FIG. 25a provides quantitative analysis graphs showing the result of comparing the survival rate of colorectal cancer cell lines treated with calcium lactate, 5-indane sulfonamide (IS) as an inhibitor of carbonic anhydrase, or cinnamic acid (CA) as an inhibitor of MCT-4, which is a pathway of lactate outflow, individually. FIG. 25b provides quantitative analysis graph showing the result of comparing the viability rate of colorectal cancer cell lines treated with calcium lactate, 5-IS as an inhibitor of carbonic anhydrase, or CA as an inhibitor of MCT-4, which is a pathway of lactate outflow, in combination.

Figure 26:
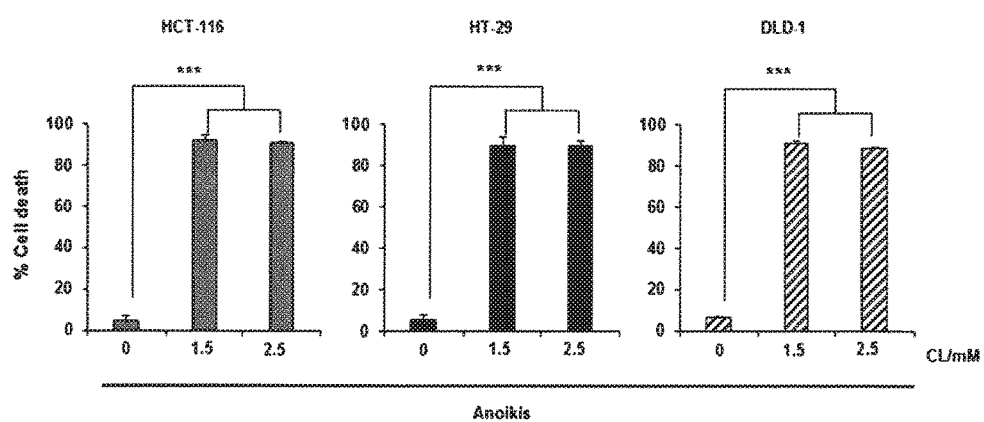

FIG. 26 provides quantitative analysis graphs showing the result of comparing the effects of calcium lactate on the survival rate of colorectal cancer cell lines cultured in the ultra-low adhesive plates.

Figure 27:
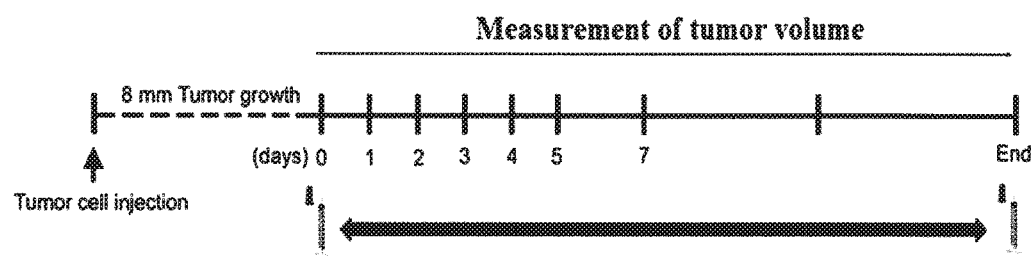

FIG. 27 is a schematic illustration of experimental scheme for calcium lactate treatment using animal models.

Figure 28:
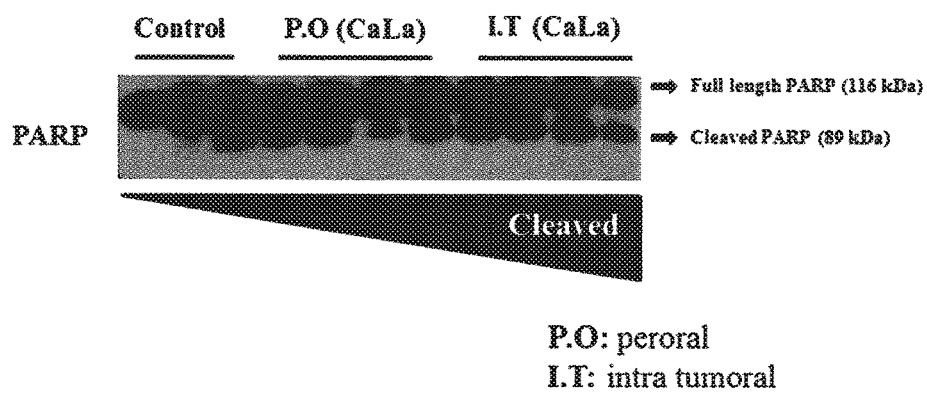

FIG. 28 is a picture showing the change in expression levels of PARP proteins extracted from the tumor tissue of the xenograft animal model depending on treatment method of calcium lactate, and whether or not treated with calcium lactate.

Figure 29:
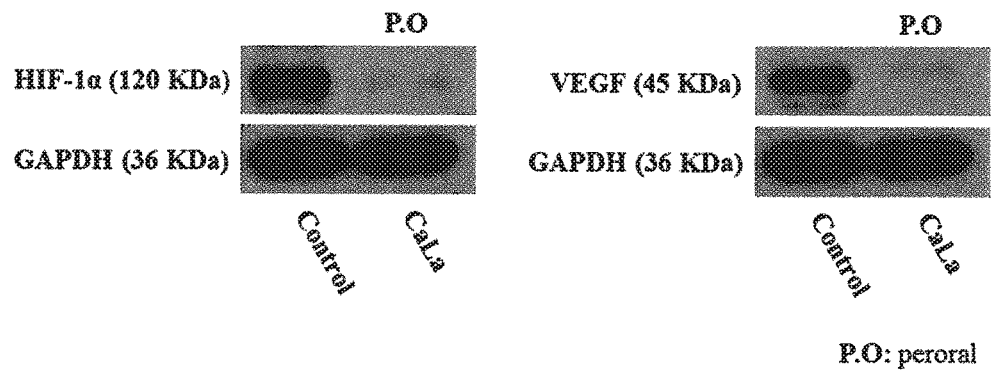

FIG. 29 provides photos showing the change in expression levels of HIF-1α or GAPDH depending on whether or not treated with calcium lactate, in proteins extracted from tumor tissues of the animal models in which calcium lactate was orally administered.

Figure 30:
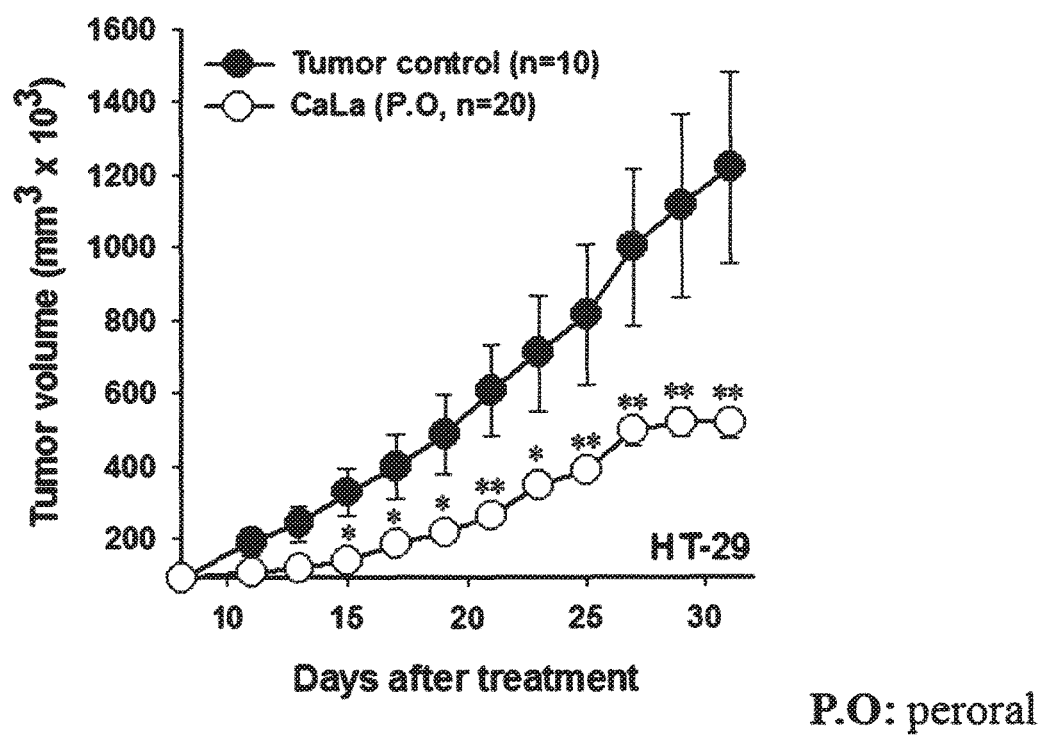

FIG. 30 provides a graph showing the change in tumor volume depending on whether or not treated with calcium lactate in an animal model in which 2.5 mM calcium lactate was orally administered.

Figure 31:
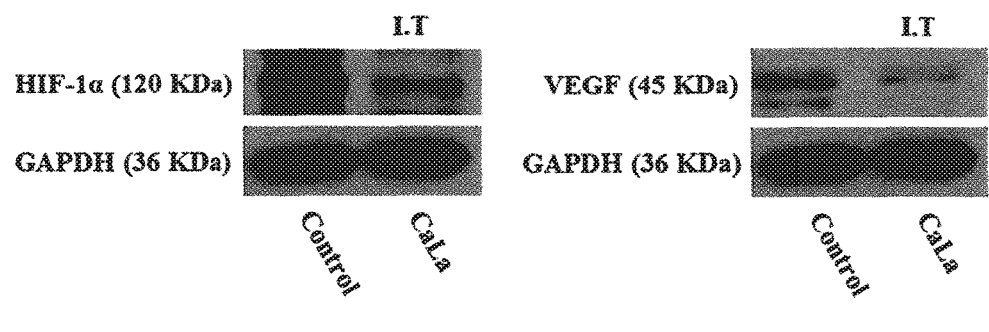

FIG. 31 provides western blots showing the change in the expression levels of HIF-1α or GAPDH in the protein extracted from tumor tissues of the xenograft animal model depending on whether or not treated with calcium lactate around the tumor.

Figure 32:
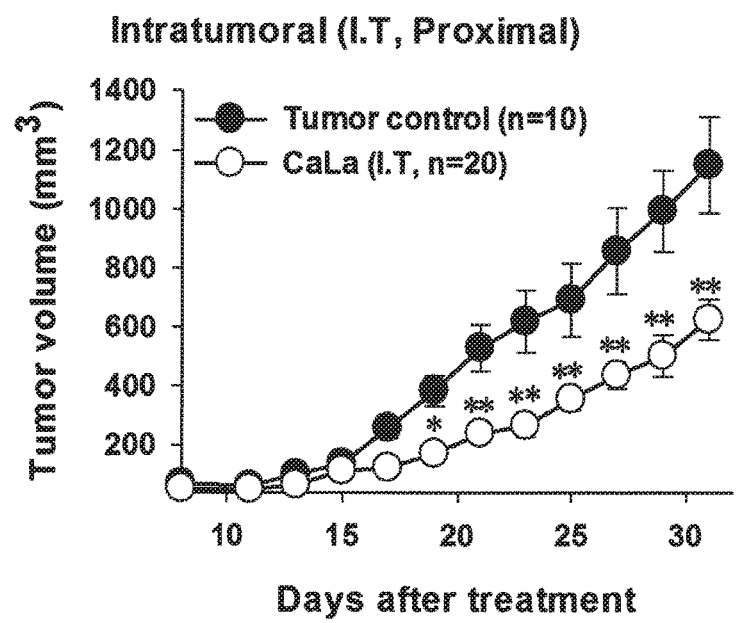

FIG. 32 provides a graph showing the change in tumor volume depending on whether or not treated with 2.5 mM calcium lactate around a tumor.

Figure 33:
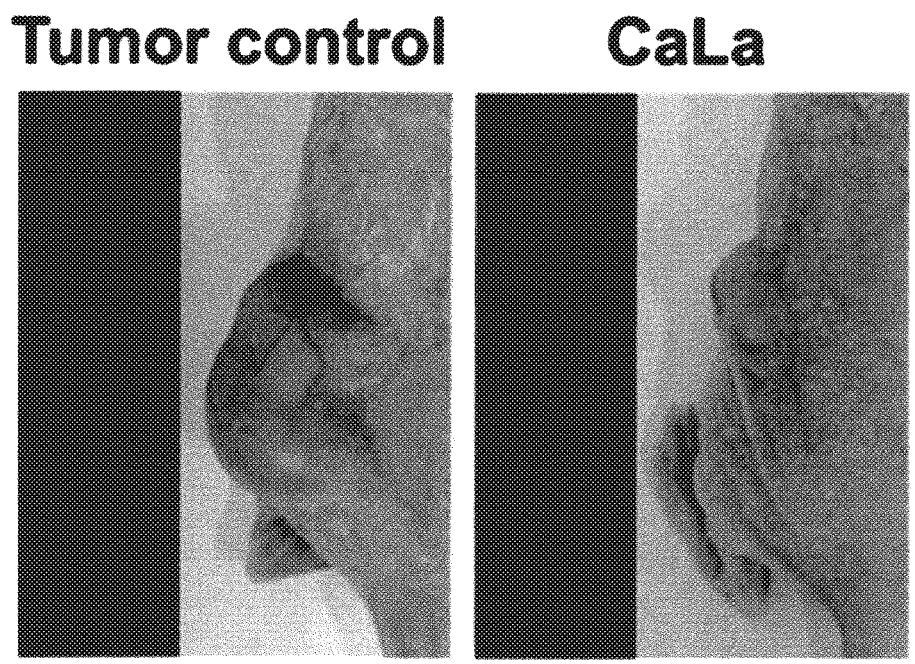

FIG. 33 provides representative pictures showing the change in tumor morphology of an animal model depending on the injection of 2.5 mM calcium lactate around a tumor.

Figure 34:
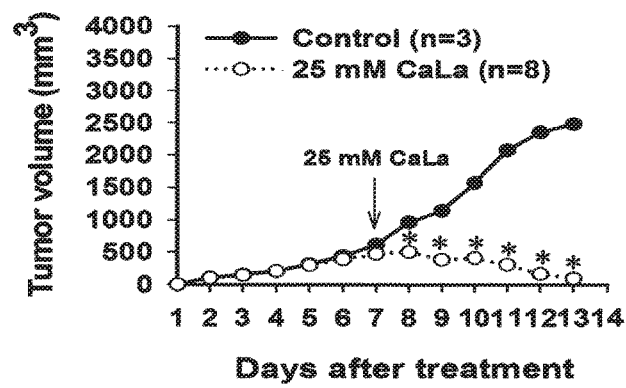

FIG. 34 provides a graph showing the change in tumor volume depending on whether or not treated with calcium lactate, in an animal model in which 25 mM calcium lactate was subcutaneously injected around the interscapular region.

Figure 35:
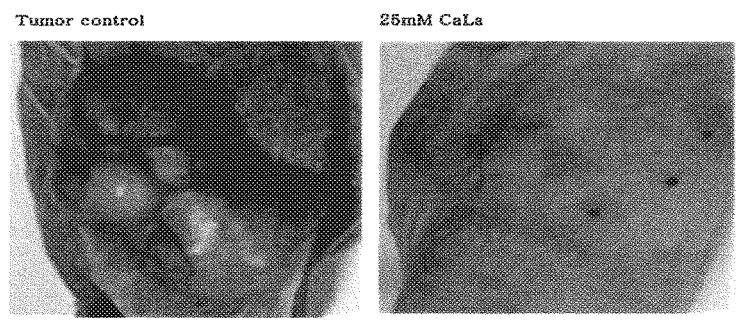

FIG. 35 provides representative pictures showing the change in tumor morphology in an animal model depending on the calcium lactate treatment.

Figure 36:
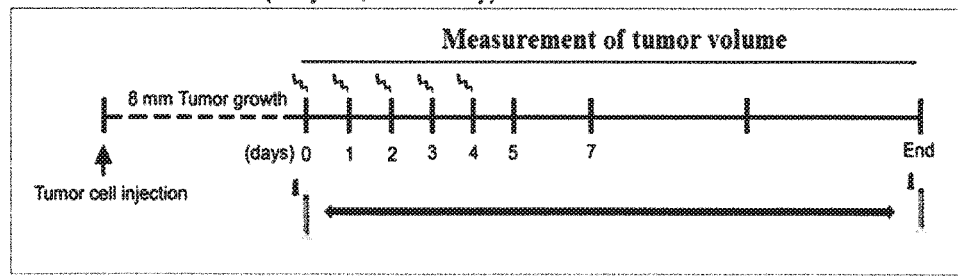

FIG. 36 is a schematic illustration of experimental scheme for the combination treatment with radiation and calcium lactate using animal models.

Figure 37A:
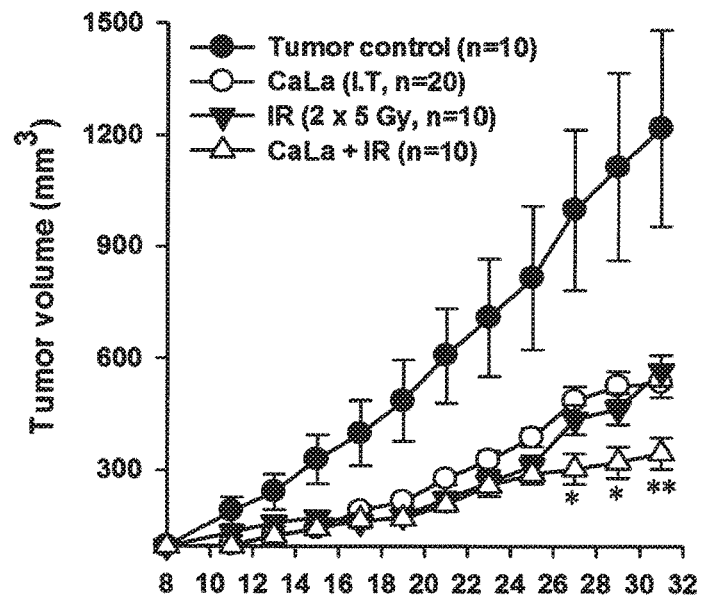
Figure 37B:
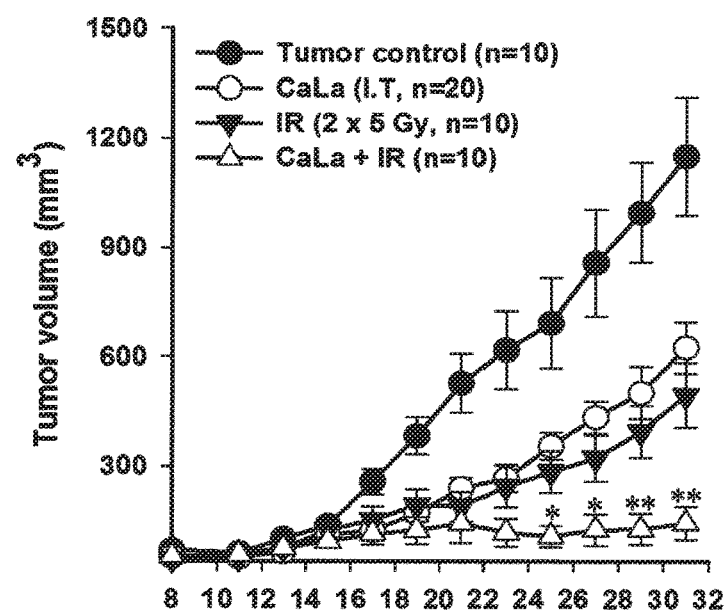

FIG. 37a provides a graph showing the change in tumor volume over time in an animal cancer model, which was prepared by implanting HT-29 colorectal cancer cell line into the flank depending on whether treated with radiation and calcium lactate individually or in combination. FIG. 37b provides a graph showing the change in tumor volume over time in an animal cancer model, which was prepared by implanting a HCT-116 colorectal cancer cell line into the flank depending on whether treated with radiation and calcium lactate individually or in combination.

Figure 38A:
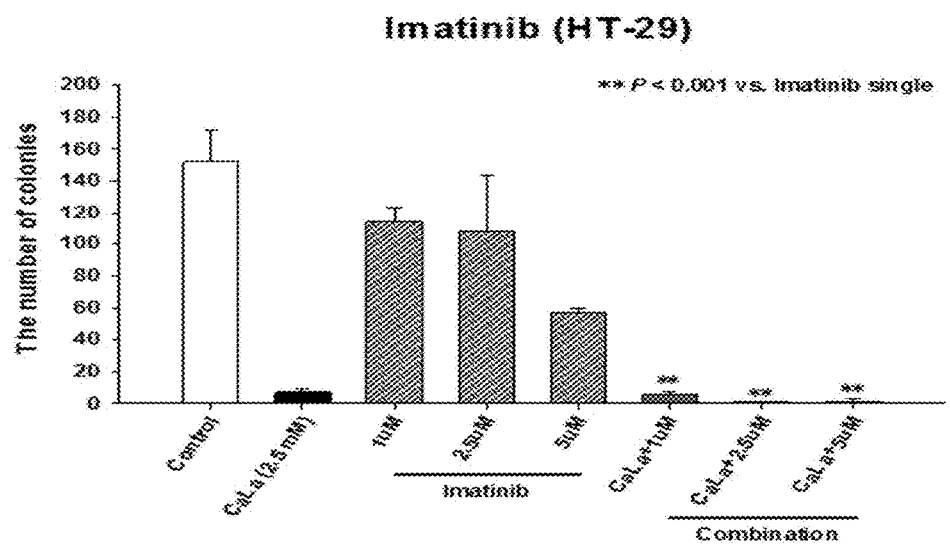
Figure 38B:
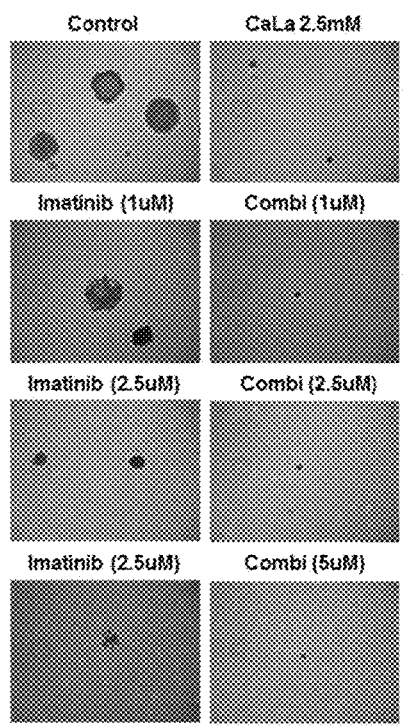

FIG. 38a shows the result of comparing the decrease in the number of colonies when a human colorectal cancer cell line (HT-29) was treated with 2.5 mM calcium lactate and 1 μM, 2.5 μM, and 5 μM Imatinib, alone or in combination. FIG. 38b shows the result of comparing the suppression of the formation of individual colony when a human colorectal cancer cell line (HT-29) was treated with 2.5 mM calcium lactate and 1 μM, 2.5 μM, and 5 μM Imatinib, alone or in combination.

Figure 39A:
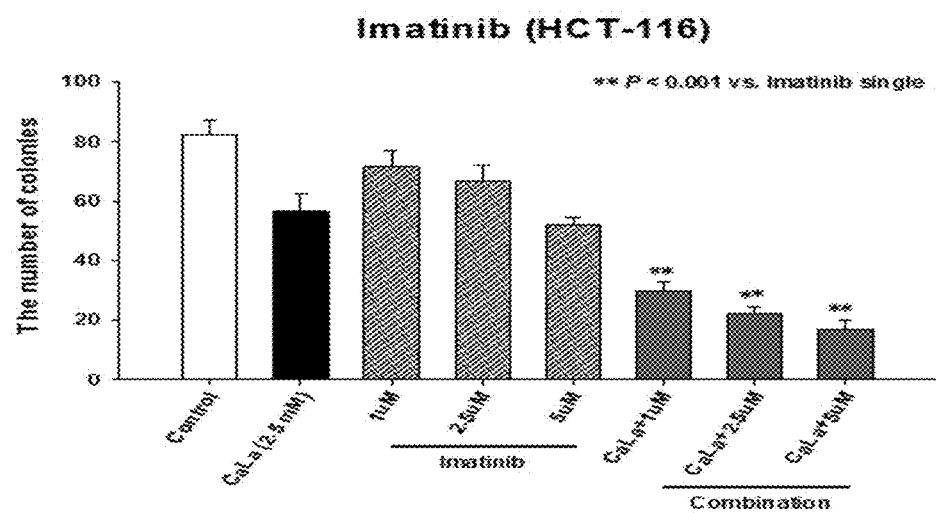
Figure 39B:
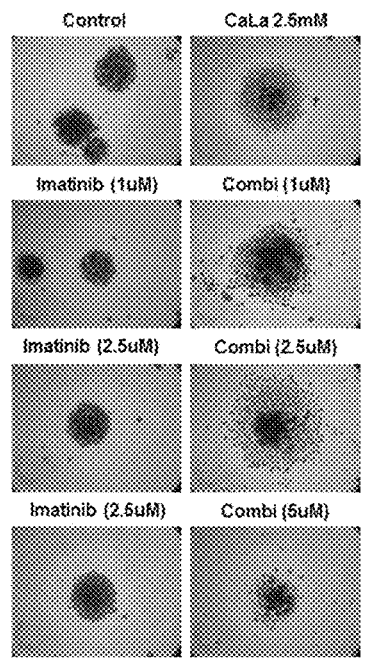

FIG. 39*a* shows the result of comparing the decrease in the number of colonies when a human colorectal cancer cell line (HCT-116) was treated with 2.5 mM calcium lactate and 1 μM, 2.5 μM, and 5 μM Imatinib, alone or in combination. FIG. 39*b* shows the result of comparing the suppression of the formation of individual colony when a human colorectal cancer cell line (HCT-116) was treated with 2.5 mM calcium lactate and 1 μM, 2.5 μM, and 5 μM Imatinib, alone or in combination.

Figure 40A:
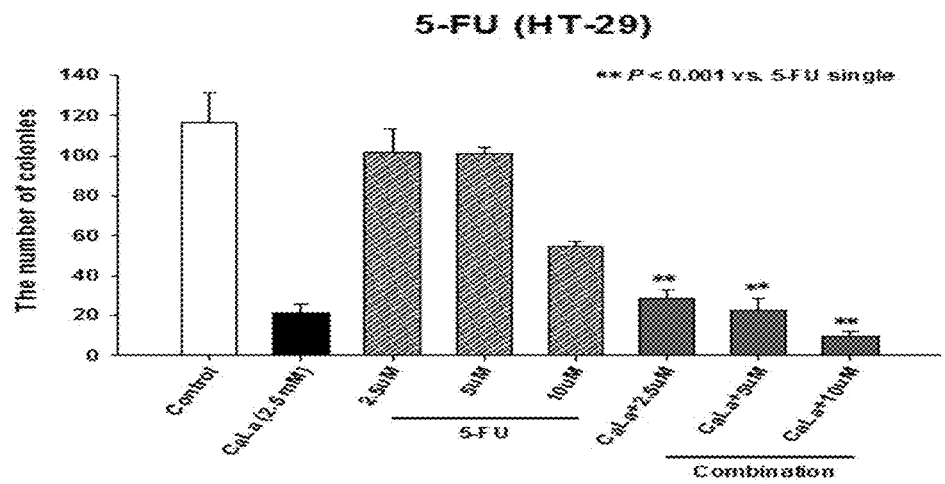
Figure 40B:
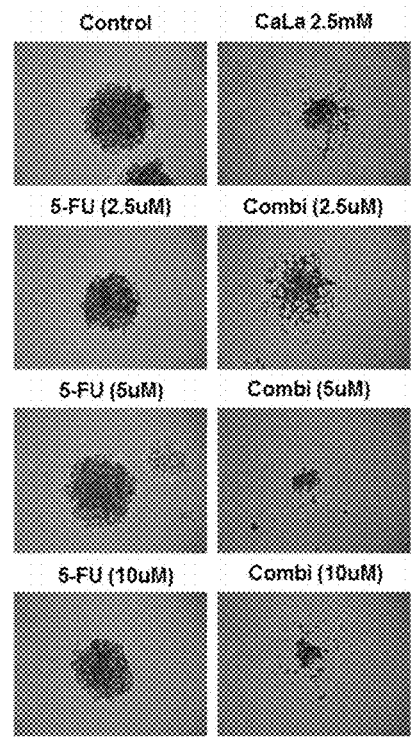

FIG. 40*a* shows the result of comparing the decrease in the number of colonies when a human colorectal cancer cell line (HT-29) was treated with 2.5 mM calcium lactate and 2.5 μM, 5 μM, and 10 μM 5-FU, alone or in combination. FIG. 40*b* shows the result of comparing the suppression of the formation of individual colony when a human colorectal cancer cell line (HT-29) was treated with 2.5 mM calcium lactate and 2.5 μM, 5 μM, and 1 μM 5-FU, alone or in combination.

Figure 41A:
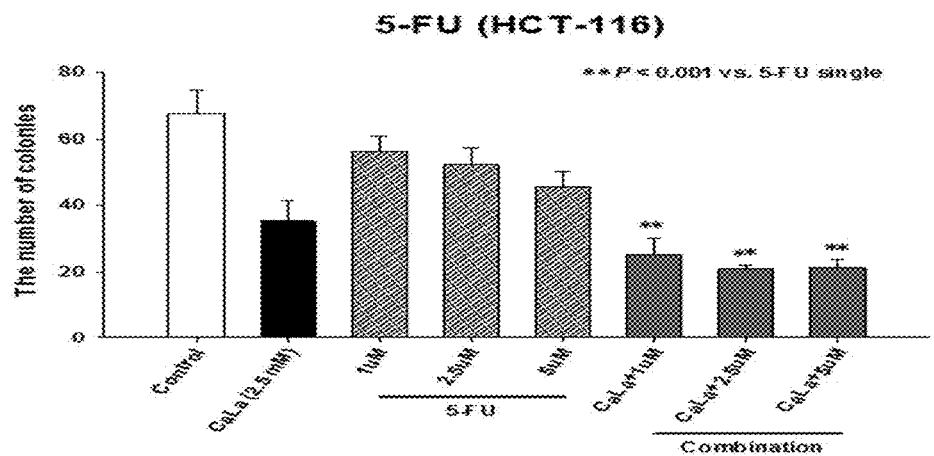
Figure 41B:
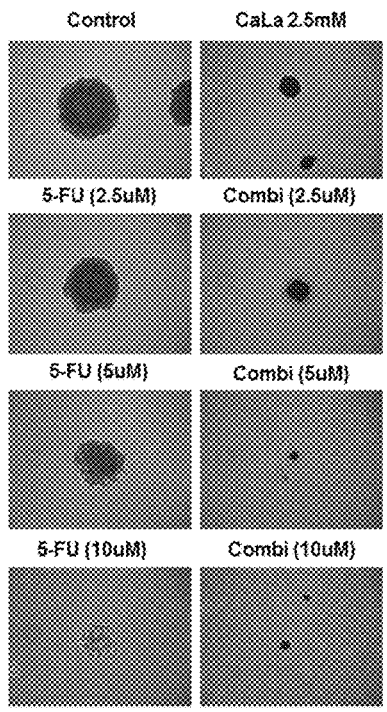

FIG. 41*a* shows the result of comparing the decrease in the number of colonies when a human colorectal cancer cell line (HCT-116) was treated with 2.5 mM calcium lactate and 2.5 μM, 5 μM, and 10 μM 5-FU, alone or in combination. FIG. 41*b* shows the result of comparing the suppression of the formation of individual colony when a human colorectal cancer cell line (HCT-116) was treated with 2.5 mM calcium lactate and 2.5 μM, 5 μM, and 10 μM 5-FU, alone or in combination.

Figure 42A:
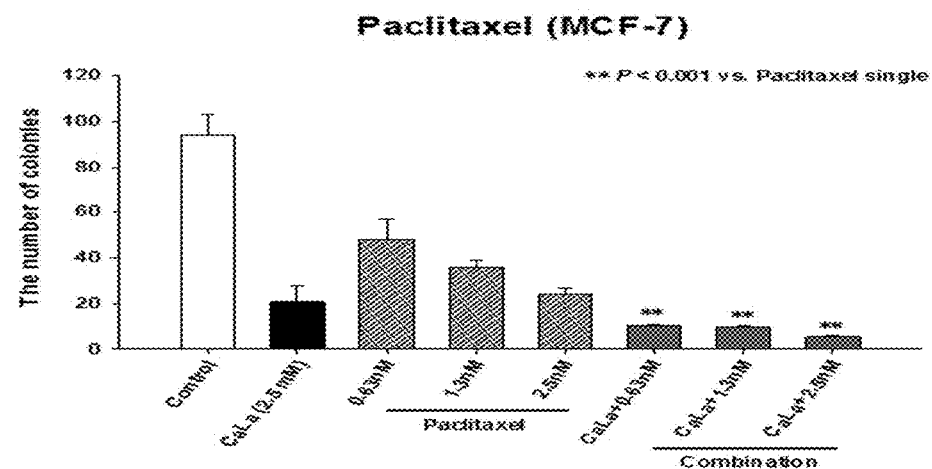
Figure 42B:
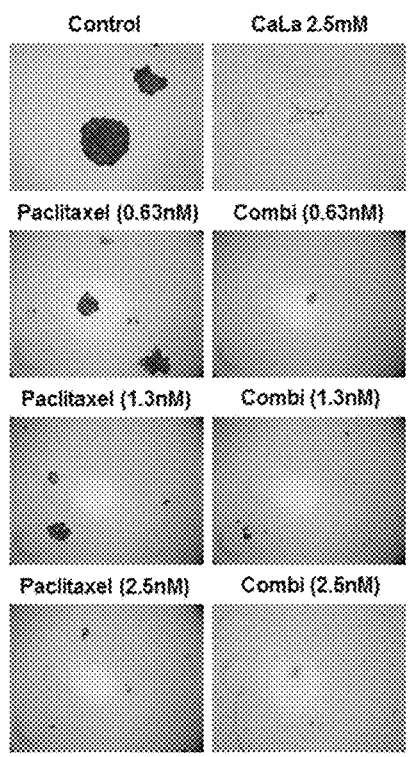

FIG. 42*a* shows the result of comparing the decrease in the number of colonies when a human breast cancer cell line (MCF-7) was treated with 2.5 mM calcium lactate and 0.63 nM, 1.3 nM, and 2.5 nM Paclitaxel, alone or in combination. FIG. 42*b* shows the result of comparing the suppression of the formation of individual colony when a human breast cancer cell line (MCF-7) was treated with 2.5 mM calcium lactate and 0.63 nM, 1.3 nM, and 2.5 nM Paclitaxel, alone or in combination.

Figure 43A:
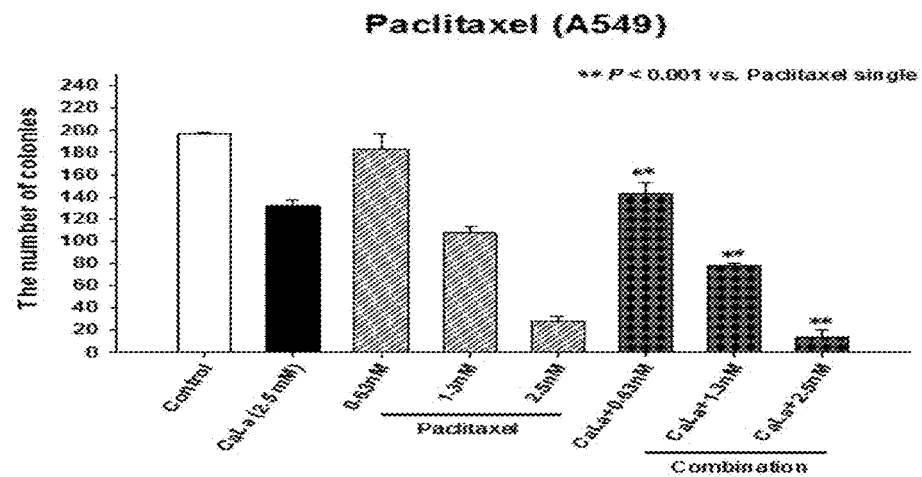
Figure 43B:
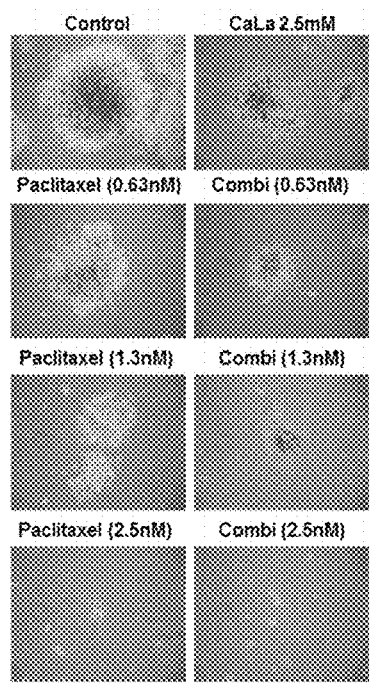

FIG. 43*a* shows the result of comparing the decrease in the number of colonies when a human lung cancer cell line (A549) was treated with 2.5 mM calcium lactate and 0.63 nM, 1.3 nM, and 2.5 nM Paclitaxel, alone or in combination. FIG. 43*b* shows the result of comparing the suppression of the formation of individual colony when a human lung cancer cell line (A549) was treated with 2.5 mM calcium lactate and 0.63 nM, 1.3 nM, and 2.5 nM Paclitaxel, alone or in combination.

Figure 44A:
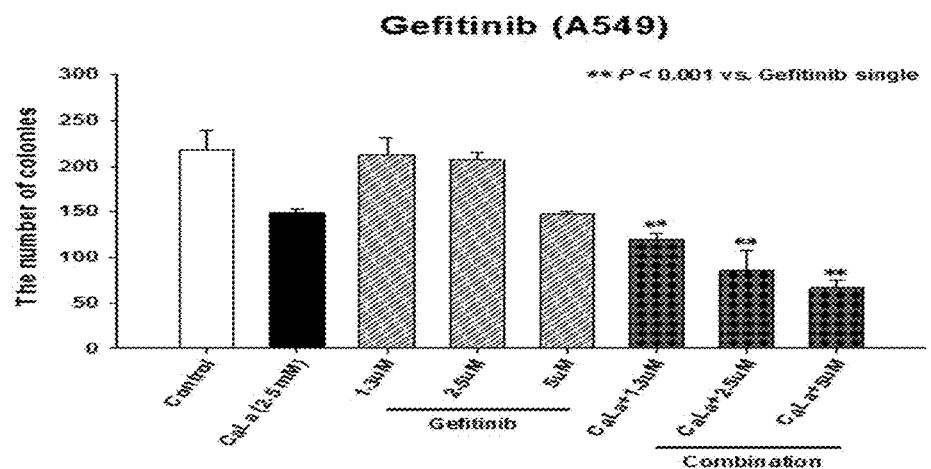
Figure 44B:
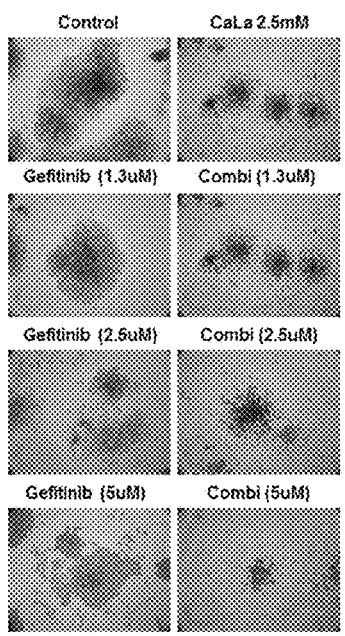

FIG. 44*a* shows the result of comparing the decrease in the number of colonies when a human lung cancer cell line (A549) was treated with 2.5 mM calcium lactate and 1.3 μM, 2.5 μM, and 5 μM Gefitinib, alone or in combination. FIG. 44*b* shows the result of comparing the suppression of the formation of individual colony when a human lung cancer cell line (A549) was treated with 2.5 mM calcium lactate and 1.3 μM, 2.5 μM, and 5 μM Gefitinib, alone or in combination.

Figure 45A:
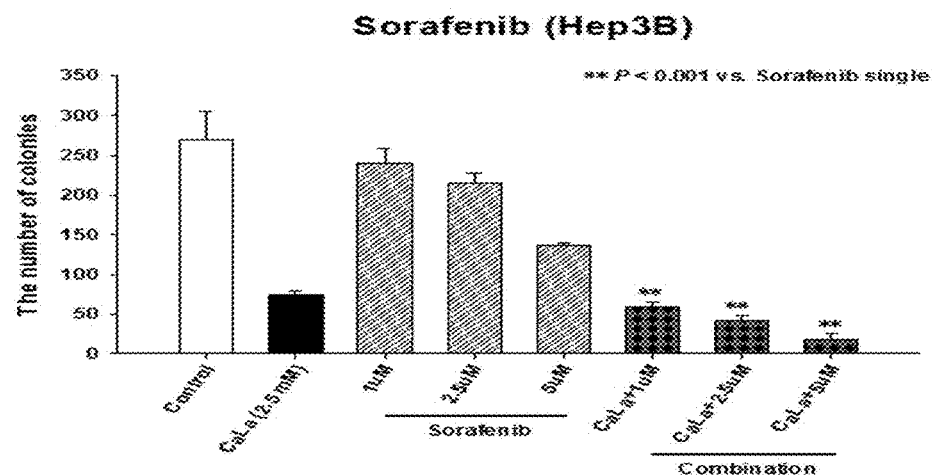
Figure 45B:
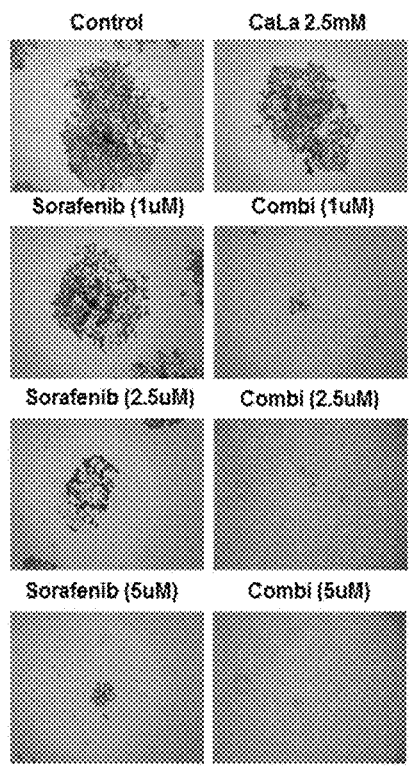

FIG. 45*a* shows the result of comparing the decrease in the number of colonies when a human hepatocellular carcinoma cell line (Hep3B) was treated with 2.5 mM calcium lactate and 1 μM, 2.5 μM, and 5 μM Sorafenib, alone or in combination. FIG. 45*b* shows the result of comparing the suppression of the formation of individual colony when a human hepatocellular carcinoma cell line (Hep3B) was treated with 2.5 mM calcium lactate and 1 μM, 2.5 μM, and 5 μM Sorafenib, alone or in combination.

Figure 46A:
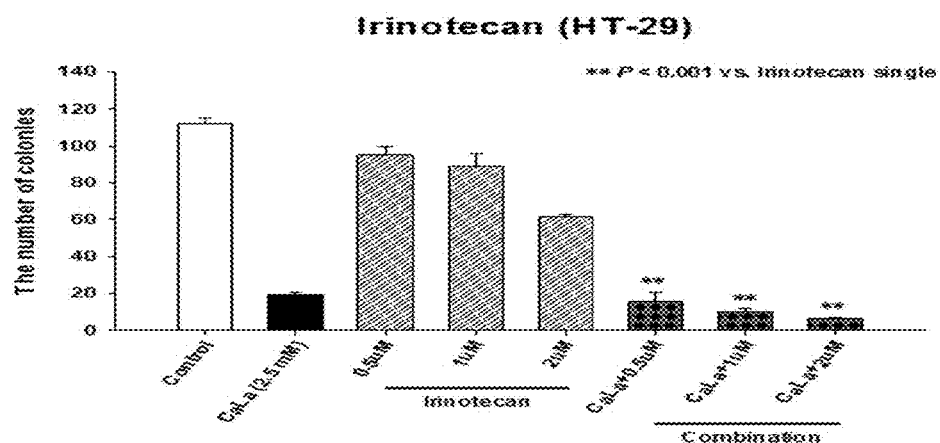
Figure 46B:
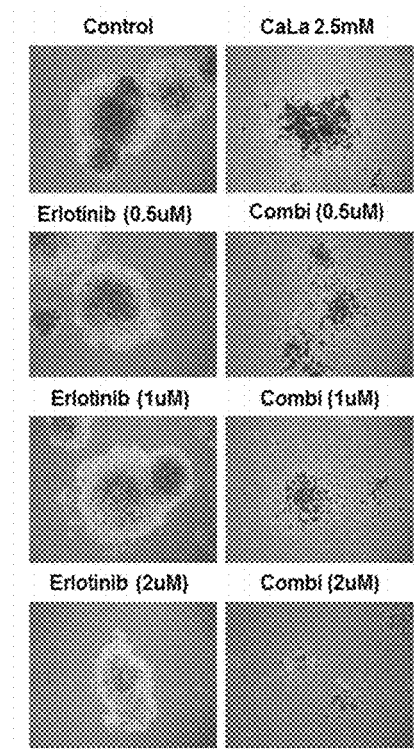

FIG. 46*a* shows the result of comparing the decrease in the number of colonies when a human colorectal cancer cell line (HT-29) was treated with 2.5 mM calcium lactate and 0.5 μM, 1 gμM, and 2 μM Irinotecan, alone or in combination. FIG. 46*b* shows the result of comparing the suppression of the formation of individual colony when a human colorectal cancer cell line (HT-29) was treated with 2.5 mM calcium lactate and 0.5 μM, 1 μM, and 2 μM Irinotecan, alone or in combination.

Figure 47A:
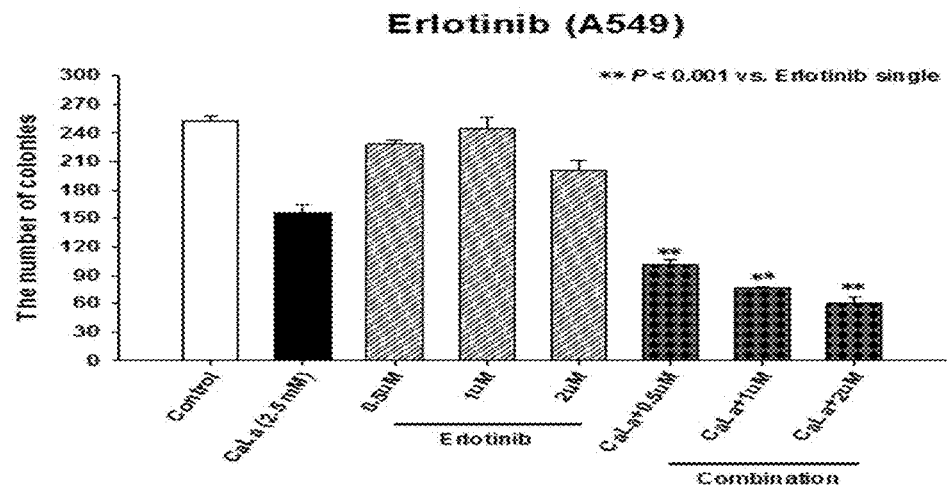
Figure 47B:
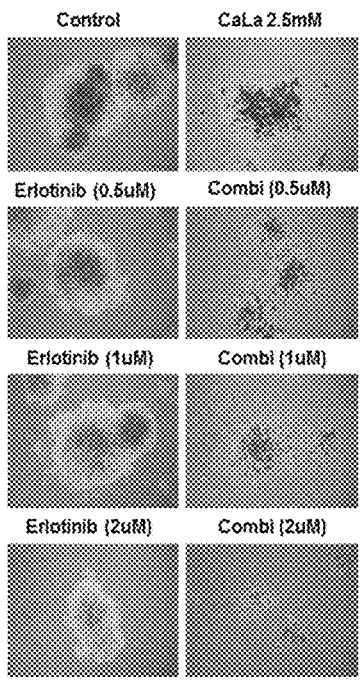

FIG. 47*a* shows the result of comparing the decrease in the number of colonies when a human lung cancer cell line (A549) was treated with 2.5 mM calcium lactate and 0.5 μM, 1 μM, and 2 μM Erlotinib, alone or in combination. FIG. 47*b* shows the result of comparing the suppression of the formation of individual colony when a human lung cancer cell line (A549) was treated with 2.5 mM calcium lactate and 0.5 μM, 1 μM, and 2 μM Erlotinib, alone or in combination.

Figure 48A:
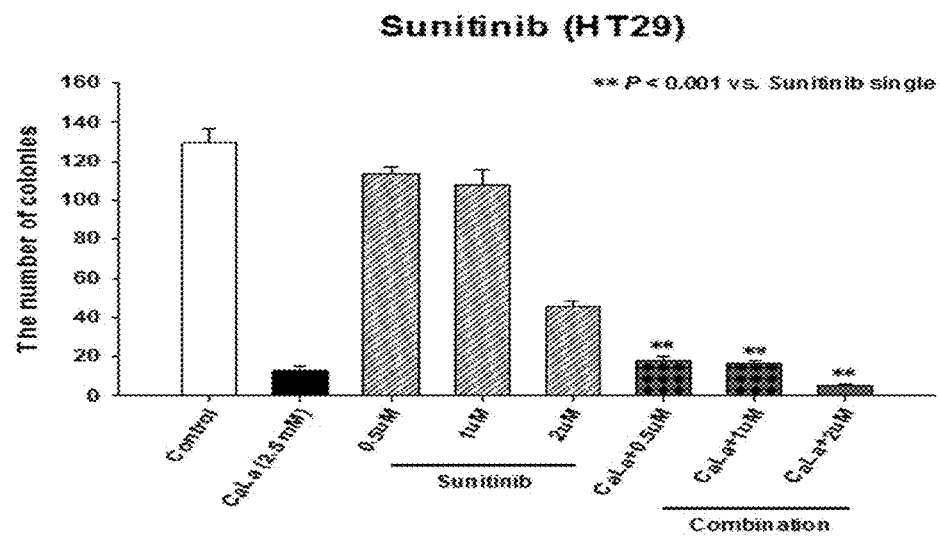
Figure 48B:
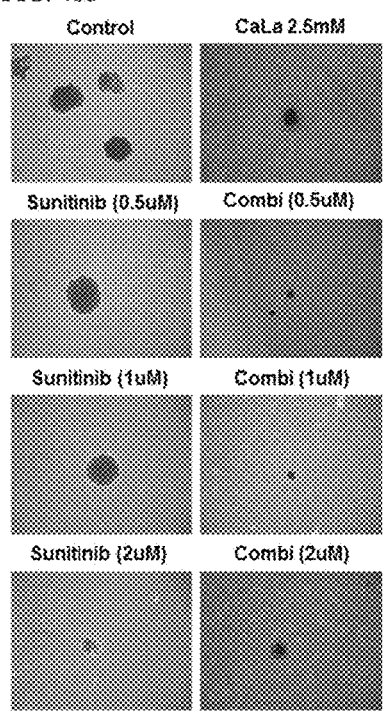

FIG. 48*a* shows the result of comparing the decrease in the number of colonies when a human colorectal cancer cell line (HT-29) was treated with 2.5 mM calcium lactate and 0.5 μM, 1 μM, and 2 μM Sunitinib, alone or in combination. FIG. 48*b* shows the result of comparing the suppression of the formation of individual colony when a human colorectal cancer cell line (HT-29) was treated with 2.5 mM calcium lactate and 0.5 μM, 1 μM, and 2 μM Sunitinib, alone or in combination.

Figure 49A:
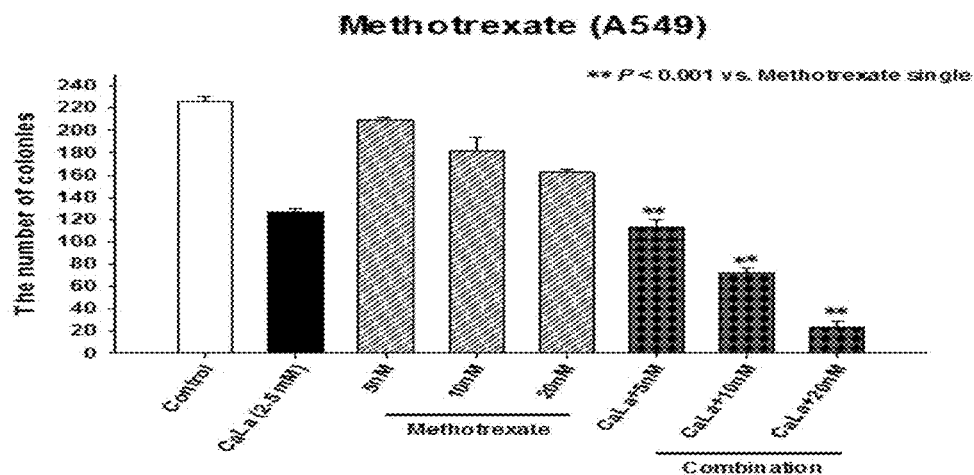
Figure 49B:
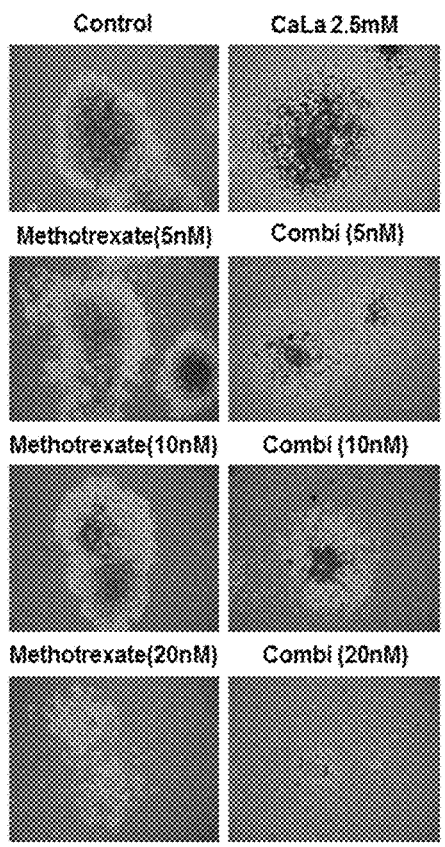

FIG. 49*a* shows the result of comparing the decrease in the number of colonies when a human lung cancer cell line (A549) was treated with 2.5 mM calcium lactate and 5 nM, 10 nM, and 20 nM Methotrexate, alone or in combination. FIG. 49*b* shows the result of comparing the suppression of the formation of individual colony when a human lung cancer cell line (A549) was treated with 2.5 mM calcium lactate and 5 nM, 10 nM, and 20 nM of Methotrexate, alone or in combination.

Figure 50A:
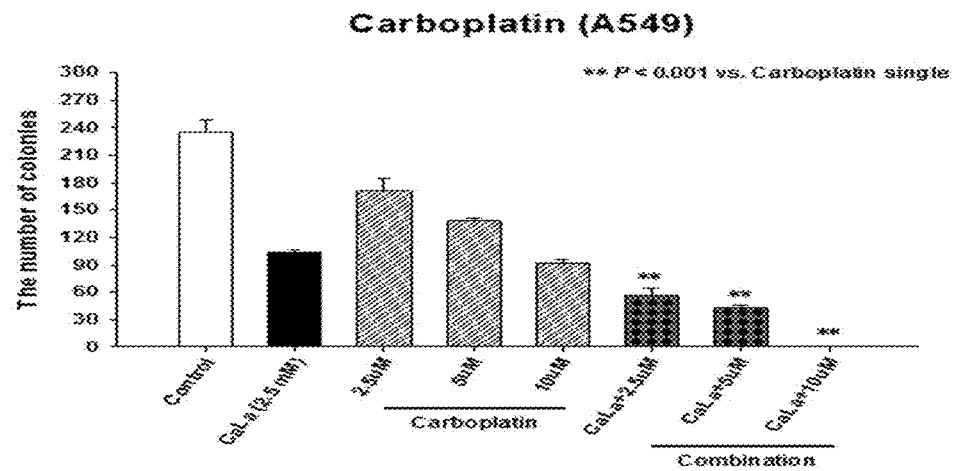
Figure 50B:
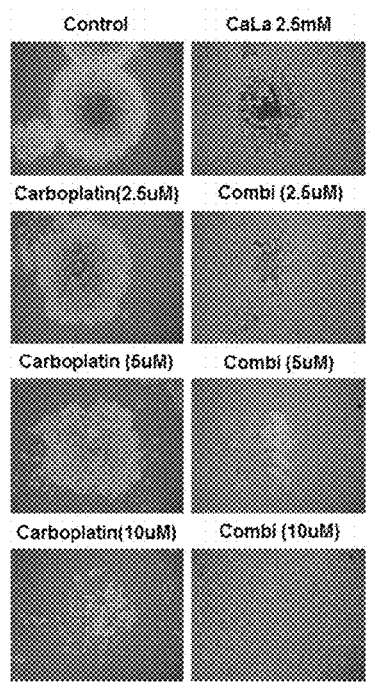

FIG. 50*a* shows the result of comparing the decrease in the number of colonies when a human lung cancer cell line (A549) was treated with 2.5 mM calcium lactate and 2.5 μM, 5 μM, and 10 μM Carboplatin, alone or in combination. FIG. 50*b* shows the result of comparing the suppression of the formation of individual colony when a human lung cancer cell line (A549) was treated with 2.5 mM calcium lactate and 2.5 μM, 5 μM, and 10 μM Carboplatin, alone or in combination.

Figure 51A:
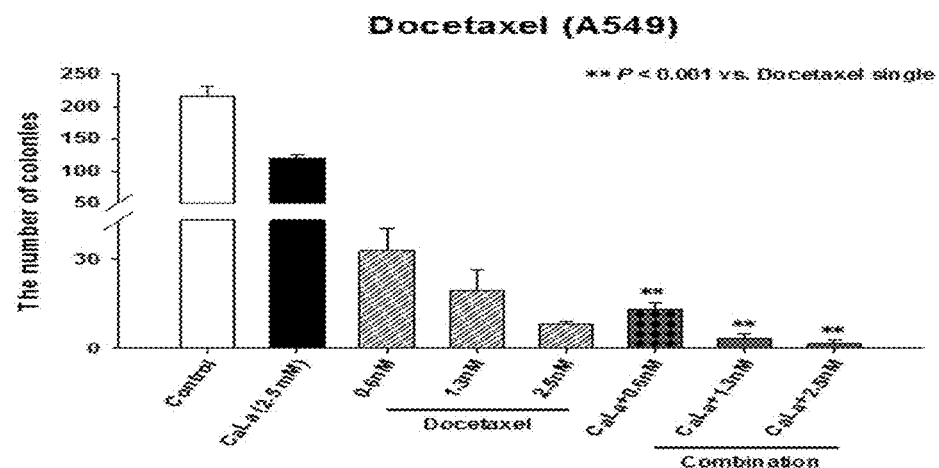
Figure 51B:
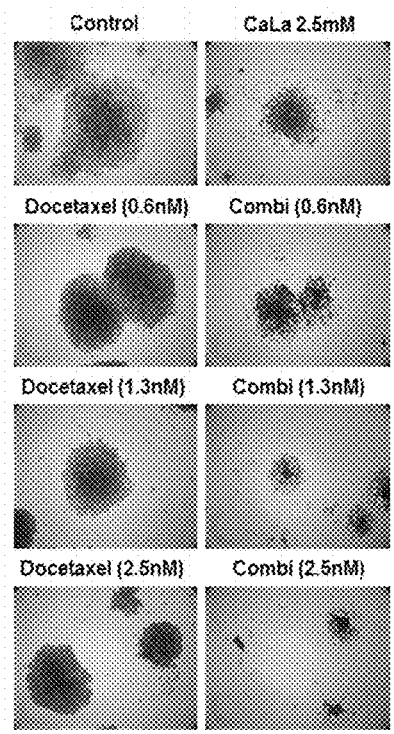

FIG. 51*a* shows the result of comparing the decrease in the number of colonies when a human lung cancer cell line (A549) was treated with 2.5 mM calcium lactate and 0.6 nM, 1.3 nM, and 2.5 nM Docetaxel, alone or in combination. FIG. 51*b* shows the result of comparing the suppression of the formation of individual colony when a human lung cancer cell line (A549) was treated with 2.5 mM calcium lactate and 0.6 nM, 1.3 nM, and 2.5 nM Docetaxel, alone or in combination.

Figure 52A:
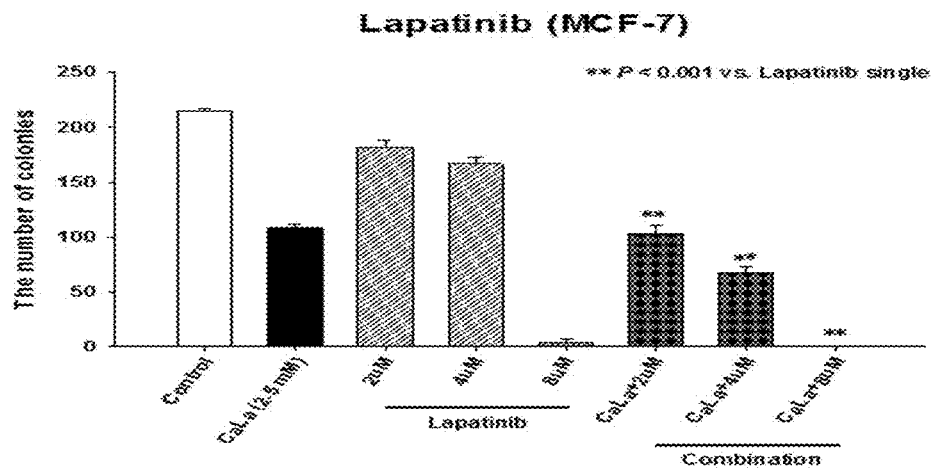
Figure 52B:
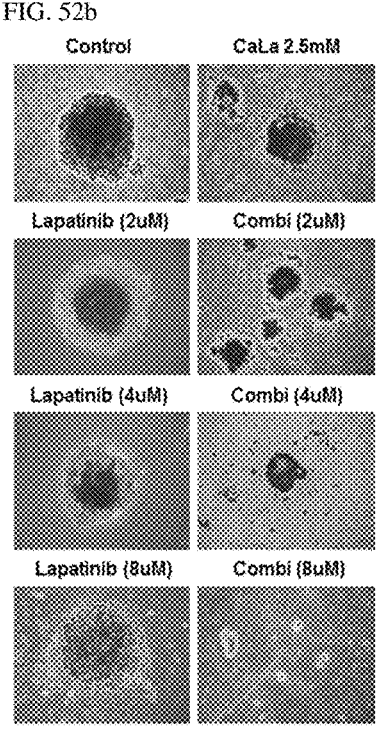

FIG. 52*a* shows the result of comparing the decrease in the number of colonies when a human breast cancer cell line (MCF-7) was treated with 2.5 mM calcium lactate and 2 μM, 4 μM, and 8 μM Lapatinib, alone or in combination. FIG. 52*b* shows the result of comparing the suppression of the formation of individual colony when a human breast cancer cell line (MCF-7) was treated with 2.5 mM calcium lactate and 2 μM, 4 μM, and 8 μM Lapatinib, alone or in combination.

Figure 53A:
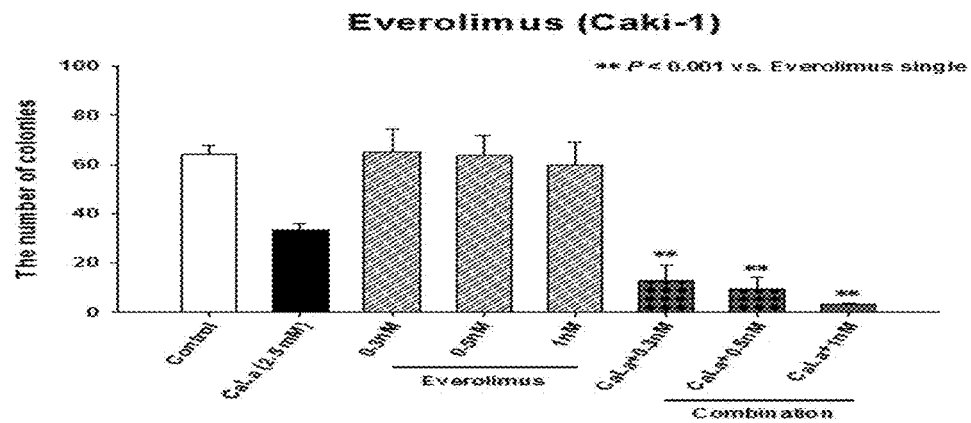
Figure 53B:
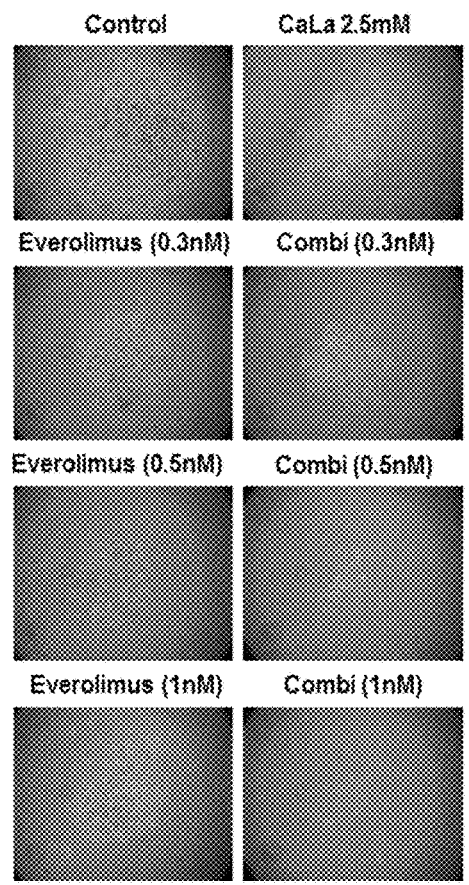

FIG. 53*a* shows the result of comparing the decrease in the number of colonies when a human kidney cancer cell line (Caki-1) was treated with 2.5 mM calcium lactate and 0.3 nM, 0.5 nM, and 1 nM Everolimus, alone or in combination. FIG. 53*b* shows the result of comparing the suppression of the formation of individual colony when a human kidney cancer cell line (Caki-1) was treated with 2.5 mM calcium lactate and 0.3 nM, 0.5 nM, and 1 nM Everolimus, alone or in combination.

Figure 54A:
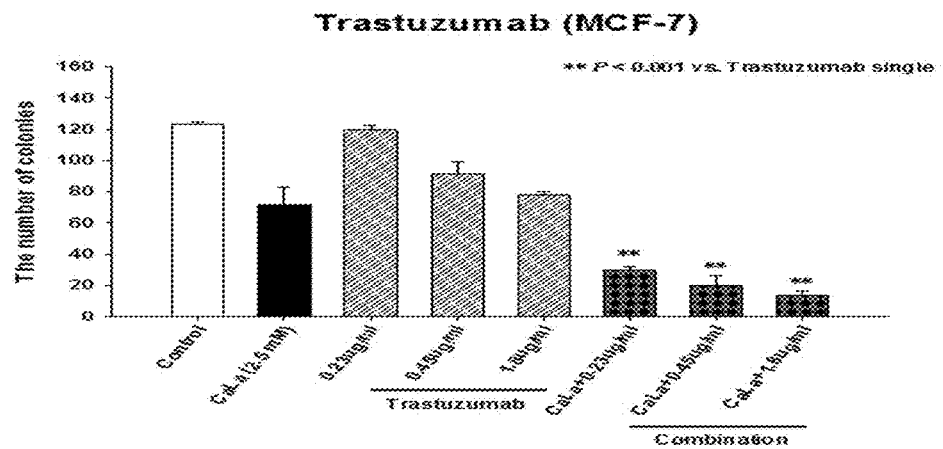
Figure 54B:
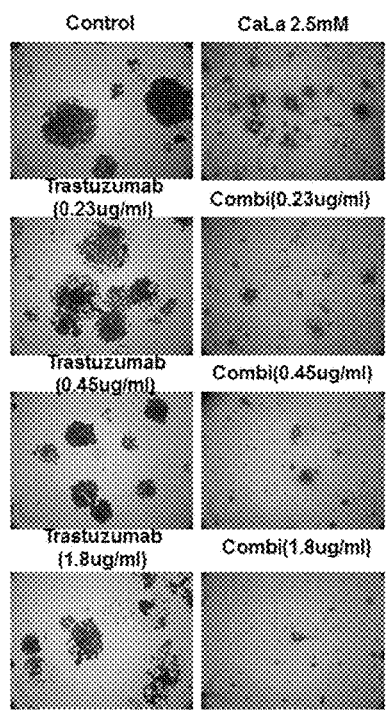

FIG. 54a shows the result of comparing the decrease in the number of colonies when a human breast cancer cell line (MCF-7) was treated with 2.5 mM calcium lactate and 0.23 µg/ml, 0.45 µg/ml, and 1.8 µg/ml Trastuzumab, alone or in combination. FIG. 54b shows the result of comparing the suppression of the formation of individual colony when a human breast cancer cell line (MCF-7) was treated with 2.5 mM calcium lactate and 0.23 µg/ml, 0.45 µg/ml, and 1.8 µg/ml Trastuzumab, alone or in combination.

Figure 55A:
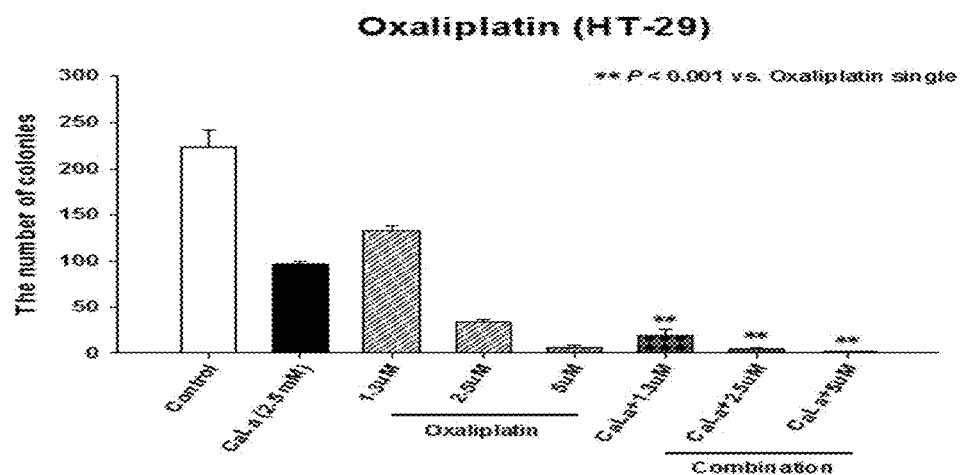
Figure 55B:
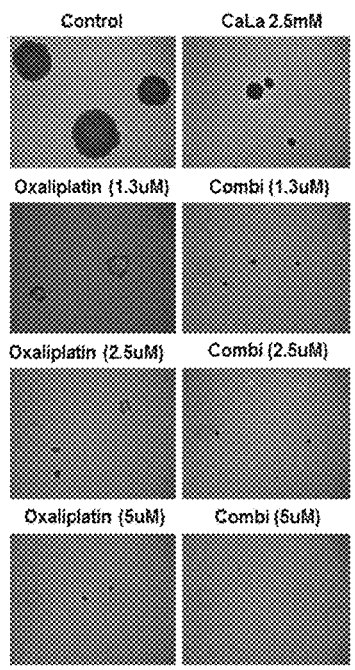

FIG. 55a shows the result of comparing the decrease in the number of colonies when a human colorectal cancer cell line (HT-29) was treated with 2.5 mM calcium lactate and 1.3 µM, 2.5 µM, and 5 µM Oxaliplatin, alone or in combination. FIG. 55b shows the result of comparing the suppression of the formation of individual colony when a human colorectal cancer cell line (HT-29) was treated with 2.5 mM calcium lactate and 1.3 µM, 2.5 µM, and 5 µM Oxaliplatin, alone or in combination.

DETAILED DESCRIPTION

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here.

The inventors of the present disclosure have conducted various studies for developing a method of treating cancer by effectively suppressing growth and metastasis of cancer cells and paid attention to the metabolic pathway of cancer cells. In cancer cells, energy is produced from glucose through glycolysis in which oxygen is not used, rather than through mitochondrial respiratory chain using a large amount of oxygen. During metabolism of cancer, lactate is produced in large amount. However, the acidity of the lactate causes inefficiency in survival of cancer cells. Thus, surplus lactate is exported to the outside of the cells. For this reason, it was assumed that by artificially administering a metal lactate salt to a cancer patient and accumulating lactate within cancer cells, the accumulated lactate can cause metabolic disorder of cancer or develop cancer microenvironment unfavorable to the survival of cancer and thus resultantly cause fatal damage.

Accordingly, a metal lactate salt was selected as a material for disturbing metabolism of cancer cells. This is because it was expected that since glucose is converted into pyruvate through glycolysis and then forms lactate, if lactate can be accumulated in cancer cells, the glycolysis may slow down or stop. However, lactate can be easily degraded in the body and thus cannot be effectively transported to cancer cells. Thus, it was expected that lactate cannot readily be degraded in an extracellular environment but can be easily introduced into cells and effectively degraded therein by using a metal lactate salt.

Meanwhile, the inventors of the present disclosure considered that in the case of using a metal lactate salt including a metallic component which cannot be easily metabolized in the body, the metallic component may cause a side effect due to characteristics of an anticancer drug which can be frequently administered in a large amount, and thus selected among various metal lactate salts a metal lactate salt from sodium lactate, potassium lactate, and calcium lactate, which has an excellent binding force with respect to lactate and an excellent lactate delivery efficiency to a cancer cell without containing a metallic component which cannot be easily metabolized in the body. As a result, it was confirmed that calcium lactate has the highest binding force with respect to lactate and the highest lactate delivery efficiency to a cancer cell, and calcium lactate was finally selected.

As a result of administration of the selected calcium lactate to cancer cells, it was confirmed that the levels of lactate, LDH-B (lactate dehydrogenase B), which affects metabolism of lactate, pyruvate, PDH (pyruvate dehydrogenase), which affects metabolism of pyruvate, and α-KG (α-ketoglutarate) in cells are increased; the levels of β-catenin, as a cancer growth factor, PARP, which suppresses intracellular DNA damage, HIF-1α (hypoxia inducible factor 1α) and VEGF (vascular endothelial growth factor), which affect cancer cell metastasis, invasion, and angiogenesis in cells are decreased; and the levels of growth, metastasis (migration), and tube formation of the cancer cells are decreased.

Further, the anticancer activity of calcium lactate was measured using animal models and it was confirmed that administration of calcium lactate suppressed growth of cancer cells in animal models.

Furthermore, in case of administration in combination with conventional radiation, it was confirmed that the equivalent anticancer effect can be obtained with a decreased amount of radiation as compared with the conventional case. Also, in case of administration to relevant cancer cell lines in combination with various kinds of well-known anticancer drugs, it was confirmed that a higher anticancer effect can be obtained with a decreased concentration of the anticancer drugs as compared with a case of administration alone.

Most of metal lactate salts showing such anticancer activities can be metabolized in the body and known as having no side effects. Thus, the metal lactate salts can be used as active ingredients of anticancer drugs or health foods with safety and excellent anticancer activity. The anticancer effects of these metal lactate salts have not been known before, but have been demonstrated first by the inventors of the present disclosure.

An exemplary embodiment of the present disclosure provides a pharmaceutical composition for treating cancer including metal lactate salts as active ingredients.

The term "metal lactate salts" used herein refers to compounds produced or synthesized in the form of lactic acid bonded to a metal ion.

In the present disclosure, if the metal lactate salts are administered into a cancer cell, the metal lactate salts are used to dissociate lactate and thus increase the concentration of lactate in the cancer cell. Metal lactate salts used as active ingredients of a pharmaceutical composition for treating cancer according to the present disclosure are not particularly limited as long as they can disturb metabolism of a cancer cell. In one example, calcium lactate, zinc lactate, magnesium lactate, sodium lactate, potassium lactate, ferrous lactate, chromium lactate, copper lactate, and manganese lactate capable of forming a stable compound outside a cell and dissociating lactate and thus increasing the concentration of lactate in a cancer cell may be used individually or in combination. In another example, calcium lactate, sodium lactate, and potassium lactate capable of forming a stable compound outside a cell and dissociating lactate and thus increasing the concentration of lactate in a cancer cell without containing a metallic component which cannot be easily metabolized in the body may be used individually or in combination. In yet another example, calcium lactate capable of forming a stable compound outside a cell and dissociating lactate and thus increasing the concentration of lactate in a cancer cell with excellent delivery efficiency to the cancer cell without containing a metallic component which cannot be easily metabolized in the body may be used.

In the present disclosure, all of calcium lactate, sodium lactate, and potassium lactate are synthesized as metal lactate salts, and it was confirmed that these metal lactate salts can be dissociated to lactate in a cancer cell. Particularly, calcium lactate having the highest lactate delivery efficiency was used to demonstrate various anticancer activities.

However, calcium lactate is just an example of metal lactate salts provided in the present disclosure. The metal lactate salts provided in the present disclosure are not limited to calcium lactate, and it is obvious that various metal lactate salts can be used as active ingredients of a pharmaceutical composition for treating cancer according to the present disclosure.

The metal lactate salts can show improved anticancer activity in case of administration in combination with a conventional anticancer drug. This is because the conventional anticancer drug does not have a mechanism involved in glycolysis of a cancer cell. Therefore, an anticancer drug which can be administered in combination with the pharmaceutical composition for treating cancer provided in the present disclosure is not particularly limited as long as it is not directly involved in glycolysis of a cancer cell. For example, Imatinib, 5-FU (5-Florouracil), Irinotecan, Sunitinib, Oxaliplatin, Paclitaxel, Lapatinib, Trastuzumab (Herceptin), Gefitinib, Erlotinib, Methotrexate, Carboplatin, Docetaxel, Everolimus, and Sorafenib, which are well-known anticancer drugs, 5-indane sulfonamide (IS), which is a carbonic anhydrase inhibitor known as having an anticancer activity, and cinnamic acid (CA), which is a monocarboxylate transporter inhibitor, may be used.

Further, the metal lactate salts decrease the expression of PARP, HIF-1α and VEGF that give a cancer cell resistance to radiation in case of radiation. Thus, in case of administration of the metal lactate salts in combination with radiation, the metal lactate salts improve the anticancer activity of radiation. Therefore, it is possible to obtain an equivalent anticancer effect with a decreased amount of radiation as compared with the conventional case. In this case, the amount of radiation is not particularly limited, and may be 2 to 10 Gy per day. The radiation may be irradiated once per day, or may be irradiated over several days by dividing the amount of radiation.

The term "calcium lactate" refers to a type of lactate metal salts and represented by $C_6H_{10}O_6Ca.5H_2O$ in which calcium ion is bonded to lactate. Calcium lactate is in the form of white powder or granules at room temperature, anhydrous at 120° C. heating condition, and has a solubility of 5% (w/v). Further, calcium lactate has excellent bioavailability and body absorption and has not been known as having a side effect and thus has been used mainly as a calcium enhancer or a pH regulator of foods.

In the present disclosure, calcium lactate can be used as an example of metal lactate salts which are active ingredients of the pharmaceutical composition for treating cancer. Since calcium bound to lactate is more absorbable into cancer cells than normal cells, calcium lactate has the advantage of relatively higher efficiency of lactate delivery to cancer cells than other types of lactate metal salts.

Cancers which can be treated with the pharmaceutical compositions provided in the present disclosure are not particularly limited as long as growth, invasion, and metastasis thereof can be suppressed by disturbing metabolism thereof. In one example, solid cancers such as lung cancer, breast cancer, colorectal cancer, stomach cancer, brain cancer, pancreatic cancer, thyroid cancer, skin cancer, bone cancer, lymphoma, uterine cancer, cervical cancer, kidney cancer, and melanoma, of which growth, invasion, and metastasis can be suppressed by disturbing glycolysis may be included. In another example, colorectal cancer, breast cancer, and melanoma, of which growth, invasion, and metastasis can be suppressed by a treatment with metal lactate salts, may be included.

Figure 1:
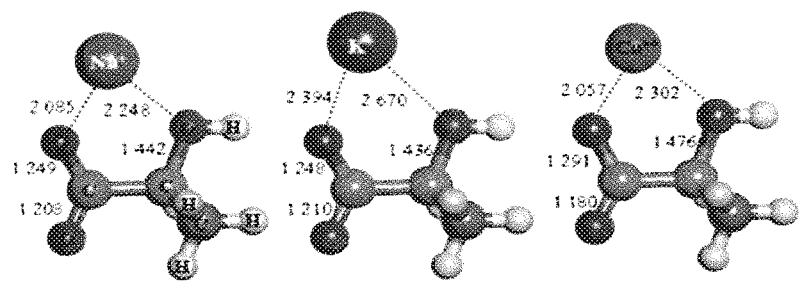
FIG. 1 shows a schematic diagram and a table comparing the structure and binding energy among calcium lactate, sodium lactate and potassium lactate, each having a molecular structure similar to that of calcium lactate.

According to an exemplary embodiment of the present disclosure, in order to synthesize metal lactate salts, among various metal lactate salts, each of calcium lactate, sodium lactate, and potassium lactate, which does not contain metal that can be harmful in the body, was synthesized. Then, by comparison of binding energy and lactate delivery efficiency to a cancer cell, it was confirmed that calcium lactate has the highest binding force with respect to lactate and the highest lactate delivery efficiency to a cancer cell, and calcium lactate was finally selected (FIG. 1).

Figure 3:
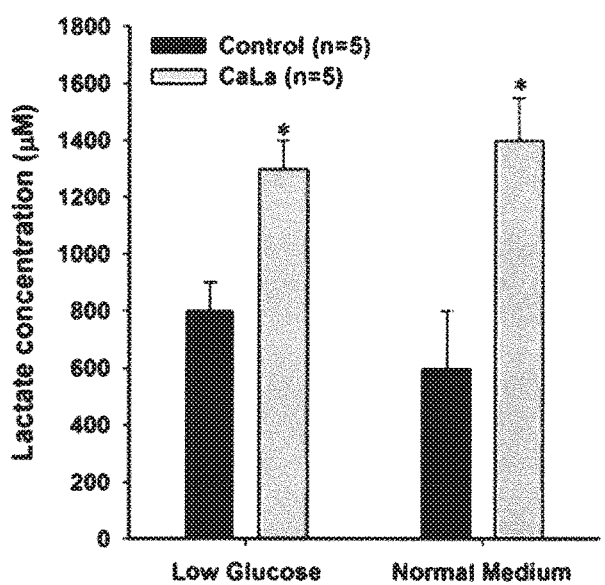
FIG. 3 is a graph showing the result of comparing the lactate levels in cancer cells depending on whether or not treated with calcium lactate (CaLa).
Figure 4:
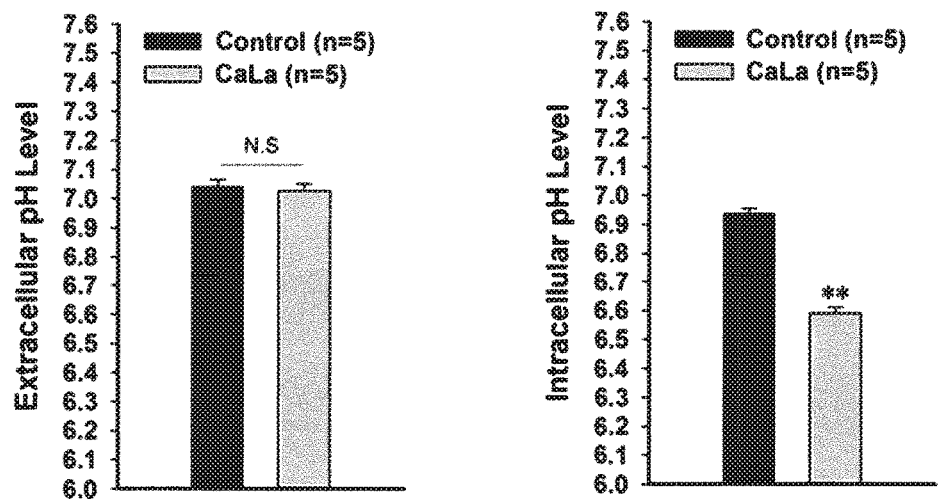
FIG. 4 provides graphs showing the changes in intracellular and extracellular pH of cancer cells treated with calcium lactate, and the left graph shows the change in extracellular pH of the cancer cells and the right graph shows the change in intracellular pH of the cancer cells.

In case of treating a cancer cell with the selected calcium lactate, it was confirmed that the calcium concentration (FIG. 2) and lactate concentration (FIG. 3) in the cancer cell increased and the pH in the cell decreased (FIG. 4). Further, it was confirmed that the expression of β-catenin as a cancer growth factor was suppressed according to gene decoding (FIG. 5), and both of β-catenin and activated β-catenin decreased in protein expression as the concentration of calcium lactate increased (FIG. 6). Furthermore, it was confirmed that calcium lactate decreased protein expression of PARP, which repairs intracellular DNA damage, in a breast cancer cell line (FIG. 8), a colorectal cancer cell line (FIG. 9), and a melanoma cell line (FIG. 10); increased the protein expression of LDH-B (lactate dehydrogenase B), which affects metabolism of intracellular lactate (FIGS. 11a, 11b, and 11c), increased pyruvate level (FIG. 12), increased the protein expression of PDH (pyruvate dehydrogenase) (FIGS. 13a and 13b), and increased α-KG (α-ketoglutarate) level (FIGS. 14a and 14b); suppressed the protein expression of HIF-1α (hypoxia inducible factor 1α) (FIG. 15) and VEGF (vascular endothelial growth factor) (FIGS. 16a and 16b), which affects metastasis, invasion, and angiogenesis of a cancer cell, and suppressed the tube formation levels of HUVEC (FIG. 17); suppressed cell migration of a colorectal cancer cell line (FIG. 18), a breast cancer cell line (FIG. 19) and a melanoma cell line (FIG. 20); increased the cell apoptosis rate of a breast cancer cell line (FIGS. 21a, 21b, 21c, 21d, and 21e) and a colorectal cancer cell line (FIG. 22); inhibited the colony-forming ability of a colorectal cancer cell line (FIG. 23) and a melanoma cell line (FIGS. 24a and 24b); and increased anticancer efficiency in case of administration in combination with a conventional anticancer drug (FIGS. 25a and 25b).

Further, as a result of testing the anticancer activity of calcium lactate using animal models, it was confirmed that in a mouse animal model prepared with dissemination of a colorectal cancer cell line, the PARP degrading activity increased (FIG. 28), the expressions of HIF-1α and VEGF were suppressed (FIGS. 29 and 31), the growth of tumor was suppressed (FIGS. 30, 32, and 34), and the tumor volume was decreased and angiogenesis was also decreased (FIGS. 33 and 35). Meanwhile, as a result of administration of calcium lactate in combination with radiation, it was confirmed that the growth of tumor was decreased more effectively (FIGS. 37a and 37b).

Moreover, in the case of administration of calcium lactate in combination with various anticancer drugs used for treating various cancers, it was confirmed that the growth of tumor was suppressed more effectively as compared with the case in which the anticancer drugs were administered alone (FIGS. 38a, 38b to 55a, and 55b).

The pharmaceutical composition of the present disclosure may be prepared in the form of a pharmaceutical composition for treating cancer and may further include appropriate carriers, excipients, or diluents that are generally used in preparation of a pharmaceutical composition. Specifically, the pharmaceutical composition may be formulated, according to a traditional method, into oral dosage forms such as powder, granule, tablet, capsule, suspension, emulsion, syrup, aerosol, oral patch, etc., external preparation, patch for external use, suppository or in the form of sterile injectable solutions. In the present disclosure, the carriers, excipients and diluents which may be included in the pharmaceutical composition may be lactose, dextrose, sucrose, sorbitol, mannitol, xylitol, erythritol, maltitol, starch, acasia rubber, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate, and mineral oil. The formulation of the composition may involve using diluents or excipients such as fillers, bulking agents, binders, wetting agents, disintegrants, surfactants, etc. The solid formulations for oral administration may include tablets, depots, pills, powders, granules, capsules, oral patches, etc. The solid formulations may be prepared by mixing at least one excipient, such as starch, calcium carbonate, sucrose, lactose, or gelatin, etc. with the extracts and fractions thereof. In addition to such general excipients, lubricants such as magnesium stearate or talc may also be used. The liquid formulations for oral administration may include suspensions, solutions for internal use, emulsions, syrups, etc. In addition to general diluents such as water and liquid paraffin, different excipients such as wetting agents, flavors, fragrances, preserves, etc., may be included. The formulations for parenteral administration may include sterile aqueous solutions, non-aqueous solvents, suspensions, emulsions, lyophilized preparations, patches for external use, or suppositories. The non-aqueous solutions and the suspensions may include propylene glycol, polyethylene glycol, vegetable oil such as olive oil, injectable ester such as ethyloleate, etc. The base for suppositories may include witepsol, macrogol, tween 61, cacao butter, laurin butter, glycerogelatin, etc.

The amount of metal lactate salts included in the pharmaceutical composition of the present disclosure may be, but is not particularly limited to, between 0.0001 wt % and 50 wt %, or more preferably between 0.01 wt % and 20 wt %, based on the total weight of the final composition. The concentration of the metal lactate salts included in a single dose of the pharmaceutical composition may be 2.5 mM to 25 mM.

The pharmaceutical composition of the present disclosure may be administered in a pharmaceutically effective amount, and as used herein, the term "pharmaceutically effective amount" refers to an amount sufficient to treat or prevent diseases, at a reasonable benefit/risk ratio applicable to any medical treatment or prevention. The effective dosage level may be determined depending on severity of the disease, activity of the drug, a patient's age, body weight, health and sex, sensitivity to the drug, administration time, administration route, and excretion rate of the composition of the present disclosure, duration of treatment, drugs used simultaneously or in combination with the composition of the present disclosure, and other factors known in the medical field. The pharmaceutical composition of the present disclosure may be administered alone or in combination with other publicly-known anticancer drugs or components known as known as having an anticancer activity. It is important to administer the composition in the minimum amount that can exhibit the maximum effect without causing side effects, in consideration of all the above factors.

The dosage of the pharmaceutical composition of the present disclosure may be determined by those skilled in the art in consideration of the purpose of use, severity of the disease, a patient's age, body weight, sex, and anamnesis, the kind of material used as an active ingredient, or the like. The pharmaceutical composition of the present disclosure may be administered, for example, at a dosage of about 0.1 ng to about 1,000 mg/kg per adult, or preferably 1 ng to about 100 mg/kg per adult, and the administration frequency of the composition of the present disclosure may be, but is not particularly limited to, once or a few divided doses a day. The dosage or the administration frequency does not limit the scope of the present disclosure in any way.

Another exemplary embodiment of the present disclosure provides a method of treating cancer including the step of administering a pharmaceutically effective amount of the pharmaceutical composition to a subject having cancer.

As used herein, the term "subject" includes all mammals including mice, livestock, and humans, and farm fish that have cancer, without limitations.

The term "treatment" used herein refers to all activities to alleviate or improve the symptoms of cancer by administering the pharmaceutical composition including the metal lactate salts as active ingredients of the present disclosure to a subject having cancer.

In the method of treating cancer of the present disclosure, the kinds of cancer to be treated are the same as described above.

The composition can be administered in a single or multiple dosage form. In this case, the composition may be formulated into liquid, powder, aerosol, injection, fluid transfusion (intravenous drip), capsule, pill, tablet, suppository, or patch.

The pharmaceutical composition for treating cancer of the present disclosure may be administered via any of common routes as long as it is able to reach a target tissue.

The pharmaceutical composition of the present disclosure may be administered, but not particularly limited to, intraperitoneally, intravenously, intramuscularly, subcutaneously, intradermally, in the form of a transdermal patch, orally, intranasally, intrapulmonarily or intrarectally depending on the purpose. However, the pharmaceutical composition may be administered in a non-formulated form for oral administration, and since the metal lactate salts may be denatured by gastric acid upon oral administration, active ingredients of a composition for oral administration should be coated or formulated for protection against degradation in the stomach, or orally administered in the form of a patch for oral administration. In addition, the composition may be administered using a certain apparatus capable of transporting the active ingredients into a target cell.

Yet another exemplary embodiment of the present disclosure provides a pharmaceutical composition for treating cancer including metal lactate salts and anticancer drug as active ingredients.

As described above, the metal lactate salts provided in the present disclosure can show improved anticancer activity in cases of administration in combination with a conventional anticancer drug. This is because the conventional anticancer drug does not have a mechanism involved in glycolysis of a cancer cell. Therefore, an anticancer drug including a metal lactate salt provided in the present disclosure and an active ingredient of publicly-known anticancer drugs can be used more effectively for treating cancer.

Herein, the metal lactate salts, the publicly-known anticancer drugs, cancer to which the pharmaceutical composition for treating cancer can be applied, the dosage, the administration method, and the like are the same as described above.

Still another exemplary embodiment of the present disclosure provides a pharmaceutical composition for suppressing cancer metastasis including metal lactate salts as active ingredients.

The metal lactate salts provided in the present disclosure can suppress various characteristics which can induce metastasis of cancer cells, such as metastasis, invasion, angiogenesis of cancer cells, tube formation, cell migration, colony-forming ability, etc., and, thus, can be used as active ingredients of a pharmaceutical composition for suppressing cancer metastasis.

Herein, a metastasis-suppressed target cancer is the same as defined above. For example, the pharmaceutical composition for suppressing cancer metastasis may be used for suppressing the occurrence of one or more metastatic cancers selected from the group consisting of metastatic lung cancer, breast cancer, colorectal cancer, stomach cancer, brain cancer, pancreatic cancer, thyroid cancer, skin cancer, bone cancer, lymphoma, uterine cancer, cervical cancer, kidney cancer, and melanoma.

According to an exemplary embodiment of the present disclosure, when various cancer cells were treated with calcium lactate as a kind of metal lactate salts provided in the present disclosure, it was confirmed that the protein expressions of HIF-1α (hypoxia inducible factor 1α) (FIG. 15) and VEGF (vascular endothelial growth factor) (FIG. 16), which affect metastasis, invasion, and angiogenesis of a cancer cell, and the tube formation levels of HUVEC (FIG. 17) were suppressed; cell migrations of a colorectal cancer cell line (FIG. 18), a breast cancer cell line (FIG. 19) and a melanoma cell line (FIG. 20) were suppressed; cell apoptosis rates of a breast cancer cell line (FIG. 21) and a colorectal cancer cell line (FIG. 22) were increased; and colony-forming abilities of a colorectal cancer cell line (FIG. 23) and a melanoma cell line (FIG. 24) were inhibited.

Still another exemplary embodiment of the present disclosure provides a food composition for improving cancer including metal lactate salts as active ingredients.

The metal lactate salts have been generally used for metabolism in vivo, and calcium lactate was certified as having no side effects and has been used as an official food additive. Thus, the metal lactate salts can be taken in the form of a food which can be daily eaten and can promote the improvement of cancer. Herein, the amount of metal lactate salts included in the food may be, but is not particularly limited to, between 0.001 wt % and 10 wt %, or between 0.1 wt % and 1 wt %, based on the total weight of the food composition. If the food is a beverage, the metal lactate salts may be included at a ratio of 1 g to 10 g or 2 g to 7 g per 100 ml.

Further, the composition may further include additional components which have been typically used in a food composition to improve smell, taste, appearance, etc., for example, vitamins A, C, D, E, B1, B2, B6, B12, niacin, biotin, folate, panthotenic acid, etc. Furthermore, the composition may further include minerals such as Zn, Fe, Ca, Cr, Mg, Mn, Cu, etc. Moreover, the composition may further include amino acids such as lysine, tryptophan, cysteine, valine, etc. In addition, the composition may further include food additives such as preservatives (potassium sorbate, sodium benzoate, salicylic acid, dehydro sodium acetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vaniline, lactones, etc.), swelling agents (alum, potassium D-hydrogen tartrate, etc.), fortifiers, emulsifiers, thickeners (adhesive pastes), film-forming agents, gum base agents, antifoaming agents, solvents, improvers, etc. The food additives may be selected according to the kind of food and used in an appropriate amount.

Meanwhile, functional foods for improving cancer may be manufactured using the food composition for improving cancer including metal lactate salts.

Specifically, processed foods capable of improving cancer may be manufactured using the food composition. Examples of the processed foods may be manufactured as functional foods in the form of cookies, beverages, alcoholic beverages, fermented foods, canned foods, milk-processed foods, meat-processed foods, or noodles. Herein, examples of the cookies include biscuits, pies, cakes, breads, candies, jellies, gums, cereals (meal substitutes such as grain flakes). Examples of beverages include drinking water, carbonated soft drinks, functional isotonic drinks, juices (e.g., apple-, pear-, grape-, aloe-, tangerine-, peach-, carrot-, tomato juices, etc.), sweet rice drinks, etc. Examples of alcoholic beverages include refined rice wine, whisky, soju (Korean distilled spirits), beer, liquors, fruits wine, etc. Examples of fermented foods include soy sauce, bean paste, red pepper paste, etc. Examples of canned foods include seafood canned foods (e.g., canned tuna, mackerel, mackerel pike, conch, etc.), livestock canned foods (canned beef, pork, chicken, turkey, etc.), and agricultural canned foods (canned corn, peach, pineapple, etc.). Examples of milk-processed foods include cheese, butter, yogurt, etc. Examples of meat-processed foods include pork cutlets, beef cutlets, chicken cutlets, sausages, sweet and sour pork, nuggets, neobiani, etc. Examples of noodles include dried noodles, plain noodles, ramen, udon noodles, Korean cold noodles, sealed and packed fresh noodles, etc. Additionally, the composition may be used for manufacturing retort foods, soups, etc.

As used herein, the term "functional food", which has the same meaning as the term "food for special health use (FoSHU)", refers to a food with high effects in medicinal and medical treatment, processed so as to efficiently exhibit a body modulating function as well as provide nutrients. The functional food may be manufactured in various forms including tablets, capsules, powders, granules, liquids, pills, etc., in order to obtain useful effects for the improvement of cancer.

Hereinafter, the present disclosure will be described in more detail with reference to the following examples. However, these examples are provided for illustrative purposes only but not intended to limit the scope of the present disclosure.

Example 1: Preparation of Metal Lactate Salt

Calcium carbonate, sodium carbonate, or potassium carbonate was reacted with lactate so as to obtain metal lactate salt (calcium lactate, sodium lactate, or potassium lactate) solutions, respectively. Each of them was filtered, dried, and pulverized so as to obtain metal lactate salt (calcium lactate, sodium lactate, or potassium lactate) in the form of powder. Then, the structure and binding energy of the obtained metal lactate salts (calcium lactate, sodium lactate, or potassium lactate) were analyzed (FIG. 1).

FIG. 1 shows a schematic diagram and a table comparing the structure and binding energy among calcium lactate, sodium lactate and potassium lactate, each having a molecular structure similar to that of calcium lactate. As can be seen in FIG. 1, it was confirmed that calcium lactate has relatively high binding energy as compared to sodium lactate and potassium lactate.

In the following, the experiments using calcium lactate having relatively high binding energy were conducted.

Example 2: Effect of Calcium Lactate on Tumor Microenvironment

After the treatment of a cancer cell with calcium lactate, the change in concentration of calcium, the change in concentration of lactate, and the change in pH in the cell were analyzed to predict the inflow levels of calcium lactate.

Example 2-1: Change in Calcium Level

Figure 2:
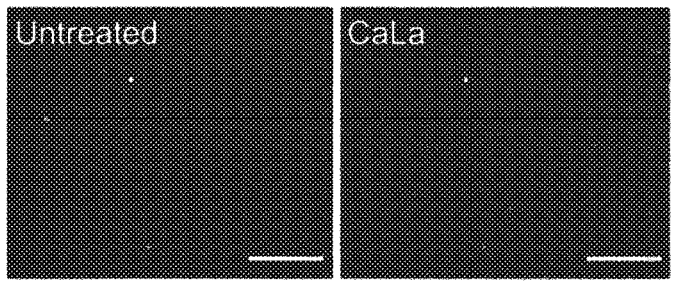
FIG. 2 provides fluorescence microscope images showing the result of comparing the calcium levels in cancer cells depending on whether or not treated with calcium lactate (CaLa).
Figure 2:
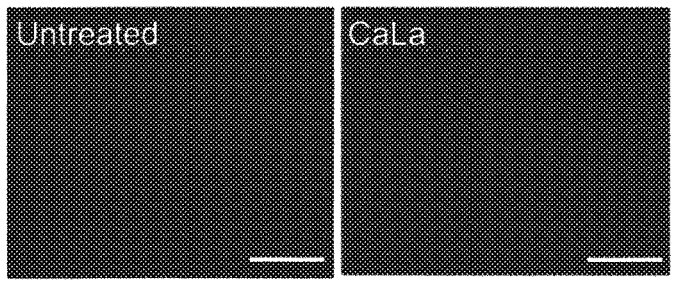

Each of human colorectal cancer cell lines (HCT-116 and HT-29) with the cell number of $5 \times 10^3$ cells cultured in a cancer cell culture medium (RPMI1640 medium including 10% FBS and 1% penicillin/streptomycin) at 37° C. with 5% $CO_2$ was treated with 2.5 mM calcium lactate and then cultured for 24 hours. The cultured cancer cells were treated with 10 µM Fluo-3/AM calcium indicator and 25% Pluronic F-127, reacted at 37° C. for 30 minutes, applied with fluorescence probes, and then photographed with a confocal microscope (FIG. 2). In this case, cancer cells untreated with calcium lactate were used as control groups.

FIG. 2 provides fluorescence microscope images showing the result of comparing the calcium levels in cancer cells depending on whether or not treated with calcium lactate (CaLa). As can be seen from FIG. 2, it was confirmed that the concentration of calcium was increased in cancer cells treated with calcium lactate.

Example 2-2: Change in Lactate Level

The cells cultured in Example 2-1 were cultured again in a medium including 3 mM (low) or 11 mM (normal) glucose. The cultured cells were disrupted by ultrasonication. The concentration of lactate included in the disrupted cells was measured using a lactate assay kit (AbCam, Cambridge, Mass.) (FIG. 3). In this case, cancer cells untreated with calcium lactate were used as control groups.

FIG. 3 is a graph showing the result of comparing the lactate levels in cancer cells depending on whether or not treated with calcium lactate (CaLa). As can be seen from FIG. 3, it was confirmed that regardless of the concentration of glucose included in the medium, the concentration of lactate was increased in the cancer cells treated with calcium lactate which was more apparent in the case of culturing the cells in a medium having high-concentration glucose.

Example 2-3: Change in pH Inside and Outside Cancer Cell

From the results shown in FIGS. 2 and 3, it was confirmed that in cases of treating a cancer cell with calcium lactate, the calcium lactate flows into the cancer cell. Then, it was checked whether or not the pH inside and outside the cancer cell is changed by the calcium lactate.

Specifically, with the cells cultured in Example 2-1, an extracellular pH was measured with a pH meter from the medium for the cells treated with calcium lactate and then cultured and an intracellular pH was measured with a pH detection kit (Life Technologies, CA) from the cells treated with calcium lactate and then cultured (FIG. 4). In this case, cancer cells untreated with calcium lactate were used as control groups.

FIG. 4 provides graphs showing the changes in intracellular and extracellular pH of cancer cells treated with calcium lactate, and the left graph shows the change in extracellular pH of the cancer cells and the right graph shows the change in intracellular pH of the cancer cells. As can be seen from FIG. 4, it was confirmed that in case of treating the cells with calcium lactate, the extracellular pH was not changed but the intracellular pH was decreased to acidic condition. As can be seen from the left graph of FIG. 4, calcium lactate itself did not change the pH outside the cancer cell but when the calcium lactate flowed into the cancer cell, the pH was decreased, and, thus, the intracellular environment of the cancer cell was changed by the inflow of calcium lactate.

Example 3: Effect of Calcium Lactate on Expression of Cancer Growth Factor

From the result of Example 2, it was confirmed that the intracellular environment of a cancer cell can be changed by calcium lactate. Therefore, in order to check whether such a change causes a change in the growth of a cancer cell, the expression levels of β-catenin, which is one of the cancer growth factors, was checked at the gene and protein expression level, depending on the treatment with calcium lactate, in a colorectal cancer or breast cancer cell line.

Example 3-1: Effect of Calcium Lactate on Expression Levels of β-Catenin in Colorectal Cancer Cell Line Human colorectal cancer cell lines (HCT-116, HT-29, and DLD-1) were cultured by the same method as that of Example 2-1 except that they were treated with 0 mM, 1.5 mM, or 2.5 mM calcium lactate, and the cultured cancer cells were obtained. Then, expression levels of β-catenin depending on the concentration of calcium lactate were compared at the expression levels of mRNA and protein included therein.

Firstly, in order to compare mRNA expression levels, the total RNA was extracted from each of the cancer cells using an RNeasy mini kit and cDNA was synthesized using a reverse transcriptase. The gene of β-catenin was obtained through reverse transcriptase PCR using the synthesized cDNA as a template and the primers described below.

```
                                    (SEQ ID NO: 1)
β-catenin F:    5'-AAAATGGCAGTGCGTTTAG-3'

(SEQ ID NO: 2)
β-catenin R:    5'-TTTGAAGGCAGTCTGTCGTA-3'

(SEQ ID NO: 3)
ACTIN F:        5'-AAC-TGGAACGGTGAAGGT-3'

(SEQ ID NO: 4)
ACTIN R:        5'-CCTGTAACAACGCATCTCAT-3'
```

The upper part of FIG. 5 provides electrophoretic images showing the result of comparing mRNA expression levels of β-catenin in human colorectal cancer cell lines (HCT-116, HT-29, and DLD-1) treated with calcium lactate at various concentrations, and the lower part of FIG. 5 provides Western blotting images showing the result of comparing protein expression levels of β-catenin in human colorectal cancer cell lines (HCT-116, HT-29, and DLD-1) treated with calcium lactate at various concentrations. As can be seen from the upper part of FIG. 5, there was no difference at the mRNA expression levels of β-catenin, depending on the concentration of calcium lactate.

Then, in order to compare protein expression levels, each of the cancer cells was disrupted and electrophoresis was performed thereto. Then, a Western blot using anti-β-catenin antibody as a primary antibody and an anti-rabbit IgG conjugate as a secondary antibody was conducted (lower part of FIG. 5) and the blots were analyzed with the Image-J program. In this case, actin was used as internal control groups.

The upper part of FIG. 5 provides electrophoretic images showing the result of comparing mRNA expression levels of β-catenin in human colorectal cancer cell lines (HCT-116, HT-29, and DLD-1) treated with calcium lactate at various concentrations, and the lower part of FIG. 5 provides Western blotting images showing the result of comparing protein expression levels of β-catenin in human colorectal cancer cell lines (HCT-116, HT-29, and DLD-1) treated with calcium lactate at various concentrations. As can be seen from the lower part of FIG. 5, it was confirmed that as the concentration of calcium lactate is increased, the protein expression levels of β-catenin is decreased unlike the mRNA expression levels of β-catenin.

Therefore, it was confirmed that calcium lactate flowing into a cancer cell changes the intracellular environment of the cancer cell and thus expression of β-catenin, which is a cancer growth factor, is suppressed at the gene decoding level.

Example 3-2: Effect of Calcium Lactate on Expression Levels of β-Catenin in Breast Cancer Cell Line Using the same method as that of Example 3-1 the expression levels of f-catenin and activated β-catenin depending on the concentration of calcium lactate were compared at the protein expression level (FIG. 6) with a human breast cancer cell line (MCF-7) cultured in a cancer cell culture medium (RPMI1640 medium including 10% FBS and 1% penicillin/streptomycin) at 37° C. with 5% $CO_2$ and a human breast cancer cell line (MDA-MB-231) cultured in another cancer cell culture medium (DMEM medium including 10% FBS and 1% penicillin/streptomycin) at 37° C. with 5% $CO_2$.

FIG. 6 provides Western blotting images showing the result of comparing protein expression levels of the total β-catenin and activated β-catenin in human breast cancer cell lines (MCF-7 and MDA-MB-231) treated with calcium lactate at various concentrations. As can be seen from FIG. 6, it was confirmed that as the concentration of calcium lactate is increased, the protein expression levels of both the β-catenin and the activated β-catenin are decreased.

Example 4: Effect of Calcium Lactate on Cancer Energetics

Through Example 2, it was confirmed that when a cancer cell line is treated with calcium lactate, the concentration of calcium lactate in the cancer cell line is increased. Then, it was checked whether or not the increased lactate changes lactate synthesis.

Human colorectal cancer cell lines (HCT-116 and HT-29) were cultured under normoxia or hypoxia condition. The cell lines cultured under the hypoxia condition were treated with calcium lactate, and then, expression levels of GLUT 1 and HK2 in each of the cultured cell lines were compared at the mRNA and protein expression levels (FIG. 7).

FIG. 7 is a real-time PCR and a western blot showing the effect of calcium lactate in the cancer cell line under hypoxic conditions. The graph shows mRNA expression levels of glucose transporter (GLUT)-1 and hexokinase (HK)2, which involved in the early stage of glycolysis and western blotting images showing protein expression levels of HK2. As can be seen from FIG. 7, it was confirmed that under the hypoxia condition, the expression levels of GLUT 1 and HK2 acting in the early stage of glycolysis are increased and as a result the glycolysis is activated but treating the cell lines with calcium lactate the activation was reduced.

Example 5: Analysis of Stabilization of Cancer Gene Caused by Calcium Lactate

It was checked whether or not the treatment with calcium lactate causes a change in expression levels of poly(ADP-ribose) polymerase (PARP) which plays an important role in maintaining the integrity of DNA as a part of a base excision route repairing damaged genes.

Example 5-1: Effect of Calcium Lactate on Expression Levels of PARP in Breast Cancer Cell Line Human breast cancer cell lines (MCF-7 and MDA-MB-231) were cultured by the same method as that of Example 2-1 except that they were treated with 0 mM, 2.5 mM, or 5.0 mM calcium lactate, and the cultured cancer cells were obtained. Then, changes in expression level depending on the concentration of calcium lactate was analyzed at the protein expression levels of PARP included therein (FIG. 8). In this case, the change in expression level was analyzed through a Western blot using the Image-J program with anti-PARP antibody as a primary antibody and anti-rabbit IgG conjugate as a secondary antibody, and GAPDH was used as internal control groups.

FIG. 8 provides Western blotting images showing the effects of calcium lactate on protein expression levels of PARP and cleaved PARP expressed in human breast cancer cell lines (MCF-7 and MDA-MB-231). As can be seen from FIG. 8, it was confirmed that as the concentration of calcium lactate is increased, the protein expression levels of PARP in each of the breast cancer cell lines (MCF-7 and MDA-MB-231) is decreased. Meanwhile, the protein expression levels of the truncated PARP is increased in the MCF-7 cell line. Therefore, it was confirmed that calcium lactate not only stops glycolysis in a cancer cell but also induces apoptosis of a cancer cell by stopping glycolysis and thus can be used as an anticancer drug.

Example 5-2: Effect of Calcium Lactate on Expression Levels of PARP in Colorectal Cancer Cell Line The protein expression levels of PARP expressed in the colorectal cancer cell line were compared (FIG. 9) after a human colorectal cancer cell line (HCT-116) was treated individually or in combination for 24 hours with 5 mM calcium lactate, 5-indane sulfonamide (IS) as an inhibitor of carbonic anhydrase, or cinnamic acid (CA) as an inhibitor of MCT-4 which is a pathway of lactate. In this case, an untreated cancer cell line was used as a control group.

FIG. 9 provides a Western blotting image and a graph showing the result of comparing protein expression levels of PARP in colorectal cancer cell lines treated with calcium lactate, 5-indane sulfonamide (IS) as an inhibitor of carbonic anhydrase, or cinnamic acid (CA) as an inhibitor of MCT-4, which is a pathway of lactate outflow, individually or in combination. As can be seen from FIG. 9, it was confirmed that in case of the treatment with each of the above-described materials alone, the protein expression levels of PARP is decreased, only when the human colorectal cancer cell line is treated with calcium lactate alone. However, it was confirmed that when the human colorectal cancer cell line is treated with combination of two inhibitors while not treating with calcium lactate, the protein expression levels of PARP is decreased, and when the colorectal cancer cell line is treated in combination with each inhibitor and calcium lactate, the protein expression levels of PARP was decreased further, and when the human colorectal cancer cell line is treated in combination with all three materials, PARP is not detected in a cell.

Example 5-3: Effect of Calcium Lactate on Expression Levels of PARP in Melanoma Cell Line Each of human melanoma cell lines (SKMEL-02 and SKMEL-28) cultured in a cancer cell culture medium (RPMI1640 medium including 10% FBS and 1% penicillin/streptomycin) at 37° C. with 5% $CO_2$ was treated with 0 mM, 0.5 mM, 1.0 mM, 2.5 mM, 5.0 mM, or 10 mM calcium lactate for 12 hours. Then, protein expression levels of PARP expressed in the melanoma cell lines were compared (FIG. 10).

FIG. 10 provides Western blotting images showing the result of comparing protein expression levels of PARP in human melanoma cell lines (SKMEL-02 and SKMEL-28) treated with calcium lactate at various concentrations. As can be seen from FIG. 10, it was confirmed that the protein expression levels of PARP in the melanoma cell lines are also decreased as the concentration of calcium lactate is increased.

Example 6: Effect of Calcium Lactate on Lactate-Related Metabolism in Cancer Cell From the results shown in FIGS. 2 and 4, it was confirmed that when calcium lactate flows in a cancer cell, the concentration of lactate in the cell is increased, and, thus, energy supply through glycolysis may not be normally performed.

Then, an effect of lactate on intracellular metabolism caused by the treatment with calcium lactate was examined.

Example 6-1: Effect of Calcium Lactate on Protein Expression Levels of LDH-B (Lactate Dehydrogenase B)

The effect of calcium lactate on protein expression levels of LDH-B (lactate dehydrogenase B), which is an enzyme for converting lactate into pyruvate, was examined.

Human colorectal cancer cell lines (HCT-116 and HT-29) were treated with 2.5 mM calcium lactate and cultured for 24 hours. The cultured cancer cell lines were immobilized with 4% paraformaldehyde and treated with an anti-rabbit LDHB antibody for 15 hours. Then, the cancer cell lines were washed with PBS and treated with a secondary antibody conjugated with biotin and then reacted at room temperature for 2 hours. Then, the cancer cell lines were treated with streptavidine conjugated with FITC to perform fluorescence staining and then photographed with a fluorescence microscope (FIGS. 11a-11c). In this case, cancer cell lines cultured under normoxia condition (N-control) or hypoxia condition (H-control) were used as control groups, and a nucleus of each cell was stained using DAPI. Further, the photos were analyzed using the Xenogen In Vivo Imaging System 100 series and Living imaging software (Xenogen).

FIG. 11a provides fluorescence microscope images showing the changes in protein expression levels of LDH-B in cancer cell lines depending on the treatment with calcium lactate. FIG. 11b provides fluorescence microscope images showing the fluorescence absorbance of cancer cell line depending on the treatment with calcium lactate. FIG. 11c provides quantitative analysis graph showing fluorescence development levels depending on the protein expression levels of LDH-B. As can be seen from FIGS. 11a-11c, it was confirmed that the protein expression levels of LDH-B in the cells treated with calcium lactate are sharply increased.

Example 6-2: Effect of Calcium Lactate on Pyruvate Level

From the result of Example 6-1, it was confirmed that the protein expression levels of LDH-B in a cancer cell is increased by treating with calcium lactate. Then, the effect of calcium lactate on the intracellular expression levels of pyruvate produced by the LDH-B was examined.

Each of human colorectal cancer cell lines (HCT-116 and HT-29) with the cell number of $5 \times 10^5$ cells was treated with 2.5 mM calcium lactate for 24 hours and the cells were disrupted by ultrasonication and filtered using a 10 kDa filter so as to obtain filtrate. The obtained filtrate was applied to a pyruvate assay kit (Abcam, Cambridge, Mass.) to measure the concentration of pyruvate included in the filtrate (FIG. 12).

FIG. 12 is a graph showing changes of pyruvate concentrations in cancer cells depending on the treatment with calcium lactate. As can be seen from FIG. 12, it was confirmed that the pyruvate levels in the cells treated with calcium lactate are sharply increased.

Example 6-3: Effect of Calcium Lactate on Protein Expression Levels of PDH (Pyruvate Dehydrogenase)

From the result of Example 6-2, it was confirmed that a pyruvate level in a cancer cell is increased by treating with calcium lactate. Then, an effect of calcium lactate on a protein expression levels of PDH (pyruvate dehydrogenase), which is an enzyme for converting the pyruvate into a TCA cycle, was examined.

After the same method as that of Example 6-1 except that an anti-rabbit PDH antibody was used instead of the anti-rabbit LDHB antibody was performed, protein expression levels of PDH in human colorectal cancer cell lines (HCT-116 and HT-29) treated with calcium lactate were measured (FIG. 13).

FIG. 13a provides fluorescence microscope images showing changes in protein expression levels of PDH in cancer cell lines depending on the treatment with calcium lactate. FIG. 13b provides a quantitative analysis graph showing fluorescence development levels of PDH depending on the treatment with calcium lactate. As can be seen from FIGS. 13a and 13b, it was confirmed that the protein expression levels of PDH in the cells treated with calcium lactate are sharply increased.

Example 6-4: Effect of Calcium Lactate on α-KG (α-Ketoglutarate) Level

From the result of Example 6-3, it was confirmed that a protein expression levels of PDH in a cancer cell is increased by treating with calcium lactate. Then, the effect of calcium lactate on an intracellular levels of α-KG (α-ketoglutarate) produced by the TCA cycle activated by the PDH was examined. The α-KG can be synthesized by glutamine in a medium. Thus, in this case, cancer cell lines cultured in a normal medium or a glutamine-free medium were used.

Cancer cell lines with the cell number of $5 \times 10^5$ cells cultured in a normal medium or a glutamine-free medium were treated with 2.5 mM calcium lactate for 24 hours and the cells were disrupted by ultrasonication and filtered using a 10 kDa filter so as to obtain filtrate. The obtained filtrate was applied to an α-Ketoglutarate assay kit (BioVision, Exton, Pa.) to measure the concentration of α-KG included in the filtrate (FIGS. 14a and 14b).

FIG. 14a provides a quantitative analysis graphs showing the changes in concentration of α-KG in cancer cell lines with calcium lactate treatment under normal medium. FIG. 14b provides a quantitative analysis graph showing the changes in concentration of α-KG in cancer cell lines with calcium lactate treatment under glutamine-free medium. As can be seen from FIGS. 14a and 14b, it was confirmed that if the cancer cell lines cultured in the normal medium or in the glutamine-free medium are treated with calcium lactate, the α-KG levels in the cells are sharply increased.

Summing up the results of Examples 6-1 to 6-4, it can be seen that in a cancer cell treated with calcium lactate, levels of LDH-B for converting lactate into pyruvate, pyruvate produced by the LDH-B, PDH (pyruvate dehydrogenase) for converting the pyruvate into a TCA cycle, and α-KG produced by the TCA cycle activated by the PDH are increased.

Example 7: Effect of Calcium Lactate on Cancer Cell Metastasis, Invasion, and Expression Levels of Angiogenesis Factor From the result of Example 6, it was confirmed that in a cancer cell treated with calcium lactate, an α-KG levels is increased. Then, effects of calcium lactate on expression levels of factors affecting metastasis, invasion, and angiogenesis of a cancer cell of which a protein expression levels is regulated by the α-KG were examined.

Example 7-1: Effect of Calcium Lactate on Protein Expression Levels of HIF-1α(Hypoxia Inducible Factor 1α)

The effect of calcium lactate on protein expression levels of HIF-1α (hypoxia inducible factor 1α) known as a cancer cell metastasis factor was examined.

Human colorectal cancer cell lines (HCT-116 and HT-29) were cultured for 24 hours, under normoxia or hypoxia condition either treated or not treated with 2.5 mM calcium lactate. Then, a Western blot using an anti-HIF-1α antibody was conducted to each of the cultured cancer cell lines (upper part of FIG. 15).

The upper part of FIG. 15 provides Western blotting images showing the protein expression levels of HIF-1α expressed in human colorectal cancer cell lines (HCT-116 and HT-29) cultured for 24 hours with or without the treatment with 2.5 mM calcium lactate under normoxia or hypoxia condition. As can be seen from the upper part of FIG. 15, it was confirmed that HIF-1α is expressed under hypoxia condition, but if the cancer cell lines are treated with calcium lactate, HIF-1α is not expressed even under hypoxia condition.

Then, the human colorectal cancer cell lines (HCT-116 and HT-29) were treated with various concentrations (0.5 mM, 1.5 mM and 2.5 mM) of the calcium lactate under hypoxia condition and cultured and change in expression levels of HIF-1α in a nucleus of a cancer cell was measured (lower part of FIG. 15).

The lower part of FIG. 15 provides Western blotting images showing a protein expression levels of HIF-1α expressed in human colorectal cancer cell lines (HCT-16 and HT-29) cultured for 24 hours with the treatment of 0.5 mM, 1.5 mM and 2.5 mM calcium lactate under hypoxia condition. As can be seen from the lower part of FIG. 15, it was confirmed that the calcium lactate suppresses the expression levels of HIF-1α concentration dependently.

Example 7-2: Effect of Calcium Lactate on Expression Levels of VEGF (Vascular Endothelial Growth Factor)

From the result of Example 7-1, it was confirmed that calcium lactate suppresses the expression levels of HIF-1α concentration dependently. Then, the effect of calcium lactate on expression levels of a VEGF (vascular endothelial growth factor) known as a cancer cell invasion factor of which expression is regulated by the HIF-1α was examined.

Human colorectal cancer cell lines (HCT-116 and HT-29) were treated with 2.5 mM calcium lactate under hypoxia condition and cultured for 24 hours. Then, mRNA expression levels and protein expression levels of VEGF in each of the cultured cancer cell lines were analyzed (FIGS. 16a and 16b). In this case, human colorectal cancer cell lines cultured without treating with calcium lactate under normoxia or hypoxia condition were used as control groups.

FIG. 16a provides graphs showing the result of measurement of an mRNA expression levels and a protein expression levels (FIG. 16b) of VEGF expressed in human colorectal cancer cell lines (HCT-116 and HT-29) cultured for 24 hours with or without the treatment with 2.5 mM calcium lactate under normoxia or hypoxia condition. As can be seen from FIGS. 16a and 16b, it was confirmed that a VEGF level is sharply increased under hypoxia condition, but if the cancer cell lines are treated with calcium lactate, the increased VEGF level is decreased.

Example 7-3: Effect of Calcium Lactate on Cancer Cell-Derived Factor Causing Tube Formation of Human Vascular Endothelial Cell (HUVEC)

In order to confirm the effect of calcium lactate on angiogenesis, the effect of calcium lactate on the factor secreted from a cancer cell which can induce tube formation of a human vascular endothelial cell (HUVEC) was examined.

Cancer cell lines cultured in RPMI-1640 medium added with 1% FBS were treated with 0.5 mM, 1 mM, 1.5 mM, and 2.5 mM calcium lactate for 24 hours and culture supernatants were obtained therefrom. A human vascular endothelial cell (HUVEC) was inoculated into each of the obtained culture supernatant and cultured to analyze a conformational change of cells (FIG. 17). In this case, an HUVEC cultured using the culture medium of a cancer cell line cultured without treating with calcium lactate was used as a control group, and an HUVEC cultured with the treatment with Sulforaphane, which is a growth inhibitor of an HUVEC, was used as a comparison group.

FIG. 17 is fluorescence images showing the tube formation levels in human vascular endothelial cells (HUVEC) treated with calcium lactate at various concentrations. The HUVEC was cultured using the medium of cultured cancer cell lines with different concentrations of calcium lactate. As can be seen from FIG. 17, it was confirmed that as compared with the control group showing an excellent tube-forming ability, the HUVECs cultured using the culture supernatants of the cancer cell lines treated with calcium lactate showed reduced tube-forming ability as the concentration of calcium lactate is increased, and the HUVEC cultured in the culture supernatant of the cancer cell line treated with 2.5 mM calcium lactate showed reduced tube-forming ability similar to the comparison group treated with Sulforaphane. It was confirmed that since the angiogenesis of the HUVEC is induced by a factor secreted from a cancer cell, calcium lactate has concentration dependent inhibiting activity of the factor inducing angiogenesis.

Summing up the results of Examples 7-1 to 7-3, it can be seen that calcium lactate has an effect of inhibiting expression of HIF-1α known as a cancer cell metastasis factor and VEGF known as a cancer cell invasion factor and also has an effect reducing angiogenesis.

Example 8: Effect of Calcium Lactate on Metastasis and Invasion of Cancer Cell Line From the result of Example 7, it was confirmed that calcium lactate has an effect of inhibiting expression of HIF-1α known as a cancer cell metastasis factor and VEGF known as a cancer cell invasion factor and also has an effect of inhibiting the activity of a factor inducing angiogenesis. Then, actual effects of calcium lactate on metastasis and invasion of a cancer cell were examined by analyzing migration of the cancer cell.

Example 8-1: Effect of Calcium Lactate on Metastasis and Invasion of Colorectal Cancer Cell Line A colorectal cancer cell line HCT-116 with the cell number of $4 \times 10^5$ cells was inoculated into a culture container at the center of which an ibidi culture insert having a thickness of 500 μm was placed, and treated with 2.5 mM calcium lactate and then cultured for 24 hours. Then, the insert was removed and further cultured for 12 hours to analyze migration of the cancer cells to a site where the insert was removed using a JuLi Br, Live cell analyzer (NanoEnTek Inc., South Korea) (FIG. 18). In this case, a colorectal cancer cell line cultured without treating with calcium lactate was used as a control group.

FIG. 18 provides photos showing the result confirming cell migration, which shows metastatic capacity of a colorectal cancer cell line, depending on whether or not treated with calcium lactate. As can be seen from FIG. 18, it was confirmed that in the colorectal cancer cell line treated with calcium lactate, cell migration is decreased, whereas in the colorectal cancer cell line of the control group untreated with calcium lactate, cell migration is maintained.

Example 8-2: Effect of Calcium Lactate on Metastasis and Invasion of Breast Cancer Cell Line Using the same method as Example 8-1, with breast cancer cell lines (MCF-7 and MDA-MB231) instead of the colorectal cancer cell line, an effect of calcium lactate on migration of the breast cancer cell lines was examined (FIG. 19).

FIG. 19 provides photos showing the result of confirming cell migration, which shows metastatic capacity of a breast cancer cell line, depending on whether or not treated with calcium lactate. As can be seen from FIG. 19, it was confirmed that as compared with the breast cancer cell lines of the control groups untreated with calcium lactate, the breast cancer cell lines treated with calcium lactate show relatively low levels of metastasis.

Example 8-3: Effect of Calcium Lactate on Metastasis and Invasion of Melanoma Cell Line Using the same method as Example 8-1, with melanoma cell lines (SKMEL-02 and SKMEL-28) instead of the colorectal cancer cell line and further cultured for 24 hours after removal of the insert was performed, the effect of calcium lactate on migration of the melanoma cell lines was examined (FIG. 20).

FIG. 20 provides photos showing the result confirming cell migration, which shows metastatic capacity of a melanoma cell line, depending on whether or not treated with calcium lactate. As can be seen from FIG. 20, it was confirmed that as compared with the melanoma cell lines of the control groups untreated with calcium lactate, the melanoma cell lines treated with calcium lactate show relatively low levels of metastasis.

Summing up the results of Examples 8-1 to 8-3, it can be seen that calcium lactate can inhibit metastasis of all cancer cells such as colorectal cancer, breast cancer, and melanoma cells.

Example 9: Effect of Calcium Lactate on Viability of Cancer Cell Line

The effect of calcium lactate on viability of breast cancer cell lines, colorectal cancer cell lines, and melanoma cell lines were examined.

Example 9-1: Effect of Calcium Lactate on Viability of Breast Cancer Cell Line

Breast cancer cell lines (MCF-7 and MDA-MB231) were cultured for 24 hours with or without treating with 2.5 mM calcium lactate. Each of the breast cancer cell lines were treated with 5 μl of FITC Annexin V and 5 μl of PI and reacted at room temperature for 15 minutes and then, a flow cytometry analysis was conducted thereto using a FACS Calibur (BD Bioscience, USA) to evaluate staining thereof and thus measure a cancer cell apoptosis rate (FIGS. 21a-21f).

FIGS. 21a and 21d provide photos showing the result of confirming cell migration, which shows metastatic capacity of a breast cancer cell line depending on whether or not treated with calcium lactate for MCF-7 cell line and MDA-MB231 cell line, respectively. FIGS. 21b, 21c, 21e, and 21f provide the result of a flow cytometry analysis showing changes in survival rate. As can be seen from FIGS. 21b and 21c, it was confirmed that the MCF-7 cell line shows a cell apoptosis rate of 9.63% before treating with calcium lactate but shows a cell apoptosis rate of 33.8% after treating with calcium lactate, and the MDA-MB231 cell line (FIGS. 21e and 21f) shows a cell apoptosis rate of 10.17% before the treating with calcium lactate but shows a cell apoptosis rate of 13.05% after treating with calcium lactate.

Therefore, it can be seen that if the breast cancer cell lines are treated with calcium lactate, a cell apoptosis rate is increased.

Example 9-2: Effect of Calcium Lactate on the Conformational Change of Colorectal Cancer Stem Cell Line A human colorectal cancer stem cell line was inoculated into a stem cell culture medium (medium including 1% penicillin/streptomycin and 50 times B27 and including a DMEM medium and an F12 medium mixed at 1:1) and cultured at 37° C. with 5% $CO_2$. The cultured colorectal cancer stem cell line was treated with calcium lactate and then, it was checked whether or not there is the conformational change of a sphere formed by the stem cells (FIG. 22). In this case, a cancer cell treated with DMSO instead of calcium lactate was used as a control group.

FIG. 22 provides microscopic images showing the conformational change of a sphere depending on the treatment of a colorectal cancer stem cell line constituting the sphere with calcium lactate. As can be seen from FIG. 22, it was confirmed that in the control group which was not treated with calcium lactate a sphere is maintained but after treating with calcium lactate, the conformation of the sphere is destructed, thereby confirming the reduced the viability of the colorectal cancer stem cells.

Example 9-3: Effect of Calcium Lactate on Colony-Forming Ability of Cancer Cell Line Firstly, human colorectal cancer cell lines (HCT-116, HT-29, and DLD-1) were inoculated into solid mediums including various concentrations (0 mM, 0.5 mM, 1.5 mM, or 2.5 mM) of calcium lactate and cultured for 10 days. After the completion of the culture, the cells were immobilized and stained with hematoxylin. Then, the number of cancer cells formed into colonies was counted (FIG. 23).

FIG. 23 provides photos and graphs (left: HCT-116, middle: HT-29, right: DLD-1) showing the result comparing the colony-forming ability of colorectal cancer cell lines depending on treating with calcium lactate. As can be seen from FIG. 23, it was confirmed that all the colorectal cancer cell lines untreated with calcium lactate form 260 to 360 colonies but the number of colonies decreased as the concentration of calcium lactate increased, and in the case of treating the colorectal cancer cell lines with 2.5 mM calcium lactate, only 100 to 120 colonies are formed.

Then, using the same method as described above, human melanoma cell lines (SKMEL-02 and SKMEL-28) were inoculated into solid mediums including various concentrations (1 mM, 2.5 mM, or 5 mM) of calcium lactate and culture was performed, and the number of cancer cells formed into colonies were counted (FIGS. 24a and 24b).

FIGS. 24a and 24b provides graphs and tables showing the result comparing the colony-forming ability of melanoma cell lines depending on treating with calcium lactate. As can be seen from FIGS. 24a and 24b, it was confirmed that the human melanoma cell lines untreated with calcium lactate form 105 to 168 colonies but the number of colonies decreased as the concentration of calcium lactate increased, and in the case of treating the SKMEL-28 cell line with 5 mM calcium lactate, colony was not formed and in the case of treating the SKMEL-02 cell line with 5 mM calcium lactate, about 49 colonies are formed.

Summing up the result, it can be seen that calcium lactate has an effect of inhibiting the colony-forming ability of colorectal cancer and melanoma cell lines.

Example 9-4: Effect of Combination of Calcium Lactate with Material Having Anticancer Activity on Viability of Cancer Cell Line Semi drug agarose based plate including 5 mM calcium lactate or the materials known as having an anticancer activity (1 mM IS (5-indane sulfonamide) or 5 mM CA (cinnamic acid)) individually or in combination were prepared. Then, a human colorectal cancer cell line HCT-116 was inoculated into each of the prepared plate and cultured for 10 days. Then, survival rates of the cells were compared (FIGS. 25a & 25b).

FIGS. 25a and 25b provides graphs showing the result of comparing the survival rate of colorectal cancer cell lines treated individually or in combination with calcium lactate, 5-indane sulfonamide (IS) as an inhibitor of carbonic anhydrase or cinnamic acid (CA) as an inhibitor of MCT-4 which is a pathway of lactate outflow. As can be seen from FIGS. 25a and 25b, it was confirmed that the survival rates of the colorectal cancer cell line treated with the calcium lactate or the materials known as having an anticancer activity (IS or CA) individually were decreased to about 60% and the survival rates of the colorectal cancer cell line treated with the calcium lactate in combination with IS or CA or both were further decreased to about 10% to 30%.

Example 9-5: Effect of Calcium Lactate on Viability of Cancer Cell Line with Decreased Cell Adhesivity Human colorectal cancer cell lines (HCT-116, HT-29, and DLD-1) were inoculated into a 6-well plate with low adhesivity and then cultured treating with various concentrations (0 mM, 1.5 mM, or 2.5 mM) of calcium lactate. Then, survival rates of the cells were compared (FIG. 26).

FIG. 26 provides graphs showing the result comparing the effects of calcium lactate on a survival rate of colorectal cancer cell lines cultured in a culture container with low adhesivity. As can be seen from FIG. 26, it was confirmed that if the colorectal cancer cell lines cultured in a culture medium with low adhesivity are not treated with calcium lactate, the cell apoptosis rate is very low (about 5%), but if they are treated with calcium lactate, the cell apoptosis rate is sharply increased (about 90%).

Summing up the results of Examples 9-1 to 9-5, it can be seen that calcium lactate can decrease the survival rates of all cancer cells such as colorectal cancer and melanoma cells.

Example 10: Verification of Effect of Calcium Lactate Using Animal Model

Example 10-1: Setting of Experimental Group Using Animal Model

A colorectal cancer cell (HT-29) cultured in an RPMI1640 medium and then diluted with PBS was subcutaneously implanted into the flank of Balb/c mice. The mice were bred until the colorectal cancer cell grew to about 5 mm. Then, four groups were set up; a control group untreated with calcium lactate for 30 days, an experimental group 1 (peroral, P.O.) administered with 2.5 mM calcium lactate by oral administration, an experimental group 2 (intra tumor, I.T.) injected with 2.5 mM calcium lactate around tumor, and an experimental group 3 (subcutaneous, S.C.) subcutaneously injected with 25 mM calcium lactate (FIG. 27).

FIG. 27 is a schematic illustration of experimental scheme for calcium lactate treatment using animal models.

Example 10-2: Change in Expression Levels of PARP

Colorectal cancer tissues were extracted from the mice of the control group, the experimental group 1, or the experimental group 2 set up in Example 10-1, and expression levels of PARP and truncated PARP contributing to stabilization of cancer cells expressed therein were compared (FIG. 28).

FIG. 28 is a picture showing the change in expression levels of PARP proteins extracted from the tumor tissue of the xenograft animal model depending on treatment method of calcium lactate, and whether or not treated with calcium lactate. As can be seen from FIG. 28, it was confirmed that in the experimental groups treated with calcium lactate in different manners as compared with the control group untreated with calcium lactate, PARP degrading activity is increased.

Example 10-3: Change in Expression Levels of HIF-1α and VEGF in Animal Model Administered with Calcium Lactate by Oral Administration Colorectal cancer tissues were extracted from the mice of the control group or the experimental group 1 set up in Example 10-1, and expression levels of HIF-1α and VEGF involved in metastasis, invasion, and angiogenesis of tumor expressed therein were compared (FIG. 29). In this case, GAPDH was used as internal control groups.

FIG. 29 provides photos showing the change in expression levels of HIF-1α or GAPDH depending on whether or not treated with calcium lactate, in proteins extracted from tumor tissues of the animal models in which calcium lactate was orally administered. As can be seen from FIG. 29, it was confirmed that the expression of the HIF-1α and the VEGF is inhibited in the experimental group 1 treated with calcium lactate as compared with the control group untreated with calcium lactate.

Example 10-4: Change in the Tumor Size in Animal Model Administered with Calcium Lactate by Oral Administration The volumes of colorectal cancer tissues extracted from the mice of the control group or the experimental group 1 set up in Example 10-1 were measured over time and compared with each other (FIG. 30).

FIG. 30 is a graph showing the change in tumor volume depending on whether or not treated with calcium lactate in an animal model in which with 2.5 mM calcium lactate was orally administrated. As can be seen from FIG. 30, the final tumor volume of the control group untreated with calcium lactate is about 1200 mm$^3$×10$^3$, whereas that of the experimental group 1 treated with calcium lactate is about 480 mm$^3$×10$^3$. Therefore, it can be seen that calcium lactate has an effect of inhibiting the growth of tumor.

Example 10-5: Change in Expression Levels of HIF-1α and VEGF in Animal Models Injected with Calcium Lactate Colorectal cancer tissues were extracted from the mice of the control group or the experimental group 2 set up in Example 10-1, and expression levels of HIF-1α and VEGF involved in metastasis, invasion, and angiogenesis of tumor therein were compared (FIG. 31). In this case, GAPDH was used as internal control groups.

FIG. 31 provides western blots showing the change in the expression levels of HIF-1α or GAPDH in the protein extracted from tumor tissues of the xenograft animal model depending on whether or not treated with calcium lactate around the tumor. As can be seen from FIG. 31, it was confirmed that in the experimental group 2 treated with calcium lactate as compared with the control group untreated with calcium lactate, expression of the HIF-1α and the VEGF is inhibited.

Example 10-6: Change in Tumor Size in Animal Model Injected with Calcium Lactate The volumes of colorectal cancer tissues extracted from the mice of the control group or the experimental group 2 set up in Example 10-1 were measured over time and compared with each other (FIG. 32).

FIG. 32 provides a graph showing the change in tumor volume depending on whether or not treated with 2.5 mM calcium lactate around a tumor. As can be seen from FIG. 32, it was confirmed that the final tumor volume of the control group untreated with calcium lactate is about 1200 mm$^3$× 10$^3$, whereas that of the experimental group 2 treated with calcium lactate is about 490 mm$^3$×10$^3$. Therefore, it can be seen that calcium lactate has an effect of inhibiting the growth of tumor.

Example 10-7: Change in Tumor Morphology of Animal Model Depending on Treatment with Calcium Lactate The tumor morphologies of the mice of the control group or the experimental group 2 set up in Example 10-1 were compared with each other (FIG. 33).

FIG. 33 provides photos showing the change in tumor morphology of an animal model depending on the injection of 2.5 mM calcium lactate around tumor. As can be seen from FIG. 33, it was confirmed that the tumor photographed from the control group untreated with calcium lactate has a large size with increased angiogenesis in its surface, whereas the tumor photographed from the experimental group is decreased in size with decreased angiogenesis.

Example 10-8: Change in Tumor Size in Animal Model Subcutaneously Injected with Calcium Lactate The volumes of colorectal cancer tissues extracted from the mice of the control group or the experimental group 3 set up in Example 10-1 were measured over time and compared with each other (FIG. 34).

FIG. 34 is a graph showing the change in tumor volume depending on whether or not treated with calcium lactate in an animal model in which 25 mM calcium lactate was subcutaneously injected around the nape. As can be seen from FIG. 34, it was confirmed that the final tumor volume of the control group untreated with calcium lactate is about 2300 mm$^3$, whereas that of the experimental group 3 treated with calcium lactate is about 80 mm$^3$. Therefore, it can be seen that 25 mM calcium lactate has an effect of inhibiting the growth of tumor.

Example 10-9: Change in Tumor Morphology of Animal Model Depending on Treatment with Calcium Lactate The tumor morphologies of the mice of the control group or the experimental group 3 set up in Example 10-1 were compared with each other (FIG. 35).

FIG. 35 provides photos showing the change in tumor morphology in an animal model depending on the treatment with 25 mM calcium lactate. As can be seen from FIG. 35, it was confirmed that the tumor photographed from the control group untreated with 25 mM calcium lactate has larger size with increased angiogenesis in its surface, whereas the tumor photographed from the experimental group 3 is greatly decreased in size and angiogenesis is also reduced. Therefore, summing up the results of Examples 10-1 to 10-9, calcium lactate with a concentration of 2.5 mM to 25 mM showed an excellent anticancer activity in an animal model.

Example 11: Effect of Treating Colorectal Cancer by Radiation in Combination with Administration of Calcium Lactate In Examples 10-2, 10-3, and 10-5, it was confirmed that expression of PARP, HIF-1α and VEGF is decreased by treating with calcium lactate. Herein, these factors give a resistance to radiation. Thus, if the factors are decreased due to calcium lactate, the efficiency of radiation can be increase, which was verified.

Example 11-1: Setting of Experimental Groups Using Animal Model

A colorectal cancer cell (HT-29 or HCT-116) was subcutaneously implanted into the flank of mice. The mice were bred until the colorectal cancer cell grew to about 5 mm. Then, four groups were set up; a control group untreated with calcium lactate for 30 days, an experimental group 11 (intra tumor, I.T) injected with 2.5 mM calcium lactate, an experimental group 12 (IR) irradiated with radiation of 2 Gy five times using an X-RAD 320 X-ray irradiator (300 kVp) equipped with a 2.0 mm aluminum filter, and an experimental group 13 (CaLa+IR) irradiated with radiation of 2 Gy five times and injected with 2.5 mM calcium lactate at the same time (FIG. 36).

FIG. 36 is a schematic illustration of experimental scheme for the treatment with radiation and calcium lactate using animal models.

Example 11-2: Change in Tumor Size in Animal Model Treated with Radiation in Combination with Calcium Lactate The volumes of colorectal cancer tissues extracted from the mice of the control group or each of the experimental groups set up in Example 11-1 were measured over time and compared with each other (FIGS. 37a and 37b).

FIG. 37a provides a graph showing the change in tumor volume over time in an animal cancer model, which was prepared by implanting HT-29 colorectal cancer cell line into the flank depending on whether treated with radiation and calcium lactate individually or in combination, and FIG. 37b provides a graph showing the change in tumor volume over time in an animal cancer model, which was prepared by implanting a HCT-116 colorectal cancer cell line into the flank depending on whether treated with radiation and calcium lactate individually or in combination.

As can be seen from FIGS. 37a and 37b, it was confirmed that in the experimental groups treated with radiation and calcium lactate individually or in combination as compared with the control group untreated with radiation and calcium lactate, the growth of tumor is inhibited regardless of the type of colorectal cancer cell line implanted and particularly in the experimental group 13 treated with radiation in combination with calcium lactate, the growth of tumor is inhibited to the lowest level.

This result verified that the treatment with calcium lactate can inhibit expression of factors that give resistance to radiation, and was analyzed that in case of the treatment with calcium lactate in combination with radiation, the efficiency of anticancer treatment can be improved even with a smaller dose of radiation. Therefore, calcium lactate may be used alone for treating cancer. However, it can be seen that if calcium lactate is administered in combination with irradiation of radiation, an enhanced effect of anticancer treatment can be obtained.

Example 12: Treatment with Well-Known Anticancer Drug in Combination with Calcium Lactate Through Example 9-4, it was confirmed that the treatment with calcium lactate in combination with a material showing an anticancer activity decreases the viability of a cancer cell as compared with the treatment with calcium lactate or the material alone. On the basis of the result, a treatment effect of a well-known anticancer drug in combination with calcium lactate on various cancer cell lines was verified.

Example 12-1: Treatment with Imatinib in Combination with Calcium Lactate

Human colorectal cancer cell lines (HT-29 and HCT-116) with the cell number of 1×10$^3$ cells were seeded into an RPMI1640 medium in each of 6-well plates. After one day, the medium was replaced with fresh medium and the cells were treated with 2.5 mM calcium lactate or 1 μM, 2.5 μM, and 5 μM Imatinib alone or treated with various concentrations (1 μM, 2.5 μM, and 5 μM) of Imatinib in combination with 2.5 mM calcium lactate. Then, the colony-forming abilities of the cells were compared. In this case, human colorectal cancer cell lines (HT-29 and HCT-116) untreated with any drug were used as control groups (FIGS. 38a, 38b, 39a and 39b).

FIG. 38a shows the result of comparing the decrease in the number of colonies when a human colorectal cancer cell line (HT-29) was treated with 2.5 mM calcium lactate and 1 μM, 2.5 μM, and 5 μM Imatinib, alone or in combination. FIG. 38b shows the result of comparing the suppression of the formation of individual colony when a human colorectal cancer cell line (HT-29) was treated with 2.5 mM calcium lactate and IF, 2.5 μM, and 5 μM Imatinib, alone or in combination.

FIG. 39a shows the result of comparing the decrease in the number of colonies when a human colorectal cancer cell line (HCT-116) was treated with 2.5 mM calcium lactate and 1 µM, 2.5 µM, and 5 µM Imatinib, alone or in combination. FIG. 39b shows the result of comparing the suppression of the formation of individual colony when a human colorectal cancer cell line (HCT-116) was treated with 2.5 mM calcium lactate and 1 µM, 2.5 µM, and 5 µM Imatinib, alone or in combination. As can be seen from FIGS. 38a, 38b, 39a and 39b, it was confirmed that the colony-forming ability of the cancer cells is suppressed in the group treated with calcium lactate alone and the groups treated with low concentrations (1 µM, 2.5 µM, and 5 µM) of Imatinib alone as compared with the control group, and the colony-forming ability is further suppressed in the groups treated with Imatinib and calcium lactate in combination as compared with the groups treated with Imatinib alone.

Example 12-2: Treatment with 5-FU (5-Fluorourasil) in Combination with Calcium Lactate Human colorectal cancer cell lines (HT-29 and HCT-116) with the cell number of 1×10³ cells were seeded into an RPMI1640 medium in each of 6-well plates. After one day, the medium was replaced with fresh medium and the cells were treated with 2.5 mM calcium lactate or 2.5 µM, 5 µM, and 10 µM 5-FU alone or treated with various concentrations (2.5 µM, 5 µM, and 10 µM) of 5-FU in combination with 2.5 mM calcium lactate. Then, the colony-forming abilities of the cells were compared. In this case, human colorectal cancer cell lines (HT-29 and HCT-116) untreated with any drug were used as control groups (FIGS. 40a, 40b, 41a and 41b).

FIG. 40a shows the result of comparing the decrease in the number of colonies when a human colorectal cancer cell line (HT-29) was treated with 2.5 mM calcium lactate and 2.5 µM, 5 µM, and 10 µM 5-FU, alone or in combination. FIG. 40b shows the result of comparing the suppression of the formation of individual colony when a human colorectal cancer cell line (HT-29) was treated with 2.5 mM calcium lactate and 2.5 µM, 5 µM, and 1 µM 5-FU, alone or in combination. FIG. 41a shows the result of comparing the decrease in the number of colonies when a human colorectal cancer cell line (HCT-116) was treated with 2.5 mM calcium lactate and 2.5 µM, 5 µM, and 10 µM 5-FU, alone or in combination. FIG. 41b shows the result of comparing the suppression of the formation of individual colony when a human colorectal cancer cell line (HCT-16) was treated with 2.5 mM calcium lactate and 2.5 µM, 5 µM, and 10 µM 5-FU, alone or in combination. As can be seen from FIGS. 40a, 40b, 41a and 41b, it was confirmed that the colony-forming ability of the cancer cells is suppressed, in the group treated with calcium lactate alone and the groups treated with low concentrations (2.5 µM, 5 µM, and 10 µM) of 5-FU alone as compared with the control group, and the colony-forming ability is further suppressed, in the groups treated with 5-FU and calcium lactate in combination as compared with the groups treated with 5-FU alone.

Example 12-3: Treatment with Paclitaxel in Combination with Calcium Lactate

Human breast cancer cell line (MCF-7) and a human lung cancer cell line (A549) with the cell number of 1×10³ cells were seeded into an RPMI1640 medium in each of 6-well plates. After one day, the medium was replaced with fresh medium and the cells were treated with 2.5 mM calcium lactate or 0.63 nM, 1.3 nM, and 2.5 nM Paclitaxel alone or treated with various concentrations (0.63 nM, 1.3 nM, and 2.5 nM) of Paclitaxel in combination with 2.5 mM calcium lactate. Then, the colony-forming abilities of the cells were compared. In this case, a human breast cancer cell line (MCF-7) and a human lung cancer cell line (A549) untreated with any drug were used as control groups (FIGS. 42a, 42b, 43a and 43b).

FIG. 42a shows the result of comparing the decrease in the number of colonies when a human breast cancer cell line (MCF-7) was treated with 2.5 mM calcium lactate and 0.63 nM, 1.3 nM, and 2.5 nM Paclitaxel, alone or in combination. FIG. 42b shows the result of comparing the suppression of the formation of individual colony when a human breast cancer cell line (MCF-7) was treated with 2.5 mM calcium lactate and 0.63 nM, 1.3 nM, and 2.5 nM Paclitaxel, alone or in combination. As can be seen from FIGS. 42a and 42b, it was confirmed that in the group treated with calcium lactate alone and the groups treated with low concentrations (0.63 nM, 1.3 nM, and 2.5 nM) of Paclitaxel alone as compared with the control group, the colony-forming ability of the cancer cells is suppressed, and in the groups treated with Paclitaxel and calcium lactate in combination as compared with the groups treated with Paclitaxel alone, the colony-forming ability is further suppressed.

FIG. 43a shows the result of comparing the decrease in the number of colonies when a human lung cancer cell line (A549) was treated with 2.5 mM calcium lactate and 0.63 nM, 1.3 nM, and 2.5 nM Paclitaxel, alone or in combination. FIG. 43b shows the result of comparing the suppression of the formation of individual colony when a human lung cancer cell line (A549) was treated with 2.5 mM calcium lactate and 0.63 nM, 1.3 nM, and 2.5 nM Paclitaxel, alone or in combination. As can be seen from FIGS. 43a and 43b, it was confirmed that the colony-forming ability of the cancer cells is suppressed, in the group treated with calcium lactate alone and the groups treated with low concentrations (0.63 nM, 1.3 nM, and 2.5 nM) of Paclitaxel alone as compared with the control group, and the colony-forming ability is further suppressed, in the groups treated with Paclitaxel and calcium lactate in combination as compared with the groups treated with Paclitaxel alone.

Example 12-4: Treatment with Gefitinib in Combination with Calcium Lactate

Human lung cancer cell line (A549) with the cell number of 1×10³ cells were seeded into an RPMI1640 medium in each of 6-well plates. After one day, the medium was replaced with fresh medium and the cells were treated with 2.5 mM calcium lactate or 1.3 µM, 2.5 µM, and 5 µM Gefitinib alone or treated with various concentrations (1.3 µM, 2.5 µM, and 5 µM) of Gefitinib in combination with 2.5 mM calcium lactate. Then, the colony-forming abilities of the cells were compared. In this case, a human lung cancer cell line (A549) untreated with any drug was used as a control group (FIGS. 44a and 44b).

FIG. 44a shows the result of comparing the decrease in the number of colonies when a human lung cancer cell line (A549) was treated with 2.5 mM calcium lactate and 1.3 µM, 2.5 µM, and 5 µM Gefitinib, alone or in combination. FIG. 44b shows the result of comparing the suppression of the formation of individual colony when a human lung cancer cell line (A549) was treated with 2.5 mM calcium lactate and 1.3 µM, 2.5 µM, and 5 µM Gefitinib, alone or in combination. As can be seen from FIGS. 44a and 44b, it was confirmed that the colony-forming ability of the cancer cells is suppressed, in the group treated with calcium lactate alone and the groups treated with low concentrations (1.3 μM, 2.5 μM, and 5 μM) of Gefitinib alone as compared with the control group, and the colony-forming ability is further suppressed, in the groups treated with Gefitinib and calcium lactate in combination as compared with the groups treated with Gefitinib alone.

Example 12-5: Treatment with Sorafenib in Combination with Calcium Lactate

Human liver cancer cell line (Hep3B) with the cell number of $1\times10^3$ cells were seeded into an RPMI1640 medium in each of 6-well plates. After one day, the medium was replaced with fresh medium and the cells were treated with 2.5 mM calcium lactate or 1 μM, 2.5 μM, and 5 μM Sorafenib alone or treated with various concentrations (1 μM, 2.5 μM, and 5 μM) of Sorafenib in combination with 2.5 mM calcium lactate. Then, the colony-forming abilities of the cells were compared. In this case, a human liver cancer cell line (Hep3B) untreated with any drug was used as a control group (FIGS. 45a and 45b).

FIG. 45a shows the result of comparing the decrease in the number of colonies when a human hepatocellular carcinoma cell line (Hep3B) was treated with 2.5 mM calcium lactate and 1 μM, 2.5 μM, and 5 μM Sorafenib, alone or in combination. FIG. 45b shows the result of comparing the suppression of the formation of individual colony when a human hepatocellular carcinoma cell line (Hep3B) was treated with 2.5 mM calcium lactate and 1 μM, 2.5 μM, and 5 μM Sorafenib, alone or in combination. As can be seen from FIGS. 45a and 45b, it was confirmed that the colony-forming ability of the cancer cells is suppressed, in the group treated with calcium lactate alone and the groups treated with low concentrations (1 μM, 2.5 μM, and 5 μM) of Sorafenib alone as compared with the control group, and the colony-forming ability is further suppressed, the groups treated with Sorafenib and calcium lactate in combination as compared with the groups treated with Sorafenib alone.

Example 12-6: Treatment with Irinotecan in Combination with Calcium Lactate

Human colorectal cancer cell line (HT-29) with the cell number of $1\times10^3$ cells were seeded into an RPMI1640 medium in each of 6-well plates. After one day, the medium was replaced with fresh medium and the cells were treated with 2.5 mM calcium lactate or 0.5 μM, 1 μM, and 2 μM Irinotecan alone or treated with various concentrations (0.5 μM, 1 μM, and 2 μM) of Irinotecan in combination with 2.5 mM calcium lactate. Then, the colony-forming abilities of the cells were compared. In this case, a human colorectal cancer cell line (HT-29) untreated with any drug was used as a control group (FIGS. 46a and 46b).

FIG. 46a shows the result of comparing the decrease in the number of colonies when a human colorectal cancer cell line (HT-29) was treated with 2.5 mM calcium lactate and 0.5 μM, 1 μM, and 2 μM Irinotecan, alone or in combination. FIG. 46b shows the result of comparing the suppression of the formation of individual colony when a human colorectal cancer cell line (HT-29) was treated with 2.5 mM calcium lactate and 0.5 μM, 1 μM, and 2 μM Irinotecan, alone or in combination. As can be seen from FIGS. 46a and 46b, it was confirmed that the colony-forming ability of the cancer cells is suppressed, in the group treated with calcium lactate alone and the groups treated with low concentrations (0.5 μM, 1 μM, and 2 μM) of Irinotecan alone as compared with the control group, and the colony-forming ability is further suppressed, in the groups treated with Irinotecan and calcium lactate in combination as compared with the groups treated with Irinotecan alone.

Example 12-7: Treatment with Erlotinib in Combination with Calcium Lactate

Human lung cancer cell line (A549) with the cell number of $1\times10^3$ cells were seeded into an RPMI1640 medium in each of 6-well plates. After one day, the medium was replaced with fresh medium and the cells were treated with 2.5 mM calcium lactate or 0.5 μM, 1 μM, and 2 μM Erlotinib alone or treated with various concentrations (0.5 μM, 1 μM, and 2 μM) of Erlotinib in combination with 2.5 mM calcium lactate. Then, the colony-forming abilities of the cells were compared. In this case, a human lung cancer cell line (A549) untreated with any drug was used as a control group (FIGS. 47a and 47b).

FIG. 47a shows the result of comparing the decrease in the number of colonies when a human lung cancer cell line (A549) was treated with 2.5 mM calcium lactate and 0.5 μM, 1 μM, and 2 μM Erlotinib, alone or in combination. FIG. 47b shows the result of comparing the suppression of the formation of individual colony when a human lung cancer cell line (A549) was treated with 2.5 mM calcium lactate and 0.5 μM, 1 μM, and 2 μM Erlotinib, alone or in combination. As can be seen from FIGS. 47a and 47b, it was confirmed that the colony-forming ability of the cancer cells is suppressed, in the group treated with calcium lactate alone and the groups treated with low concentrations (0.5 μM, 1 μM, and 2 μM) of Erlotinib alone as compared with the control group, and the colony-forming ability is further suppressed, in the groups treated with Erlotinib and calcium lactate in combination as compared with the groups treated with Erlotinib alone.

Example 12-8: Treatment with Sunitinib in Combination with Calcium Lactate

Human colorectal cancer cell line (HT-29) with the cell number of $1\times10^3$ cells were seeded into an RPMI1640 medium in each of 6-well plates. After one day, the medium was replaced with fresh medium and the cells were treated with 2.5 mM calcium lactate or 0.5 μM, 1 μM, and 2 μM Sunitinib alone or treated with various concentrations (0.5 μM, 1 μM, and 2 μM) of Sunitinib in combination with 2.5 mM calcium lactate. Then, the colony-forming abilities of the cells were compared. In this case, a human colorectal cancer cell line (HT-29) untreated with any drug was used as a control group (FIGS. 48a and 48b).

FIG. 48a shows the result of comparing the decrease in the number of colonies when a human colorectal cancer cell line (HT-29) was treated with 2.5 mM calcium lactate and 0.5 μM, 1 μM, and 2 μM Sunitinib, alone or in combination. FIG. 48b shows the result of comparing the suppression of the formation of individual colony when a human colorectal cancer cell line (HT-29) was treated with 2.5 mM calcium lactate and 0.5 μM, 1 μM, and 2 μM Sunitinib, alone or in combination. As can be seen from FIGS. 48a and 48b, it was confirmed that the colony-forming ability of the cancer cells is suppressed, in the group treated with calcium lactate alone and the groups treated with low concentrations (0.5 μM, 1 μM, and 2 μM) of Sunitinib alone as compared with the control group, and the colony-forming ability is further suppressed, in the groups treated with Sunitinib and calcium lactate in combination as compared with the groups treated with Sunitinib alone.

Example 12-9: Treatment with Methotrexate in Combination with Calcium Lactate

Human lung cancer cell line (A549) with the cell number of $1\times10^3$ cells were seeded into an RPMI1640 medium in each of 6-well plates. After one day, the medium was replaced with fresh medium and the cells were treated with 2.5 mM calcium lactate or 5 nM, 10 nM, and 20 nM Methotrexate alone or treated with various concentrations (5 nM, 10 nM, and 20 nM) of Methotrexate in combination with 2.5 mM calcium lactate. Then, the colony-forming abilities of the cells were compared. In this case, a human lung cancer cell line (A549) untreated with any drug was used as a control group (FIGS. 49a and 49b).

FIG. 49a shows the result of comparing the decrease in the number of colonies when a human lung cancer cell line (A549) was treated with 2.5 mM calcium lactate and 5 nM, 10 nM, and 20 nM Methotrexate, alone or in combination. FIG. 49b shows the result of comparing the suppression of the formation of individual colony when a human lung cancer cell line (A549) was treated with 2.5 mM calcium lactate and 5 nM, 10 nM, and 20 nM Methotrexate, alone or in combination. As can be seen from FIGS. 49a and 49b, it was confirmed that the colony-forming ability of the cancer cells is suppressed, in the group treated with calcium lactate alone and the groups treated with low concentrations (5 nM, 10 nM, and 20 nM) of Methotrexate alone as compared with the control group, and the colony-forming ability is further suppressed, in the groups treated with Methotrexate and calcium lactate in combination as compared with the groups treated with Methotrexate alone.

Example 12-10: Treatment with Carboplatin in Combination with Calcium Lactate

Human lung cancer cell line (A549) with the cell number of $1\times10^3$ cells were seeded into an RPMI1640 medium in each of 6-well plates. After one day, the medium was replaced with fresh medium and the cells were treated with 2.5 mM calcium lactate or 2.5 μM, 5 μM, and 10 μM Carboplatin alone or treated with various concentrations (2.5 μM, 5 μM, and 10 μM) of Carboplatin in combination with 2.5 mM calcium lactate. Then, the colony-forming abilities of the cells were compared. In this case, a human lung cancer cell line (A549) untreated with any drug was used as a control group (FIGS. 50a and 50b).

FIG. 50a shows the result of comparing the decrease in the number of colonies when a human lung cancer cell line (A549) was treated with 2.5 mM calcium lactate and 2.5 μM, 5 μM, and 10 μM Carboplatin, alone or in combination. FIG. 50b shows the result of comparing the suppression of the formation of individual colony when a human lung cancer cell line (A549) was treated with 2.5 mM calcium lactate and 2.5 μM, 5 μM, and 10 μM Carboplatin, alone or in combination. As can be seen from FIGS. 50a and 50b, it was confirmed that the colony-forming ability of the cancer cells is suppressed, in the group treated with calcium lactate alone and the groups treated with low concentrations (2.5 μM, 5 μM, and 10 μM) of Carboplatin alone as compared with the control group, and the colony-forming ability is further suppressed, in the groups treated with Carboplatin and calcium lactate in combination as compared with the groups treated with Carboplatin alone.

Example 12-11: Treatment with Docetaxel in Combination with Calcium Lactate

Human lung cancer cell line (A549) with the cell number of $1\times10^3$ cells were seeded into an RPMI1640 medium in each of 6-well plates. After one day, the medium was replaced with fresh medium and the cells were treated with 2.5 mM calcium lactate or 0.6 nM, 1.3 nM, and 2.5 nM Docetaxel alone or treated with various concentrations (0.6 nM, 1.3 nM, and 2.5 nM) of Docetaxel in combination with 2.5 mM calcium lactate. Then, the colony-forming abilities of the cells were compared. In this case, a human lung cancer cell line (A549) untreated with any drug was used as a control group (FIGS. 51a and 51b).

FIG. 51a shows the result of comparing the decrease in the number of colonies when a human lung cancer cell line (A549) was treated with 2.5 mM calcium lactate and 0.6 nM, 1.3 nM, and 2.5 nM Docetaxel, alone or in combination. FIG. 51b shows the result of comparing the suppression of the formation of individual colony when a human lung cancer cell line (A549) was treated with 2.5 mM calcium lactate and 0.6 nM, 1.3 nM, and 2.5 nM Docetaxel, alone or in combination. As can be seen from FIGS. 51a and 51b, it was confirmed that the colony-forming ability of the cancer cells is suppressed, in the group treated with calcium lactate alone and the groups treated with low concentrations (0.6 nM, 1.3 nM, and 2.5 nM) of Docetaxel alone as compared with the control group, and the colony-forming ability is further suppressed in the groups treated with Docetaxel and calcium lactate in combination as compared with the groups treated with Docetaxel alone.

Example 12-12: Treatment with Lapatinib in Combination with Calcium Lactate

Human breast cancer cell line (MCF-7) with the cell number of $1\times10^3$ cells were seeded into an RPMI1640 medium in each of 6-well plates. After one day, the medium was replaced with fresh medium and the cells were treated with 2.5 mM calcium lactate or 2 μM, 4 μM, and 8 μM Lapatinib alone or treated with various concentrations (2 μM, 4 μM, and 8 μM) of Lapatinib in combination with 2.5 mM calcium lactate. Then, the colony-forming abilities of the cells were compared. In this case, a human breast cancer cell line (MCF-7) untreated with any drug was used as a control group (FIGS. 52a and 52b).

FIG. 52a shows the result of comparing the decrease in the number of colonies when a human breast cancer cell line (MCF-7) was treated with 2.5 mM calcium lactate and 2 μM, 4 μM, and 8 μM Lapatinib, alone or in combination. FIG. 52b shows the result of comparing the suppression of the formation of individual colony when a human breast cancer cell line (MCF-7) was treated with 2.5 mM calcium lactate and 2 μM, 4 μM, and 8 μM Lapatinib, alone or in combination. As can be seen from FIGS. 52a and 52b, it was confirmed that the colony-forming ability of the cancer cells is suppressed, in the group treated with calcium lactate alone and the groups treated with low concentrations (2 μM, 4 μM, and 8 μM) of Lapatinib alone as compared with the control group, and the colony-forming ability is further suppressed, in the groups treated with Lapatinib and calcium lactate in combination as compared with the groups treated with Lapatinib alone.

Example 12-13: Treatment with Everolimus in Combination with Calcium Lactate Human kidney cancer cell line (Caki-1) with the cell number of 1×10³ cells were seeded into an RPMI1640 medium in each of 6-well plates. After one day, the medium was replaced with fresh medium and the cells were treated with 0.3 nM, 0.5 nM, and 1 nM Everolimus alone or treated with various concentrations (0.3 nM, 0.5 nM, and 1 nM) of Everolimus in combination with 2.5 mM calcium lactate. Then, the colony-forming abilities of the cells were compared. In this case, a human kidney cancer cell line (Caki-1) untreated with any drug was used as a control group (FIGS. 53a and 53b).

FIG. 53a shows the result of comparing the decrease in the number of colonies when a human kidney cancer cell line (Caki-1) was treated with 2.5 mM calcium lactate and 0.3 nM, 0.5 nM, and 1 nM Everolimus, alone or in combination. FIG. 53b shows the result of comparing the suppression of the formation of individual colony when a human kidney cancer cell line (Caki-1) was treated with 2.5 mM calcium lactate and 0.3 nM, 0.5 nM, and 1 nM Everolimus, alone or in combination. As can be seen from FIGS. 53a and 53b, it was confirmed that the colony-forming ability of the cancer cells is suppressed, in the group treated with calcium lactate alone and the groups treated with low concentrations (0.3 nM, 0.5 nM, and 1 nM) of Everolimus alone as compared with the control group, and the colony-forming ability is further suppressed in the group treated with Everolimus and calcium lactate in combination as compared with the groups treated with Everolimus alone.

Example 12-14: Treatment with Trastuzumab (Herceptin) in Combination with Calcium Lactate Human breast cancer cell line (MCF-7) with the cell number of 1×10³ cells showing a resistance to an anticancer drug Trastuzumab were seeded into an RPM11640 medium (including 1% fetal bovine serum+500 ng/μl epithelial growth factor) in each of the 6-well plates. After one day, the medium was replaced with fresh medium and the cells were treated with 2.5 mM calcium lactate or 0.23 μg/ml, 0.45 μg/ml, and 1.8 μg/ml Trastuzumab alone or treated with various concentrations (0.23 μg/ml, 0.45 μg/ml, and 1.8 μg/ml) of Trastuzumab in combination with 2.5 mM calcium lactate. Then, the colony-forming abilities of the cells were compared. In this case, a human breast cancer cell line (MCF-7) untreated with any drug was used as a control group (FIGS. 54a and 54b).

FIG. 54a shows the result of comparing the decrease in the number of colonies when a human breast cancer cell line (MCF-7) was treated with 2.5 mM calcium lactate and 0.23 μg/ml, 0.45 μg/ml, and 1.8 μg/ml Trastuzumab, alone or in combination. FIG. 54b shows the result of comparing the suppression of the formation of individual colony when a human breast cancer cell line (MCF-7) was treated with 2.5 mM calcium lactate and 0.23 μg/ml, 0.45 μg/ml, and 1.8 μg/ml Trastuzumab, alone or in combination. As can be seen from FIGS. 54a and 54b, it was confirmed that the colony-forming ability is decreased, in the group treated with calcium lactate alone as compared with the control group, but the groups treated with low concentrations (0.23 μg/ml, 0.45 μg/ml, and 1.8 μg/ml) of Trastuzumab alone has little difference in colony-forming ability from the control group. However, it was confirmed that in the groups treated with 0.23 μg/ml, 0.45 μg/ml, and 1.8 μg/ml Trastuzumab in combination with calcium lactate showed the suppressed colony-forming ability to a lower level comparing with the groups treated with Trastuzumab alone which showed no effect of anticancer.

Example 12-15: Treatment with Oxaliplatin in Combination with Calcium Lactate Human colorectal cancer cell line (HT-29) with the cell number of 1×10³ cells were seeded into an RPMI1640 medium in each of 6-well plates. After one day, the medium was replaced with fresh medium and the cells were treated with 2.5 mM calcium lactate or 1.3 μM, 2.5 μM, and 5 μM Oxaliplatin alone or treated with various concentrations (1.3 μM, 2.5 μM, and 5 μM) of Oxaliplatin in combination with 2.5 mM calcium lactate. Then, the colony-forming abilities of the cells were compared. In this case, a human colorectal cancer cell line (HT-29) untreated with any drug was used as a control group (FIG. 55).

FIG. 55a shows the result of comparing the decrease in the number of colonies when a human colorectal cancer cell line (HT-29) was treated with 2.5 mM calcium lactate and 1.3 AM, 2.5 μM, and 5 μM Oxaliplatin, alone or in combination. FIG. 55b shows the result of comparing the suppression of the formation of individual colony when a human colorectal cancer cell line (HT-29) was treated with 2.5 mM calcium lactate and 1.3 μM, 2.5 μM, and 5 μM Oxaliplatin, alone or in combination. As can be seen from FIGS. 55a and 55b, it was confirmed that the colony-forming ability of the cancer cells is suppressed, in the group treated with calcium lactate alone and the groups treated with low concentrations (1.3 μM, 2.5 μM, and 5 μM) of Oxaliplatin alone as compared with the control group, and the colony-forming ability is further suppressed in the groups treated with Oxaliplatin and calcium lactate in combination as compared with the groups treated with Oxaliplatin alone. This result was analyzed to imply that in the case of the treating with calcium lactate in combination with a well-known anticancer drug, the efficiency of anticancer treatment can be improved even with a smaller amount of the anticancer drug.

Therefore, the enhanced anticancer activity can be shown when a cancer cell is treated with a metal lactate salt in combination with a well-known anticancer drug, even though anticancer activity can be shown when a cancer cell is treated with a metal lactate salt alone. Further, it can be seen from the result of Trastuzumab that the sensitivity of a cancer cell to a well-known anticancer drug can be further increased.

PCT/KR2015/013191 having an international filing date of Dec. 4, 2015 is herein incorporated by reference in its entirety.

What is claimed is:

1. A method of inhibiting metastasis of cancer in a subject in need thereof, comprising administering an effective amount of calcium lactate to the subject, wherein the calcium lactate is administered subcutaneously, intravenously, or intratumorally as a unit dose of a pharmaceutical composition comprising the calcium lactate in a concentration of 2.5 mM to 25 mM.

2. The method of claim 1, wherein the subject has lung cancer, breast cancer, colorectal cancer, stomach cancer, brain cancer, pancreatic cancer, thyroid cancer, skin cancer, bone cancer, lymphoma, uterine cancer, cervical cancer, kidney cancer, liver cancer, or melanoma.

3. The method of claim 1, wherein the calcium lactate is administered as the only active ingredient.

4. The method of claim 1, further comprising treating the subject with a radiation therapy.

5. The method of claim 4, wherein the subject is irradiated with an amount of radiation of 2 Gy per day to 10 Gy per day.

6. The method of claim 1, further comprising administering to the subject one or more additional anticancer drugs.

7. The method of claim 6, wherein the one or more additional anticancer drugs are selected from the group consisting of Imatinib, 5-Fluorouracil, Irinotecan, Sunitinib, Oxaliplatin, Paclitaxel, Lapatinib, Trastuzumab, Gefitinib, Erlotinib, Methotrexate, Carboplatin, Docetaxel, Everolimus, Sorafenib, 5-indane sulfonamide, cinnamic acid, and combinations thereof.

8. The method of claim 6, further comprising treating the subject with a radiation therapy.

9. The method of claim 1, wherein the administering delivers an amount of calcium lactate to cancer stem cells of the subject sufficient to induce a morphology change of the cancer stem cells.

10. The method of claim 1, wherein the administering delivers an amount of calcium lactate to cancer cells of the subject sufficient to inhibit angiogenesis.

11. The method of claim 1, wherein the administering delivers an amount of calcium lactate to cancer cells of the subject sufficient to inhibit expression of vascular endothelial growth factor (VEGF) or hypoxia-inducible factor-1 alpha (HIF-1 alpha) in the cancer cells.

12. The method of claim 1, wherein the administering delivers an amount of calcium lactate to cancer cells of the subject sufficient to inhibit glycolysis of glucose in the cancer cells.

13. The method of claim 1, wherein the administering delivers an amount of calcium lactate to cancer cells of the subject sufficient to increase pyruvate, increase lactate dehydrogenase B (LDH-B), or increase alpha-ketoglutarate in the cancer cells.

14. The method of claim 1, wherein the subject is a human.

15. A method of treating cancer in a subject in need thereof, comprising administering calcium lactate to the subject, wherein the calcium lactate is administered subcutaneously, intravenously, or intratumorally as a unit dose of a pharmaceutical composition comprising the calcium lactate in a concentration of 2.5 mM to 25 mM, and wherein the administering delivers an effective amount of calcium lactate to cancer cells of the subject to:
   a) decrease expression of beta-catenin as a cancer growth factor, poly ADP ribose polymerase (PARP), hypoxia-inducible factor-1 alpha (HIF-1 alpha), or vascular endothelial growth factor (VEGF) in the cancer cells;
   b) suppress glycolysis of glucose in the cancer cells; or
   c) inhibit angiogenesis.

16. The method of claim 15, wherein the administering delivers an effective amount of calcium lactate to cancer cells of the subject to increase pyruvate, increase lactate dehydrogenase B (LDH-B), or increase alpha-ketoglutarate in the cancer cells.

17. The method of claim 15, further comprising irradiating the subject or administering to the subject one or more additional anticancer drugs.

18. The method of claim 17, wherein the one or more additional anticancer drugs are selected from the group consisting of Imatinib, 5-fluorouracil, Irinotecan, Sunitinib, Oxaliplatin, Paclitaxel, Lapatinib, Trastuzumab, Gefitinib, Erlotinib, Methotrexate, Carboplatin, Docetaxel, Everolimus, Sorafenib, 5-indane sulfonamide, cinnamic acid, and combinations thereof.

19. The method of claim 17, comprising irradiating the subject with an amount of radiation of 2 Cry per day to 10 Gy per day.

20. A method of treating cancer in a subject in need thereof, consisting essentially of administering an effective amount of calcium lactate to the subject, wherein the calcium lactate is administered subcutaneously, intravenously, or intratumorally as a unit dose of a pharmaceutical composition comprising the calcium lactate in a concentration of 2.5 mM to 25 mM.

21. The method of claim 20, wherein the cancer is a metastatic cancer.

22. The method of claim 20, wherein the cancer is lung cancer, breast cancer, colorectal cancer, stomach cancer, brain cancer, pancreatic cancer, thyroid cancer, skin cancer, bone cancer, lymphoma, uterine cancer, cervical cancer, kidney cancer, liver cancer, or melanoma.

23. A liquid dosage form pharmaceutical composition comprising 2.5 mM to 25 mM calcium lactate and an anticancer drug selected from the group consisting of Imatinib, 5-fluorouracil, Irinotecan, Sunitinib, Oxaliplatin, Paclitaxel, Lapatinib, Trastuzumab, Gefitinib, Erlotinib, Methotrexate, Carboplatin, Docetaxel, Everolimus, Sorafenib, 5-indane sulfonamide, cinnamic acid, and combinations thereof as active ingredients and a pharmaceutically acceptable carrier, excipient, or diluent.

* * * * *